(12) United States Patent
Merkx-Jacques et al.

(10) Patent No.: US 9,951,326 B2
(45) Date of Patent: Apr. 24, 2018

(54) ENHANCING MICROBIAL METABOLISM OF C5 ORGANIC CARBON

(71) Applicant: MARA Renewables Corporation, Dartmouth (CA)

(72) Inventors: Alexandra Merkx-Jacques, Lower Sackville (CA); David Woodhall, Herring Cove (CA); Mark Scaife, Dartmouth (CA); Roberto E. Armenta, Dartmouth (CA); Denise Muise, Dartmouth (CA); Holly Rasmussen, Dartmouth (CA); Jeremy Benjamin, Mineville (CA)

( * ) Notice: Subject to any disclaimer, the term of this patent is extended or adjusted under 35 U.S.C. 154(b) by 0 days.

(21) Appl. No.: 15/208,849

(22) Filed: Jul. 13, 2016

(65) Prior Publication Data

US 2017/0015988 A1    Jan. 19, 2017

Related U.S. Application Data

(60) Provisional application No. 62/191,983, filed on Jul. 13, 2015, provisional application No. 62/354,444, filed on Jun. 24, 2016.

(51) Int. Cl.
| | |
|---|---|
| *C12N 1/11* | (2006.01) |
| *C12N 9/92* | (2006.01) |
| *C12N 9/12* | (2006.01) |
| *C07K 14/40* | (2006.01) |

(52) U.S. Cl.
CPC .............. *C12N 9/92* (2013.01); *C07K 14/40* (2013.01); *C12N 9/1205* (2013.01); *C12Y 207/01017* (2013.01); *C12Y 503/01005* (2013.01); *C07K 2319/21* (2013.01)

(58) Field of Classification Search
None
See application file for complete search history.

(56) References Cited

U.S. PATENT DOCUMENTS

| | | |
|---|---|---|
| 3,847,741 A | 11/1974 | Heady et al. |
| 3,957,587 A | 5/1976 | Armbruster et al. |
| 4,341,038 A | 7/1982 | Bloch et al. |
| 4,680,314 A | 7/1987 | Nonomura |
| 4,687,742 A | 8/1987 | Skoet et al. |
| 4,894,331 A | 1/1990 | Ratzkin et al. |
| 4,952,511 A | 8/1990 | Radmer |
| 5,041,378 A * | 8/1991 | Drummond .......... C12N 9/2462 435/169 |
| 5,070,018 A | 12/1991 | Peters et al. |
| 5,104,803 A | 4/1992 | Delente |
| 5,130,242 A | 7/1992 | Barclay |
| 5,151,347 A | 9/1992 | Delente et al. |
| 5,162,051 A | 11/1992 | Hoeksema |
| 5,164,308 A | 11/1992 | Kyle |
| 5,168,056 A | 12/1992 | Frost |
| 5,171,680 A | 12/1992 | Mullenbach et al. |
| 5,244,921 A | 9/1993 | Kyle et al. |
| 5,254,468 A | 10/1993 | Fournier et al. |
| 5,268,280 A | 12/1993 | Starnes et al. |
| 5,272,073 A | 12/1993 | Frost et al. |
| 5,324,658 A | 6/1994 | Cox et al. |
| 5,340,594 A | 8/1994 | Barclay |
| 5,340,742 A | 8/1994 | Barclay |
| 5,374,657 A | 12/1994 | Kyle |
| 5,376,540 A | 12/1994 | Kyle |
| 5,397,591 A | 3/1995 | Kyle et al. |
| 5,407,957 A | 4/1995 | Kyle et al. |
| 5,411,886 A | 5/1995 | Udaka et al. |
| 5,466,434 A | 11/1995 | Kyle |
| 5,487,987 A | 1/1996 | Frost et al. |
| 5,492,938 A | 2/1996 | Kyle et al. |
| 5,514,583 A | 5/1996 | Picataggio et al. |
| 5,518,918 A | 5/1996 | Barclay |
| 5,539,133 A | 7/1996 | Kohn et al. |
| 5,547,699 A | 8/1996 | Iizuka et al. |
| 5,550,156 A | 8/1996 | Kyle |
| 5,567,732 A | 10/1996 | Kyle et al. |
| 5,583,019 A | 12/1996 | Barclay |
| 5,616,496 A | 4/1997 | Frost et al. |
| 5,629,181 A | 5/1997 | Frost et al. |
| 5,656,319 A | 8/1997 | Barclay |
| 5,656,497 A | 8/1997 | Zeikus et al. |
| 5,658,767 A | 8/1997 | Kyle |
| 5,688,500 A | 11/1997 | Barclay |
| 5,698,244 A | 12/1997 | Barclay |
| 5,711,983 A | 1/1998 | Kyle et al. |
| 5,712,133 A | 1/1998 | Picataggio et al. |
| 5,726,053 A | 3/1998 | Picataggio et al. |
| 5,798,237 A | 8/1998 | Picataggio et al. |
| 5,843,760 A | 12/1998 | Zhang et al. |
| 5,882,703 A | 3/1999 | Barclay |
| 5,908,622 A | 6/1999 | Barclay |
| 5,935,837 A | 8/1999 | Rasmussen |
| 5,985,348 A | 11/1999 | Barclay |

(Continued)

FOREIGN PATENT DOCUMENTS

| | | |
|---|---|---|
| CA | 2810198 A1 | 1/2012 |
| CA | 2810915 A1 | 4/2012 |

(Continued)

OTHER PUBLICATIONS

Thraustochytriaceae Family Data Sheet, 2007, 2 pages.

(Continued)

*Primary Examiner* — James S Ketter
(74) *Attorney, Agent, or Firm* — Kilpatrick Townsend & Stockton, LLP

(57) ABSTRACT

Provided herein are recombinant microorganisms having two or more copies of a nucleic acid sequence encoding xylose isomerase, wherein the nucleic acid encoding the xylose isomerase is an exogenous nucleic acid. Optionally, the recombinant microorganisms include at least one nucleic acid sequence encoding a xylulose kinase and/or at least one nucleic acid sequence encoding a xylose transporter. The provided recombinant microorganisms are capable of growing on xylose as a carbon source.

34 Claims, 20 Drawing Sheets

(56) References Cited

U.S. PATENT DOCUMENTS

| | | |
|---|---|---|
| 6,027,900 A | 2/2000 | Allnutt et al. |
| 6,054,147 A | 4/2000 | Barclay et al. |
| 6,103,225 A | 8/2000 | Barclay |
| 6,140,365 A | 10/2000 | Kiy et al. |
| 6,140,486 A | 10/2000 | Facciotti et al. |
| 6,166,230 A | 12/2000 | Bijl et al. |
| 6,166,231 A | 12/2000 | Hoeksema |
| 6,177,108 B1 | 1/2001 | Barclay |
| 6,180,376 B1 | 1/2001 | Liddell |
| 6,255,505 B1 | 7/2001 | Bijl et al. |
| 6,350,890 B1 | 2/2002 | Kiy et al. |
| 6,372,460 B1 | 4/2002 | Gladue et al. |
| 6,395,778 B1 | 5/2002 | Luthria |
| 6,399,803 B1 | 6/2002 | Corley et al. |
| 6,410,281 B1 | 6/2002 | Barclay |
| 6,410,282 B1 | 6/2002 | Kumar et al. |
| 6,441,208 B2 | 8/2002 | Bijl et al. |
| 6,451,567 B1 | 9/2002 | Barclay |
| 6,461,839 B2 | 10/2002 | Yokochi et al. |
| 6,475,768 B1 | 11/2002 | Otero et al. |
| 6,509,178 B1 | 1/2003 | Tanaka et al. |
| 6,541,049 B2 | 4/2003 | Barclay |
| 6,566,123 B1 | 5/2003 | Barclay |
| 6,568,351 B1 | 5/2003 | Barclay et al. |
| 6,582,941 B1 | 6/2003 | Yokochi et al. |
| 6,596,766 B1 | 6/2003 | Igarashi et al. |
| 6,607,900 B2 | 8/2003 | Bailey et al. |
| 6,727,373 B2 | 4/2004 | Bijl et al. |
| 6,749,849 B2 | 6/2004 | Barclay |
| 6,750,048 B2 | 6/2004 | Ruecker et al. |
| 6,783,951 B2 | 8/2004 | Long, II |
| 6,812,009 B2 | 11/2004 | Gladue et al. |
| 6,977,167 B2 | 12/2005 | Barclay |
| 7,001,772 B2 | 2/2006 | Roessler et al. |
| 7,005,280 B2 | 2/2006 | Barclay |
| 7,011,962 B2 | 3/2006 | Barclay |
| 7,022,512 B2 | 4/2006 | Barclay |
| 7,033,584 B2 | 4/2006 | Barclay |
| 7,063,855 B2 | 6/2006 | Hjaltason et al. |
| 7,067,145 B2 | 6/2006 | Place et al. |
| 7,223,575 B2 | 5/2007 | Zhang et al. |
| 7,247,461 B2 | 7/2007 | Metz et al. |
| 7,259,006 B2 | 8/2007 | Komazawa et al. |
| 7,351,558 B2 | 4/2008 | Ruecker et al. |
| 7,374,908 B2 | 5/2008 | Yamaoka |
| 7,381,558 B2 | 6/2008 | Barclay |
| 7,419,596 B2 | 9/2008 | Dueppen et al. |
| 7,514,244 B2 | 4/2009 | Tanaka et al. |
| 7,923,226 B2 | 4/2011 | Frost |
| 8,163,515 B2 | 4/2012 | Burja et al. |
| 8,168,225 B2 | 5/2012 | Casaña Giner et al. |
| 8,383,377 B2 | 2/2013 | Yanase et al. |
| 8,399,215 B2 | 3/2013 | Klaasen et al. |
| 8,440,449 B2 | 5/2013 | Hughes et al. |
| 8,623,623 B2 | 1/2014 | Kahsay et al. |
| 8,637,279 B2 | 1/2014 | Chung et al. |
| 8,669,076 B1 | 3/2014 | Chen et al. |
| 8,748,152 B1 | 6/2014 | Hector et al. |
| 8,772,012 B2 | 7/2014 | Katahira et al. |
| 2003/0060509 A1 | 3/2003 | Elswyk |
| 2003/0143659 A1 | 7/2003 | Bijl et al. |
| 2003/0180898 A1 | 9/2003 | Bailey et al. |
| 2004/0067574 A1 | 4/2004 | Bijl et al. |
| 2006/0094089 A1 | 5/2006 | Barclay |
| 2006/0216804 A1 | 9/2006 | Karhumaa |
| 2006/0281908 A1 | 12/2006 | Callen |
| 2008/0138872 A1 | 6/2008 | Smith et al. |
| 2008/0155888 A1 | 7/2008 | Vick et al. |
| 2008/0220515 A1 | 9/2008 | McCall |
| 2009/0029445 A1 | 1/2009 | Eckleberry et al. |
| 2009/0077863 A1 | 3/2009 | Oyler |
| 2009/0081748 A1 | 3/2009 | Oyler |
| 2009/0117194 A1 | 5/2009 | Burja et al. |
| 2009/0246846 A1 | 10/2009 | Viitanen et al. |
| 2010/0099901 A1 | 4/2010 | Hayashi et al. |
| 2010/0234581 A1 | 9/2010 | Concilio et al. |
| 2010/0304454 A1 | 12/2010 | De Bont |
| 2011/0189728 A1 | 8/2011 | Klaassen et al. |
| 2011/0195448 A1* | 8/2011 | Lippmeier ............... C12N 1/22 435/41 |
| 2011/0269180 A1 | 11/2011 | Brat et al. |
| 2011/0269200 A1 | 11/2011 | Sanny et al. |
| 2011/0318790 A1 | 12/2011 | Teunissen et al. |
| 2012/0142067 A1 | 6/2012 | Desfougeres et al. |
| 2012/0225451 A1 | 9/2012 | Winkler et al. |
| 2012/0225452 A1 | 9/2012 | Bao et al. |
| 2012/0244584 A1 | 9/2012 | Zhang et al. |
| 2013/0084617 A1 | 4/2013 | Op Den Camp et al. |
| 2013/0157331 A1 | 6/2013 | Caimi et al. |
| 2013/0330800 A1 | 12/2013 | Varanasi et al. |
| 2014/0011241 A1 | 1/2014 | Beatty et al. |
| 2014/0017765 A1 | 1/2014 | Subbian et al. |
| 2014/0017768 A1 | 1/2014 | Jordan et al. |
| 2014/0080192 A1 | 3/2014 | Rajgarhia et al. |
| 2014/0162312 A1 | 3/2014 | Reed |
| 2014/0099720 A1 | 4/2014 | Ronnow et al. |
| 2014/0178954 A1 | 6/2014 | Hitz et al. |
| 2014/0370561 A1 | 12/2014 | Argyros et al. |
| 2014/0377816 A1 | 12/2014 | Rah et al. |

FOREIGN PATENT DOCUMENTS

| | | |
|---|---|---|
| CN | 101260394 A | 9/2008 |
| CN | 101323858 A | 12/2008 |
| CN | 101475955 A | 7/2009 |
| CN | 101698839 A | 4/2010 |
| CN | 101698840 A | 4/2010 |
| CN | 101705255 A | 5/2010 |
| CN | 102399804 A | 4/2012 |
| CN | 102433354 A | 5/2012 |
| CN | 102643844 A | 8/2012 |
| CN | 102643845 A | 8/2012 |
| CN | 102747062 A | 10/2012 |
| CN | 102747063 A | 10/2012 |
| CN | 102876595 A | 1/2013 |
| CN | 102888420 A | 1/2013 |
| CN | 103131720 A | 6/2013 |
| EP | 2554668 A1 | 2/2013 |
| JP | H03247288 A | 11/1991 |
| JP | H11243954 A | 9/1999 |
| JP | 2002355086 A | 10/2002 |
| JP | 2010239925 A | 10/2010 |
| JP | 2012170440 A | 9/2012 |
| KR | 20080105064 A | 12/2008 |
| KR | 101187717 B1 | 10/2012 |
| WO | 1987003899 A1 | 7/1987 |
| WO | 1989000606 A1 | 1/1989 |
| WO | 1989001520 A1 | 2/1989 |
| WO | 1990000196 A1 | 1/1990 |
| WO | 1992013086 A1 | 8/1992 |
| WO | 1995028476 A1 | 10/1995 |
| WO | 1997037032 A2 | 10/1997 |
| WO | 2000005395 A1 | 2/2000 |
| WO | 2000054575 A2 | 9/2000 |
| WO | 2002010322 A1 | 2/2002 |
| WO | 2002092540 A1 | 11/2002 |
| WO | 2003062387 A1 | 7/2003 |
| WO | 2006009434 A1 | 1/2006 |
| WO | 2007018442 A2 | 2/2007 |
| WO | 2007068997 A2 | 6/2007 |
| WO | 2007069078 A2 | 6/2007 |
| WO | 2007074479 A1 | 7/2007 |
| WO | 2007091117 A1 | 8/2007 |
| WO | 2008090989 A1 | 7/2008 |
| WO | 2008129358 A2 | 10/2008 |
| WO | 2009109630 A1 | 1/2009 |
| WO | 2009109631 A1 | 1/2009 |
| WO | 2009034124 A1 | 3/2009 |
| WO | 2009081941 A1 | 7/2009 |
| WO | 2010086840 A2 | 8/2010 |
| WO | 2011056004 A2 | 5/2011 |
| WO | 2011090730 A1 | 7/2011 |
| WO | 2011131667 A1 | 10/2011 |

(56) References Cited

FOREIGN PATENT DOCUMENTS

| | | |
|---|---|---|
| WO | 2012007646 A1 | 1/2012 |
| WO | 2012009272 A2 | 1/2012 |
| WO | 2012024046 A2 | 2/2012 |
| WO | 2012120375 A1 | 9/2012 |
| WO | 2012154626 A1 | 11/2012 |
| WO | 2012159571 A1 | 11/2012 |
| WO | 2013003219 A1 | 1/2013 |
| WO | 2013081456 A1 | 6/2013 |
| WO | 2013117631 A1 | 8/2013 |

OTHER PUBLICATIONS

Omega-3 News, Ocean Nutrition Canada Ltd., 2011, 3 pages.

Breakthrough Process to Extract Oil from Algae, http://www.miningtopnews.com/originoil-announces-breakthrough-process-to-extract-oil-from-.htm., Apr. 20, 2009, 4 pages.

Oil from Algae, Oilgae Glossary, Available online at http://www.oilgae.com/algae/oil/extract/extract.html, Jun. 4, 2009, 8 pages.

Bajpai et al., Optimization of production of docosahexaenoic acid (DHA) by Thraustochytrium aureum ATCC 34304, Journal of the American Oil Chemists Society, vol. 68, Issue 7, Jul. 1991, pp. 509-514.

Bajpai et al., Production of docosahexaenoic acid by Thraustochytrium aureum, Applied Microbiology and Biotechnology, vol. 35, Issue 6, Sep. 1991, pp. 706-710.

Baldwin, Application for the Approval of DHA-rich Oil, Omega Tech GmbH, Version no. Draft, 1997, 104 pages.

Barclay et al., Heterotrophic production of long chain omega-3 fatty acids utilizing algae and algae-like microorganisms, Journal of Applied Phycology, vol. 6, Issue 2, Apr. 1994, pp. 123-129.

Bateman et al., Method for Extraction and Separation by Solid Phase Extraction of Neutral Lipid, Free Fatty Acids, and Polar Lipid from Mixed Microbial Cultures, Journal of Agricultural and Food Chemistry, Jan. 20, 1997, pp. 132-134.

Bligh et al., A Rapid Method of Total Lipid Extraction and Purification, Canadian Journal of Biochemistry and Physiology, vol. 37, Issue 8, 1959, pp. 911-917.

Bowles et al., Long-chain n-3 polyunsaturated fatty acid production by members of the marine protistan group the thraustochytrids: screening of isolates and optimisation of docosahexaenoic acid production, Journal of Biotechnology, vol. 70, Issues 1-3, Apr. 1999, pp. 193-202.

Burja et al., Evaluation of fatty acid extraction methods for *Thraustochytrium* sp. ONC-T18, J. Agric. Food Chem., vol. 55, Issue 12, May 12, 2007, pp. 4795-4801.

Burja et al., Isolation and characterization of polyunsaturated fatty acid producing *Thraustochytrium* species: screening of strains and optimization of omega-3 production, Applied Microbiology and Biotechnology, vol. 72, Issue 6, Oct. 2006, pp. 1161-1169.

Fu et al., Study on Production of EPA and DHA in Microbe Fermentation, Grain Processing, Issue 1, 2004, pp. 48-51.

Hauvermale et al., Fatty Acid Production in *Schizochytrium* sp.: Involvement of a Polyunsaturated Fatty Acid Synthase and a Type 1 Fatty Acid Synthase, Lipids, vol. 41, Issue 8, XP002581593, 2006, pp. 739-747.

Iida et al., Improvement of docosahexaenoic acid production in a culture of Thraustochytrium aureum by medium optimization, Journal of Fermentation and Bioengineering, vol. 81, Issue 1, 1996, pp. 76-78.

Kaulmann et al., Biosynthesis of Polyunsaturated Fatty Acids by Polyunsaturated Synthases, Angewandte Chemie International Edition, vol. 41, Issue 11, Jun. 3, 2002, pp. 1866-1869.

Lewis et al., Evaluation of extraction methods for recovery of fatty acids from lipid-producing microheterotrophs, Journal of Microbiological Methods, vol. 43, Issue 2, Dec. 15, 2000, pp. 107-116.

Li et al., Production of docosahexaenoic acid by Thraustochytrium roseum, Journal of Industrial Microbiology, vol. 13, Issue 4, Aug. 1994, pp. 238-241.

Liu, Study on Production of EPA and DHA in Microbe Fermentation, Food Science and Technology, No. 6, 2004, pp. 13-16.

Marine Biopharmacy, Marine Biopharmacy fermentation engineering, Beijing Chemical Industry Press, 2002, pp. 96-101.

Metz et al., Production of polyunsaturated fatty acids by polyketide synthases in both prokaryotes and eukaryotes, Science, vol. 293, Issue 5528, Jul. 2001, pp. 290-293.

Molina Grima et al., Recovery of microalgal biomass and metabolites: process options and economics, Biotechnology Advances, vol. 20, Issues 7-8, Jan. 2003, pp. 491-515.

Nakahara et al., Production of docosahexaenoic and docosapentaenoic acids by*Schizochytrium* sp. isolated from Yap Islands, Journal of the American Oil Chemists' Society, vol. 73, Issue 11, Nov. 1996, pp. 1421-1426.

Pinkart et al., Rapid separation of microbial lipids using solid phase extraction columns, Journal of Microbiological Methods, vol. 34, Issue 1, Sep. 1, 1998, pp. 9-15.

Ratledge et al., Single cell oils—A coming of age, Lipid Technology, vol. 16, Feb. 2004, pp. 34-39.

Sijtsma et al., Recent advances in fatty acid synthesis in oleaginous yeasts and microalgae, Recent Research Developments in Microbiology, vol. 2, Jan. 1998, pp. 219-232.

Singh et al., Docosahexaenoic acid (DHA) production by *Thraustochytrium* sp. ATCC 20892, World Journal of Microbiology and Biotechnology, vol. 12, Issue 1, Jan. 1996, pp. 76-81.

Song et al., Effective Phase Separation of Biomass Pyrolysis Oils by Adding Aqueous Salt Solutions, Energy and Fuels, vol. 23, 2009, pp. 3307-3312.

Wardencki et al., Trends in solventless sample preparation techniques for environmental analysis, Journal of Biochemical and Biophysical Methods, vol. 70, Issue 2, 2007, pp. 275-288.

Yamaoka et al., Growth Characterization and Resources of Thraustochytrium CHN-1 Isolated from the Seto Inland Sea, Bulletin of the Society of Sea Water Science, Japan, vol. 59, No. 1, 2005, pp. 23-31.

Yokochi et al., Optimization of docosahexaenoic acid productions by Schizochytrium limacinum SR21, Applied Microbiology and Biotechnology, vol. 49, Issue 1, Jan. 1998, pp. 72-76.

Singh, et al., "Renewable fuels from algae: An answer to debatable land based fuels," Bioresource Technology vol. 102, Issue 1, Jan. 2011, pp. 10-16.

Lee, et al., "Metabolic engineering of microorganisms for biofuels production: from bugs to synthetic biology to fuels," Current Opinion in Biotechnology, vol. 19, Issue 6, Dec. 2008, pp. 556-563.

Canakci, et al., "Biodiesel production from various feedstocks and their effects on the fuel properties." Journal of Industrial Microbiology & Biotechnology May 2008, vol. 35, Issue 5, pp. 431-441.

Chen, et al., "Metabolic evolution of non-transgenic *Escherichia coli* SZ420 for enhanced homoethanol fermentation xylose," Biotechnology Letters Jan. 2010, 32:87.

Ha, et al., Engineered *Saccharomyces cerevisiae* capable of simultaneous cellobiose and xylose fermentation, PNAS/ Jan. 11, 2011, vol. 108, No. 2, pp. 504-509.

Lippmeier, et al., "Characterization of both polyunsaturated fatty acid biosynthetic pathways in *Schizochytrium* sp." Lipids, 2009; July 44(7):621-630.

Jeffries, et al., "Genetic engineering for improved xylose fermentation by yeasts," Adv Biochem Eng Biotechnolo 1999;65:117-61.

Runquist, et al., "Comparison of heterologous xylose transporters in recombinant *Saccharomyces cerevisiae*," Biotechnol Biofuels 2010;3:5.

Ho, et al., "Successful design and development of genetically engineered *Saccharomyces* yeasts for effective cofermentation of glucose and xylose from cellulosic biomass to fuel ethanol," Adv. Biochem Eng Biotechnol 1999;65:163-92.

Leonard, et al., "A Cuphea B-Ketoacyl-ACP Synthase Shiefts the Synthesis of Fatty Acids Toward Shorter Chains in Arabidpossis Seeds Expressing Cuphea FatB Thioesterases," The Plant Journal 1998 13(5), pp. 621-628.

Radakovitz, et al., "Genetic engineering of fatty acid chain length in Phaeodactylum tricornutum," Metabolic Engineering vol. 131, Issue 1, Jan. 2011, pp. 89-95.

(56) References Cited

OTHER PUBLICATIONS

Slabaugh, et al., "Condensing Enzymes from Cuphea Wrightii Associated with Medium Chain Fatty Acid Biosynthesis," The Plant Journal (1998) 13(5), 611-620.
Moreira dos Santos, et al., "Manipulation of malic enzyme in *Saccharomyces cerevisiae* for increasing NADPH production capacity aerobically in different cellular compartments," Metab Eng 6(4):352-63. (2004).
Martinez, et al., "Replacing *Escherichia coli* NAD-dependent glyceraldehyde 3-phosphate dehydrogenase (GAPDH) with a NADP-dependent enzyme from Clostridium acetobutylicum facilitates NADPH dependent pathways," Metab Eng 2008;10:352-9.
Verho, et al., "Engineering Redox Cofactor Regeneration for Improved Pentose Fermentation in *Saccharomyces cerevisiae*," Applied and Environmental microbiology, Oct. 2003, pp. 5892-597.
Kabir, et al., "Fermentation characteristics and protein expression patterns in a recombinant *Escherichia coli* mutant lacking phosphoglucose isomerase for poly(3-hydroxybutyrate) production," Appl Microbiol Biotechnol (2003) 62:244-55.
International Search Report and Written Opinion for related PCT Application No. PCT/IB2016/054185 dated Sep. 26, 2016.

\* cited by examiner

Codon optimization of E. coli xylB. Seq 1 = E. coli sequence; Seq 2 = T18 codon optimized xylB

```
Alignment of Sequence_1:  [E coli xylb.txt.xdna] with  Sequence_2: [xylb T18
cdnop.txt.xdna]

Similarity : 1081/1455 (74.30 %)

Seq_1    1     atgtatatcgggatagatcttggcacctcgggcgtaaaagttatttttgctcaacgagcag    60
                |||| #||||#||#||#||#|||||||||||||#||#||#||##|#||||||||||||||
Seq_2    1     atgtacatcggcatcgacctcggcacctcgggcgtcaaggtcatcctcctcaacgagcag    60

Seq_1    61    ggtgaggtggttgctgcgcaaacggaaaagctgaccgtttcgcgcccgcatccactctgg    120
                ||#|||||#||#||#||#||#||#||#||#||||#|||||||||||||#||#||||||
Seq_2    61    ggcgaggtcgtcgccgcccagaccgagaagctcaccgtctcgcgcccgcaccgctctgg    120

Seq_1    121   tcggaacaagacccggaacagtggtggcaggcaactgatcgcgcaatgaaagctctggc    180
                ||||#|#||||||||#||||||||||||||#||#||#||#||#||||||#||#|#|||
Seq_2    121   tcggagcaggacccggagcagtggtggcaggccaccgaccgcgccatgaaggccctcggc    180

Seq_1    181   gatcagcattctctgcaggacgttaaagcattgggtattgccggccagatgcacggagca    240
                |#||||||#|#||#||||||||#|#||##|#||#|#||#|||||||||||||||#|#
Seq_2    181   gaccagcactcgctccaggacgtcaaggccctcggcatcgccgccagatgcacggcgcc    240

Seq_1    241   accttgctggatgctcagcaacgggtgttacgccctgccattttgtggaacgacgggcgc    300
                |||#|#||#||#||#||#|||||#|#|||##|#||||||##|#||||||||||||#|||
Seq_2    241   accctcctcgacgcccagcagcgcgtcctccgcccggccatcctctggaacgacgggcgc    300

Seq_1    301   tgtgcgcaagagtgcactttgctggaagcgcgagttccgcaatcgcgggtgattaccggc    360
                ||#|#||#||||||||##|#||#||#||#||#||#||#|||||#||||#|#||||||
Seq_2    301   tgcgcccaggagtgcaccctcctcgaggcccgcgtccgcagtcgcgcgtcatcaccggc    360

Seq_1    361   aacctgatgatgcccggatttactgcgcctaaattgctatgggttcagcggcatgagccg    420
                |||#|#||#|||||||||#||#||#||#||#||#||##|#|#||||#||#|#||||||
Seq_2    361   aacctcatgatgccgggcttcaccgccccgaagctcctctgggtccagcgccacgagccg    420

Seq_1    421   gagatattccgtcaaatcgacaaagtattattaccgaaagattacttgcgtctgcgtatg    480
                |||||#||##|#||||#|#|||||#|###|##|||##|#|||#|#||#|#||#|#|||
Seq_2    421   gagatcttccgccagatcgacaaggtcctcctcccgaaggactacctccgcctccgcatg    480

Seq_1    481   acggggagtttgccagcgatatgtctgacgcagctggcaccatgtggctggatgtcgca    540
                ||#||#||||#|###|#||||#||#||#||#||#||||||||||||||||#||#|||#
Seq_2    481   accggcgagttcgcctcggacatgtcggacgccgccggcaccatgtggctcgacgtcgcc    540

Seq_1    541   aagcgtgactggagtgacgtcatgctgcaggcttgcgacttatctcgtgaccagatgccc    600
                ||||#|||||||###|||||||||||||||#|||||#||#|#|#|#|#||||||||||#
Seq_2    541   aagcgcgactggtcggacgtcatgctccaggcctgcgacctctcgcgaccagatgccg    600

Seq_1    601   gcattatacgaaggcagcgaaattactggtgctttgttacctgaagttgcgaaagcgtgg    660
                |##|#|||||||#||||#||||#||#|##|##|#|#|#|#|#|#|#||||#|#||
Seq_2    601   gccctctacgagggctcggagatcaccggcgccctcctcccggaggtcgccaaggcctgg    660

Seq_1    661   ggtatggcgacggtgccagttgtcgcaggcggtggcgacaatgcagctggtgcagttggt    720
                ||#||||||||#|#||#|#||#|#|#|#||##||#|||#|#||#||#|#||#|#||#
Seq_2    661   ggcatggccaccgtcccggtcgtcgccggcggcggcgacaacgccgccggcgccgtcggc    720
```

FIG. 18-1

```
Seq_1  661   ggtatggcgacggtgccagttgtcgcaggcggtggcgacaatgcagctggtgcagttggt  720
             ||#||||#||#||#||#||#||||#||||#|||||||||#||#||#||#||#||#||||#
Seq_2  661   ggcatggccaccgtcccggtcgtcgccggcggcggcgacaacgccgccggcgccgtcggc  720

Seq_1  721   gtgggaatggttgatgctaatcaggcaatgttatcgctggggacgtcggggggtctatttt  780
             ||#||#||||#||#||#||#||||#||#||#||||#||#||#||||#|||||#||#
Seq_2  721   gtcggcatggtcgacgccaaccaggccatgctctcgctcggcacctcgggcgtctacttc  780

Seq_1  781   gctgtcagcgaagggttcttaagcaagccagaaagcgccgtacatagcttttgccatgcg  840
             ||#|||###|#||#|||#|####||||#|####||||#|####|#|||||#||#
Seq_2  781   gccgtctcggagggcttcctctcgaagccggagtcggccgtccactcgttctgccacgcc  840

Seq_1  841   ctaccgcaacgttggcatttaatgtctgtgatgctgagtgcagcgtcgtgtctggattgg  900
             ||#|||||#|#||||##|#||||#||#||||####|#||#||||#|#|#|||
Seq_2  841   ctcccgcagcgctggcacctcatgtcggtcatgctctcggccgctcgtgcctcgactgg  900

Seq_1  901   gccgcgaaattaaccggcctgagcaatgtcccagctttaatcgctgcagctcaacaggct  960
             ||||#|##|#|||||||####|#|||#||##|#||#|#|#|#||||#
Seq_2  901   gccgccaagctcaccggcctctcgaacgtcccggccctcatcgccgcgcccagcaggcc  960

Seq_1  961   gatgaaagtgccgagccagtttggtttctgccttatctttccggcgagcgtacgccacac  1020
             ||#|####||||||||#|#||||#|#|#|#|#|#|||||||#|#|#|||
Seq_2  961   gacgagtcggccgagccggtctggttcctcccgtacctctcggcgagcgcaccccgcac  1020

Seq_1  1021  aataatcccaggcgaagggggttttctttggtttgactcatcaacatggccccaatgaa  1080
             ||#|#||||#|||||#|||#|#||||#|##|#|#|#|#|#||||#||#|#
Seq_2  1021  aacaacccgcaggccaagggcgtcttcttcggcctcacccaccagcacggccgaacgag  1080

Seq_1  1081  ctggcgcgagcagtgctggaaggcgtgggttatgcgctggcagatggcatggatgtcgtg  1140
             ||#|#||#|#||#|#||||#||#|#|#|#|#|#||||#|#|||||#|||#
Seq_2  1081  ctcgccgcgccgtcctcgagggcgtcggctacgccctcgccgacggcatggacgtcgtc  1140

Seq_1  1141  catgcctgcggtattaaaccgcaaagtgttacgttgattgggggcggggcgcgtagtgag  1200
             ||#|||||||#||#||#|||####|#||##|#|#|#||||#|#|####|||
Seq_2  1141  cacgcctgcggcatcaagccgcagtcggtcaccctcatcggcggcggcgcccgctcggag  1200

Seq_1  1201  tactggcgtcagatgctggcggatatcagcggtcagcagctcgattaccgtacgggggg  1260
             |||||||#||||||||#|#|#|###|#|||||||||#||||#|#|#|#
Seq_2  1201  tactggcgccagatgctcgccgacatctcgggccagcagctcgactaccgcaccggcggc  1260

Seq_1  1261  gatgtggggccagcactgggcgcagcaaggctggcgcagatcgcggcgaatccagagaaa  1320
             ||#|#||#|#||#||#||#|#||#|##|#|#||||#|#||#|#|#|||||
Seq_2  1261  gacgtcggcccggccctcggcgccgcgcctcgcccagatcgccgccaacccggagaag  1320

Seq_1  1321  tcgctcattgaattgttgccgcaactaccgttagaacagtcgcatctaccagatgcgcag  1380
             ||||||#|##|##|#||||#|#|#|#|#|||||||#|#|#|#|#|||
Seq_2  1321  tcgctcatcgagctcctcccgcagctcccgctcgagcagtcgcacctcccggacgccag  1380

Seq_1  1381  cgttatgccgcttatcagccacgacgagaaacgttccgtcgcctctatcagcaacttctg  1440
             |#|#||||#|#||||#|#||||#|#|#|#|#||||#||||||#||||#|#
Seq_2  1381  cgctacgccgcctaccagccgcgccgcgagaccttccgcgcctctaccagcagctcctc  1440

Seq_1  1441  ccattaatggcgtaa  1455
             ||##|#|||||#|||
Seq_2  1441  ccgctcatggcctaa  1455
```

FIG. 18-2

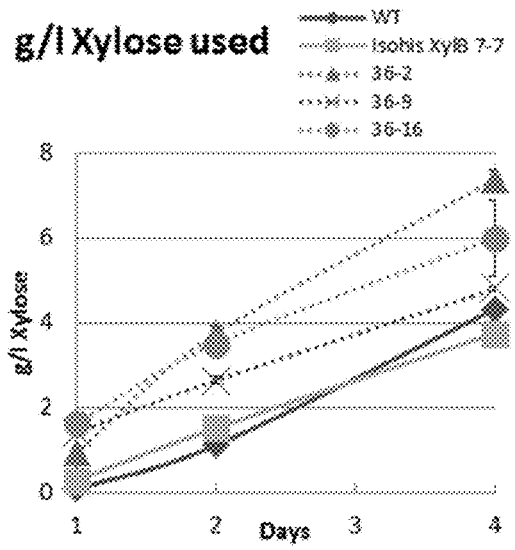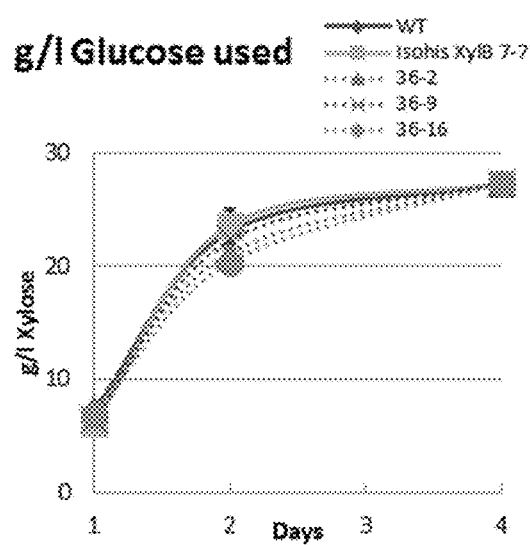
FIG. 19A          FIG. 19B
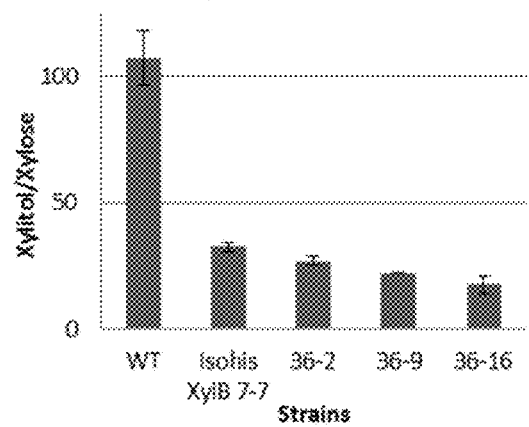
FIG. 19C

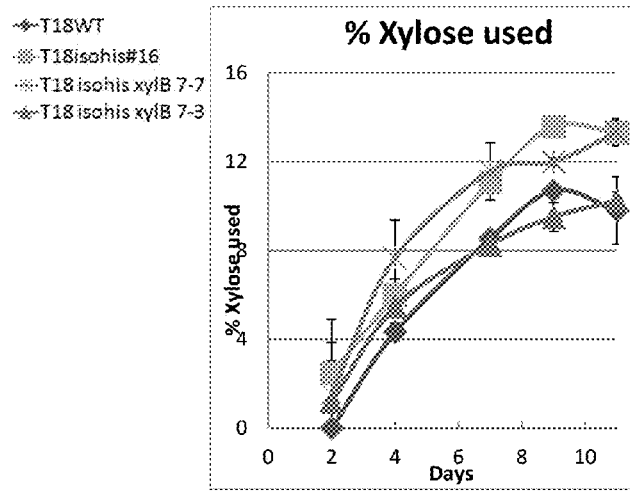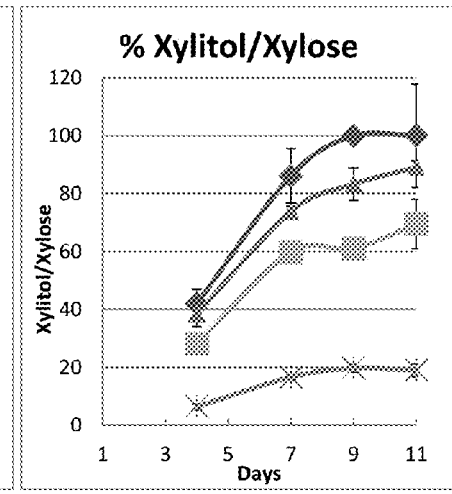
FIG. 23A                    FIG. 23B
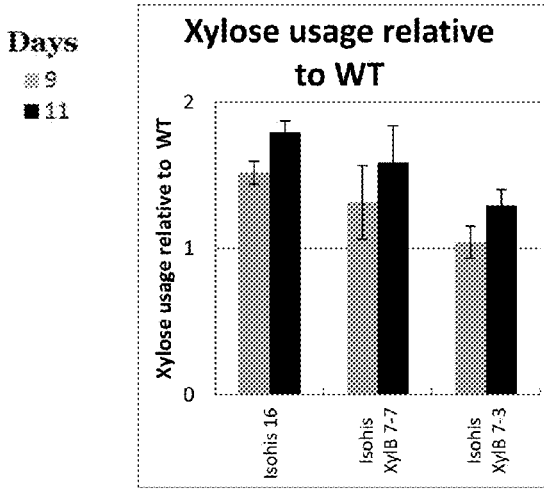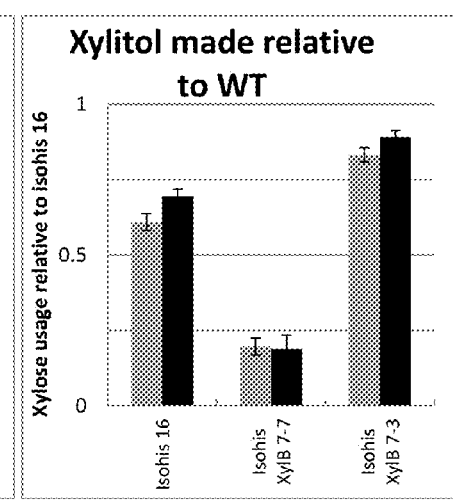
FIG. 23C                    FIG. 23D

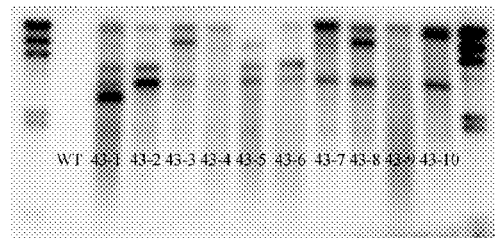
FIG. 26A
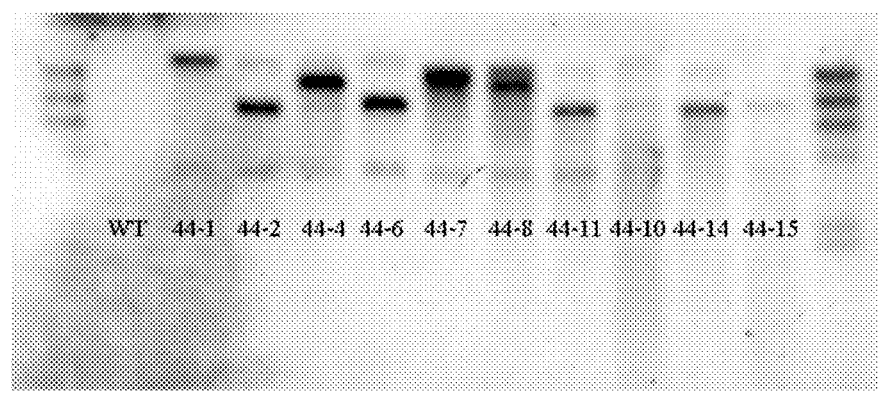
FIG. 26B
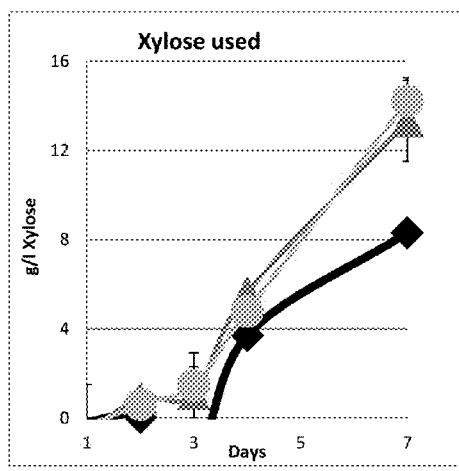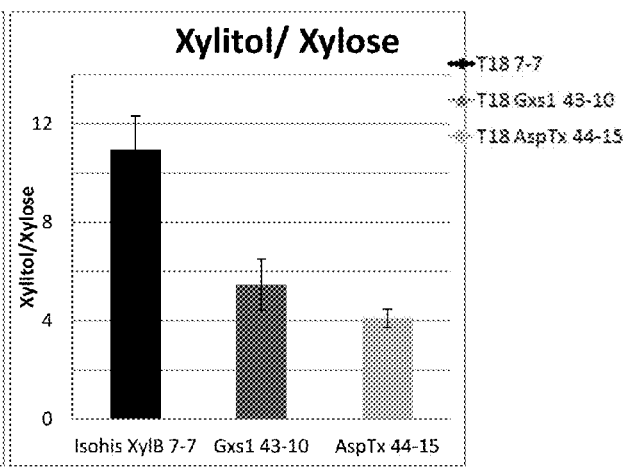
FIG. 27A          FIG. 27B

SEQUENCE LISTING

```
<160> NUMBER OF SEQ ID NOS: 30

<210> SEQ ID NO 1
<211> LENGTH: 1723
<212> TYPE: DNA
<213> ORGANISM: Thraustochytrium sp.

<400> SEQUENCE: 1
gtagtcatac gctcgtctca aagattaagc catgcatgtg taagtataag cgattatact      60
gtgagactgc gaacggctca ttatatcagt tatgatttct tcggtatttt ctttatatgg     120 ataccctgcag taattctgga attaatacat gctgagaggg cccgactgtt cgggagggcc     180
gcacttatta gagttgaagc caagtaagat ggtgagtcat gataattgag cagatcgctt     240
gtttggagcg atgaatcgtt tgagtttctg ccccatcagt tgtcgacggt agtgtattgg     300
actacggtga ctataacggg tgacggggag ttagggctcg actccggaga gggagcctga     360
gagacggcta ccacatccaa ggaaggcagc aggcgcgtaa attacccaat gtggactcca     420
cgaggtagtg acgagaaata tcaatgcggg gcgcttcgcg tcttgctatt ggaatgagag     480
caatgtaaaa ccctcatcga ggatcaactg gagggcaagt ctggtgccag cagccgcggt     540
aattccagct ccagaagcgt atgctaaagt tgttgcagtt aaaaagctcg tagttgaatt     600
tctggggcgg gagccccggt ctttgcgcga ctgcgctctg tttgccgagc ggctcctctg     660
ccatcctcgc ctctttttt agtggcgtcg ttcactgtaa ttaaagcaga gtgttccaag     720
caggtcgtat gacctggatg tttattatgg gatgatcaga tagggctcgg gtgctatttt     780
```

| | |
|---|---|
| gttggtttgc acatctgagt aatgatgaat aggaacagtt gggggtattc gtatttagga | 840 |
| gctagaggtg aaattcttgg atttccgaaa gacgaactac agcgaaggca tttaccaagc | 900 |
| atgttttcat taatcaagaa cgaaagtctg gggatcgaag atgattagat accatcgtag | 960 |
| tctagaccgt aaacgatgcc gacttgcgat tgcggggtgt ttgtattgga ccctcgcagc | 1020 |
| agcacatgag aaatcaaagt ctttgggttc cggggggagt atggtcgcaa ggctgaaact | 1080 |
| taaaggaatt gacggaaggg caccaccagg agtggagcct gcggcttaat ttgactcaac | 1140 |
| acgggaaaac ttaccaggtc cagacatagg taggattgac agattgagag ctctttcttg | 1200 |
| attctatggg tggtggtgca tggccgttct tagttggtgg agtgatttgt ctggttaatt | 1260 |
| ccgttaacga acgagacctc ggcctactaa atagcggtgg gtatggcgac atacttgcgt | 1320 |
| acgcttctta gagggacatg ttcggtatac gagcaggaag ttcgaggcaa taacaggtct | 1380 |
| gtgatgccct tagatgttct gggccgcacg cgcgctacac tgatgggttc aacgggtggt | 1440 |
| catcgttgtt cgcagcgagg tgctttgccg gaaggcatgg caaatccttt caacgcccat | 1500 |
| cgtgctgggg ctagattttt gcaattatta atctccaacg aggaattcct agtaaacgca | 1560 |
| agtcatcagc ttgcattgaa tacgtccctg ccctttgtac acaccgcccg tcgcacctac | 1620 |
| cgattgaacg gtccgatgaa accatgggat gaccttttga gcgtttgttc gcagggggg | 1680 |
| tcagaactcg ggtgaatctt attgtttaga ggaaggtgaa gtc | 1723 |

<210> SEQ ID NO 2
<211> LENGTH: 1320
<212> TYPE: DNA
<213> ORGANISM: Thraustochytrium sp.

<400> SEQUENCE: 2

| | |
|---|---|
| atggagttct tccccgaggt ggccaaggtg gagtacgccg ccccgagag ccgcgacgtc | 60 |
| ctggcgtata gatggtacaa caaggaagag gtagtgatgg ggaagaaaat gaaggagtgg | 120 |
| ctgaggttct cggtgtgctt ttggcatacc tttcgcggaa acgggtcgga cccctttggc | 180 |
| aagcccacca tcacgcaccg cttcgcaggc gacgatggtt cggacaccat ggagaacgcc | 240 |
| ctccggcgcg ttgaggcggc cttttgagctc tttgtcaagc tcggcgtgga gttctactcc | 300 |
| tttcacgacg tcgatgtggc gcctgagggc aagacgctca aggagacaaa cgagaacctg | 360 |
| gacaagatca cggaccgcat gctcgagctg aacaggaga cgggcgtcaa gctgctctgg | 420 |
| ggcactgcca acttgttctc tcatccgcga tacatgaacg gcgggtcaac aaacccggat | 480 |
| cccaaggtct ttgtgcgcgc cgccgcgcag gtgaaaaagg ccatcgacgt gacccacaaa | 540 |
| ctcggtggcg aaggctttgt gttctgggc ggtcgggagg gttacatgca cattctcaac | 600 |
| acggatatgg tccgtgaaat gaatcattac gcgaaaatgc tcaagatggc catcgcctac | 660 |
| aagaaaaaga tcggcttcgg cggcagatc ctggtcgaac ccaagccccg cgagcccatg | 720 |
| aagcaccagt atgactacga cgtgcagacc gtcattggct ttctcagaca gcacggcctg | 780 |
| gaaaacgagg tcagcctcaa cgtggagccc aatcacacgc agctcgccgg gcacgagttt | 840 |
| gagcacgatg tcgtcctcgc cgcgcagctc ggcatgctcg cagcgtcga cgccaacacg | 900 |
| ggctccgaga gcctcgggtg ggacacggac gagttcatca ccgaccaaac gcgcgccact | 960 |
| gtgctttgca aggccatcat tgagatgggt ggtttcgttc agggcggtct caactttgac | 1020 |
| gccaaggtcc gtcgggagag caccgacccg gaggacctct ttatcgctca tgtcgctccg | 1080 |
| attgacgcgc tcgccaaggg tctgcgcaac gcttcgcagc tcgttctga cggccgcatg | 1140 |
| cgcaaaatgc tccaggaccg gtacgccggc tgggatgagg gcatcggaca aagattgag | 1200 |

| | |
|---|---|
| attggggaaa cctcgcttga ggacctcgag gcccactgcc tgcaggacga cacggaacca | 1260 |
| gtcaagacgt cggccaagca ggagaaattc cttgccgttc tcaaccacta catttcctaa | 1320 |

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Met His His His His His His Gly Ser Met Ser
1               5                   10

<210> SEQ ID NO 4
<211> LENGTH: 33
<212> TYPE: DNA
<213> ORGANISM: Artificial Sequence
<220> FEATURE:
<223> OTHER INFORMATION: Synthetic Construct

<400> SEQUENCE: 4

| | |
|---|---|
| atgcaccacc accaccacca cggttccatg tcg | 33 |

<210> SEQ ID NO 5
<211> LENGTH: 1455
<212> TYPE: DNA
<213> ORGANISM: Artificial Sequence
<220> FEATURE:
<223> OTHER INFORMATION: Artificial Construct

<400> SEQUENCE: 5

| | |
|---|---|
| atgtacatcg gcatcgacct cggcacctcg ggcgtcaagg tcatcctcct caacgagcag | 60 |
| ggcgaggtcg tcgccgccca gaccgagaag ctcaccgtct cgcgcccgca cccgctctgg | 120 |
| tcggagcagg acccggagca gtggtggcag gccaccgacc gcgccatgaa ggccctcggc | 180 |
| gaccagcact cgctccagga cgtcaaggcc ctcggcatcg ccggcagat gacggcgcc | 240 |
| accctcctcg acgccagca gcgcgtcctc cgcccggcca tcctctggaa cgacggccgc | 300 |
| tgcgcccagg agtgcaccct cctcgaggcc cgcgtcccgc agtcgcgcgt catcaccggc | 360 |
| aacctcatga tgccgggctt caccgccccg aagctcctct gggtccagcg ccacgagccg | 420 |
| gagatcttcc gccagatcga caaggtcctc ctcccgaagg actacctccg cctccgcatg | 480 |
| accggcgagt cgcctcgga catgtcggac gccgccggca ccatgtggct cgacgtcgcc | 540 |
| aagcgcgact ggtcggacgt catgctccag gcctgcgacc tctcgcgcga ccagatgccg | 600 |
| gccctctacg agggctcgga gatcaccggc gccctcctcc ggaggtcgc caaggcctgg | 660 |
| ggcatggcca ccgtcccggt cgtcgccggc ggcggcgaca acgccgccgg cgccgtcggc | 720 |
| gtcggcatgg tcgacgccaa ccaggccatg ctctcgctcg gcacctcggg cgtctacttc | 780 |
| gccgtctcgg agggcttcct ctcgaagccg gagtcggccg tccactcgtt ctgccacgcc | 840 |
| ctcccgcagc gctggcacct catgtcggtc atgctctcgg ccgcctcgtg cctcgactgg | 900 |
| gccgccaagc tcaccggcct ctcgaacgtc ccggccctca tcgccgccgc ccagcaggcc | 960 |
| gacgagtcgg ccgagccggt ctggttcctc ccgtacctct cgggcgagcg caccccgcac | 1020 |
| aacaacccgc aggccaaggg cgtcttcttc ggcctcaccc accagcacgg cccgaacgag | 1080 |
| ctcgcccgcg ccgtcctcga gggcgtcggc tacgccctcg ccgacggcat ggacgtcgtc | 1140 |
| cacgcctgcg gcatcaagcc gcagtcggtc accctcatcg gcggcggcgc ccgctcggag | 1200 |

```
tactggcgcc agatgctcgc cgacatctcg ggccagcagc tcgactaccg caccggcggc    1260
gacgtcggcc cggccctcgg cgccgcccgc ctcgcccaga tcgccgccaa cccggagaag    1320
tcgctcatcg agctcctccc gcagctcccg ctcgagcagt cgcacctccc ggacgcccag    1380
cgctacgccg cctaccagcc gcgccgcgag accttccgcc gcctctacca gcagctcctc    1440
ccgctcatgg cctaa                                                     1455
```

<210> SEQ ID NO 6
<211> LENGTH: 22
<212> TYPE: PRT
<213> ORGANISM: Artificial Sequence
<220> FEATURE:
<223> OTHER INFORMATION: Synthetic Construct

<400> SEQUENCE: 6

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
gacgacgtga ccctgttcat                                                   20

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct

<400> SEQUENCE: 8
tcccggaagt tcgtggaca                                                    19

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
tgagattggg gaaacctcgc                                                   20

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct

<400> SEQUENCE: 10
tcttgactgg ttggccgtgt cg                                                22

<210> SEQ ID NO 11
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 11
cgtcctgcgc attgatcttg                                                     20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ggcgagcttc tccttgatgt                                                     20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
ggcgtcaacc acaaggagta                                                     20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
tgtcgttgat gaccttggca                                                     20

<210> SEQ ID NO 15
<211> LENGTH: 1669
<212> TYPE: DNA
<213> ORGANISM: Piromyces sp.

<400> SEQUENCE: 15
gtaaatggct aaggaatatt tcccacaaat tcaaaagatt aagttcgaag gtaaggattc         60
taagaatcca ttagccttcc actactacga tgctgaaaag gaagtcatgg gtaagaaaat        120
gaaggattgg ttacgtttcg ccatggcctg gtggcacact ctttgcgccg aaggtgctga        180
ccaattcggt ggaggtacaa agtctttccc atggaacgaa ggtactgatg ctattgaaat        240
tgccaagcaa aaggttgatg ctggtttcga aatcatgcaa aagcttggta ttccatacta        300
ctgtttccac gatgttgatc ttgtttccga aggtaactct attgaagaat acgaatccaa        360
ccttaaggct gtcgttgctt acctcaagga aaagcaaaag gaaaccggta ttaagcttct        420
ctggagtact gctaacgtct tcggtcacaa gcgttacatg aacggtgcct ccactaaccc        480
agactttgat gttgtcgccc gtgctattgt tcaaattaag aacgccatag acgccggtat        540
tgaacttggt gctgaaaact acgtcttctg gggtggtcgt gaaggttaca tgagtctcct        600
taacactgac caaaagcgtg aaaaggaaca catggccact atgcttacca tggctcgtga        660
ctacgctcgt tccaagggat tcaagggtac tttcctcatt gaaccaaagc caatggaacc        720
aaccaagcac caatacgatg ttgacactga accgcgtatt ggtttcctta aggcccacaa        780
cttagacaag gacttcaagg tcaacattga agttaaccac gctactcttg ctggtcacac        840
```

```
tttcgaacac gaacttgcct gtgctgttga tgctggtatg ctcggttcca ttgatgctaa      900
ccgtggtgac taccaaaacg gttgggatac tgatcaattc ccaattgatc aatacgaact      960
cgtccaagct tggatggaaa tcatccgtgg tggtggtttc gttactggtg gtaccaactt     1020
cgatgccaag actcgtcgta actctactga cctcgaagac atcatcattg cccacgtttc     1080
tggtatggat gctatggctc gtgctcttga aaacgctgcc aagctcctcc aagaatctcc     1140
atacaccaag atgaagaagg aacgttacgc ttccttcgac agtggtattg gtaaggactt     1200
tgaagatggt aagctcaccc tcgaacaagt ttacgaatac ggtaagaaga acggtgaacc     1260
aaagcaaact tctggtaagc aagaactcta cgaagctatt gttgccatgt accaataagt     1320
taatcgtagt taaattggta aataattgt aaaatcaata aacttgtcaa tcctccaatc      1380
aagtttaaaa gatcctatct ctgtactaat taaatatagt acaaaaaaaa atgtataaac     1440
aaaaaaagt ctaaaagacg gaagaattta atttagggaa aaaataaaaa taataataaa      1500
caatagataa atcctttata ttaggaaaat gtcccattgt attatttca tttctactaa      1560
aaaagaaagt aaataaaaca caagaggaaa ttttccctttt ttttttttt tgtaataaat     1620
tttatgcaaa tataaatata aataaaataa taaaaaaaaa aaaaaaaa                  1669
```

<210> SEQ ID NO 16  
<211> LENGTH: 395  
<212> TYPE: PRT  
<213> ORGANISM: Streptomyces lividans

<400> SEQUENCE: 16

```
Met Asn Tyr Gln Pro Thr Ser Glu Asp Arg Phe Thr Phe Gly Leu Trp
1               5                   10                  15

Thr Val Gly Trp Gln Gly Leu Asp Pro Phe Gly Asp Ala Thr Arg Glu
            20                  25                  30

Ala Leu Asp Pro Ala Glu Ser Val Arg Arg Leu Ser Gln Leu Gly Ala
        35                  40                  45

Tyr Gly Val Thr Phe His Asp Asp Glu Leu Ile Pro Phe Gly Ser Ser
    50                  55                  60

Asp Asn Glu Arg Gly Val Ala His Gly Ala Val Ala His Gln Ala
65                  70                  75                  80

Val Pro Ala Gly Ala Gly Arg Asp Arg His Glu Gly Ala Asp Gly Asp
                85                  90                  95

Asp Glu Pro Val His Ala Pro Gly Cys Ser Arg Asp Gly Ala Phe Thr
            100                 105                 110

Ala Asn Asp Arg Asp Val Arg Gly Thr Arg Cys Ala Arg Ala Ile Arg
        115                 120                 125

Asn Ile Asp Leu Ala Val Glu His Val Ala Arg Ala Ser Thr Cys Ala
    130                 135                 140

Trp Gly Gly Arg Glu Gly Ala Glu Ser Gly Ala Ala Lys Asp Val Arg
145                 150                 155                 160

Asp Ala Leu Asp Arg Met Lys Glu Ala Phe Asp Leu Leu Gly Glu Tyr
                165                 170                 175

Val Thr Glu Gln Gly Tyr Asp Leu Lys Phe Ala Ile Glu Pro Lys Pro
            180                 185                 190

Asn Glu Pro Arg Gly Asp Ile Leu Leu Pro Thr Val Gly His Ala Leu
        195                 200                 205

Ala Phe Ile Glu Arg Leu Glu Arg Pro Glu Leu Tyr Gly Val Asn Pro
    210                 215                 220
```

```
Glu Val Gly His Glu Gln Met Ala Gly Leu Asn Phe Pro His Gly Ile
225                 230                 235                 240

Ala Gln Ala Leu Trp Ala Gly Lys Leu Phe His Ile Asp Leu Asn Gly
                245                 250                 255

Gln Ser Gly Ile Lys Tyr Asp Gln Asp Leu Arg Phe Gly Ala Gly Asp
            260                 265                 270

Leu Arg Ala Ala Phe Trp Leu Val Asp Leu Leu Glu Arg Ala Gly Tyr
        275                 280                 285

Ala Gly Pro Arg His Phe Asp Phe Lys Pro Pro Arg Thr Glu Asn Phe
    290                 295                 300

Asp Ala Val Trp Pro Ser Ala Ala Gly Cys Met Arg Asn Tyr Leu Ile
305                 310                 315                 320

Leu Lys Asp Arg Ala Ala Phe Arg Ala Asp Pro Gln Val Gln Glu
                325                 330                 335

Ala Leu Ala Ala Ala Arg Leu Asp Glu Leu Ala Arg Pro Thr Ala Glu
                340                 345                 350

Asp Gly Leu Ala Ala Leu Leu Ala Asp Arg Ser Ala Tyr Asp Thr Phe
            355                 360                 365

Asp Val Asp Ala Ala Ala Ala Arg Gly Met Ala Phe Glu His Leu Asp
        370                 375                 380

Gln Leu Ala Met Asp His Leu Leu Gly Ala Arg
385                 390                 395

<210> SEQ ID NO 17
<211> LENGTH: 2040
<212> TYPE: DNA
<213> ORGANISM: Piromyces sp.

<400> SEQUENCE: 17
attatataaa ataactttaa ataaaacaat ttttatttgt ttatttaatt attcaaaaaa      60
aattaaagta aaagaaaaat aatacagtag aacaatagta ataatatcaa aatgaagact    120
gttgctggta ttgatcttgg aactcaaagt atgaaagtcg ttatttacga ctatgaaaag    180
aaagaaatta ttgaaagtgc tagctgtcca atggaattga tttccgaaag tgacggtacc    240
cgtgaacaaa ccactgaatg gtttgacaag ggtcttgaag tttgttttgg taagcttagt    300
gctgataaca aaaagactat tgaagctatt ggtatttctg gtcaattaca cggttttgtt    360
cctcttgatg ctaacggtaa ggctttatac aacatcaaac tttggtgtga tactgctacc    420
gttgaagaat gtaagattat cactgatgct gccggtggtg acaaggctgt tattgatgcc    480
cttggtaacc ttatgctcac cggttttcac gctccaaaga tcctctggct caagcgcaac    540
aagccagaag ctttcgctaa cttaaagtac attatgcttc cacacgatta cttaaactgg    600
aagcttactg gtgattacgt tatggaatac ggtgatgcct ctggtaccgc tctcttcgat    660
tctaagaacc gttgctggtc taagaagatt gcgatatca ttgacccaaa acttttagat    720
ttacttccaa agttaattga accaagcgct ccagctggta aggttaatga tgaagccgct    780
aaggcttacg gtattccagc cggtattcca gtttccgctg gtggtggtga taacatgatg    840
ggtgctgttg gtactggtac tgttgctgat ggtttcctta ccatgtctat gggtacttct    900
ggtactcttt acggttacag tgacaagcca attagtgacc cagctaatgg tttaagtggt    960
ttctgttctt ctactggtgg atggcttcca ttactttgta ctatgaactg tactgttgcc   1020
actgaattcg ttcgtaacct cttccaaatg gatattaagg aacttaatgt tgaagctgcc   1080
aagtctccat gtggtagtga aggtgtttta gttattccat tcttcaatgg tgaaagaact   1140
```

-continued

```
ccaaacttac caaacggtcg tgctagtatt actggtctta cttctgctaa caccagccgt    1200
gctaacattg ctcgtgctag tttcgaatcc gccgttttcg ctatgcgtgg tggtttagat    1260
gctttccgta agttaggttt ccaaccaaag gaaattcgtc ttattggtgg tggttctaag    1320
ctgatctctg gagacaaatt gccgctgata tcatgaacct tccaatcaga gttccacttt    1380
tagaagaagc tgctgctctt ggtggtgctg ttcaagcttt atggtgtctt aagaaccaat    1440
ctggtaagtg tgatattgtt gaactttgca aagaacacat taagattgat gaatctaaga    1500
atgctaaccc aattgccgaa aatgttgctg tttacgacaa ggcttacgat gaatactgca    1560
aggttgtaaa tactctttct ccattatatg cttaaattgc aatgtaaaa aaaaatataa    1620 tgccatataa ttgccttgtc aatacactgt tcatgttcat ataatcatag acattgaat    1680 ttacaaggtt tatacaatta atatctatta tcatattatt atacagcatt tcattttcta    1740
agattagacg aaacaattct tggttccttg caatatacaa aatttacatg aattttaga    1800 atagtctcgt atttatgccc aataatcagg aaaattacct aatgctggat tcttgttaat    1860
aaaaacaaaa taaataaatt aaataaacaa ataaaaatta taagtaaata taaatatata    1920
agtaatataa aaaaaagta aataaataaa taaataaata aaaatttttt gcaaatatat    1980
aaataaataa ataaaatata aaaataattt agcaaataaa ttaaaaaaaa aaaaaaaaaa    2040

<210> SEQ ID NO 18
<211> LENGTH: 1803
<212> TYPE: DNA
<213> ORGANISM: Saccharomyces sp.

<400> SEQUENCE: 18
atgttgtgtt cagtaattca gagacagaca agagaggttt ccaacacaat gtctttagac      60
tcatactatc ttgggtttga tctttcgacc caacaactga aatgtctcgc cattaaccag     120
gacctaaaaa ttgtccattc agaaacagtg gaatttgaaa aggatcttcc gcattatcac     180
acaaagaagg gtgtctatat acacggcgac actatcgaat gtcccgtagc catgtggtta     240
gaggctctag atctggttct ctcgaaatat cgcgaggcta aatttccatt gaacaaagtt     300
atggccgtct cagggtcctg ccagcagcac gggtctgtct actggtcctc ccaagccgaa     360
tctctgttag agcaattgaa taagaaaccg gaaaagatt tattgcacta cgtgagctct      420
gtagcatttg caaggcaaac cgccccccaat tggcaagacc acagtactgc aaagcaatgt     480
caagagtttg aagagtgcat aggtgggcct gaaaaaatgg ctcaattaac agggtccaga     540
gcccatttta gatttactgg tcctcaaatt ctgaaaattg cacaattaga accagaagct     600
tacgaaaaaa caaagaccat ttctttagtg tctaattttt tgacttctat cttagtgggc     660
catcttgttg aattagagga ggcagatgcc tgtggtatga acctttatga tatacgtgaa     720
agaaaattca gtgatgagct actacatcta attgatagtt cttctaagga taaaactatc     780
agacaaaaat taatgagagc acccatgaaa aatttgatag cgggtaccat ctgtaaaatat    840 tttattgaga agtacggttt caatacaaac tgcaaggtct ctcccatgac tggggataat     900
ttagccacta tatgttcttt acccctgcgg aagaatgacg ttctcgtttc cctaggaaca     960
agtactacag ttcttctggt caccgataag tatcaccct ctccgaacta tcatcttttc     1020
attcatccaa ctctgccaaa ccattatatg ggtatgattt gttattgtaa tggttctttg    1080
gcaagggaga ggataagaga cgagttaaac aaagaacggg aaaataatta tgagaagact    1140
aacgattgga ctcttttttaa tcaagctgtg ctagatgact cagaaagtag tgaaaatgaa    1200
ttaggtgtat attttcctct ggggggagatc gttcctagcg taaaagccat aaacaaaagg    1260
```

| | |
|---|---|
| gttatcttca atccaaaaac gggtatgatt gaaagagagg tggccaagtt caaagacaag | 1320 |
| aggcacgatg ccaaaaatat tgtagaatca caggctttaa gttgcagggt aagaatatct | 1380 |
| cccctgcttt cggattcaaa cgcaagctca aacagagac tgaacgaaga tacaatcgtg | 1440 |
| aagtttgatt acgatgaatc tccgctgcgg gactacctaa ataaaaggcc agaaaggact | 1500 |
| ttttttgtag gtggggcttc taaaaacgat gctattgtga agaagtttgc tcaagtcatt | 1560 |
| ggtgctacaa agggtaattt taggctagaa acaccaaact catgtgccct tggtggttgt | 1620 |
| tataaggcca tgtggtcatt gttatatgac tctaataaaa ttgcagttcc ttttgataaa | 1680 |
| tttctgaatg acaattttcc atggcatgta atggaaagca tatccgatgt ggataatgaa | 1740 |
| aattgggatc gctataattc caagattgtc cccttaagcg aactggaaaa gactctcatc | 1800 |
| taa | 1803 |

```
<210> SEQ ID NO 19
<211> LENGTH: 2942
<212> TYPE: DNA
<213> ORGANISM: Pichia sp.
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
```

<400> SEQUENCE: 19

| | |
|---|---|
| ttanacagtt ttccagaatc caaattttcc aaccaacnaa aaacggaccc agaaagttac | 60 |
| agattttca gagcttcatc tttntanga tttcacagct tcatcaattt cagaccatag | 120 |
| ccataatgac ttttgtagag tttccnatca ctattcccaa ccagcagcgt gtgnaaactg | 180 |
| ccatcaccta tagtgcctac ttttcggttt tcaccagtgt ggttttggc ctagttacaa | 240 |
| attcgctaga gaatgttgtg tatgcttttg gagcgcagac tgccatcacg ttagtgttga | 300 |
| ctgcattcaa ctggccgtgg ttcacgagtg ctcccggtat cgaatggctc ccggtagaat | 360 |
| tttaggatcg tatggtgact tggcgattta actgggtagc acaagggaat ttcaggaaa | 420 |
| ttttctggtt ggacattttg ggcggctgaa ctttcatggt taaaaggact aaggccagat | 480 |
| tctcgggggg agaaaaattt ctgttagttt ggaattttcc gagccccaca cattgcgatg | 540 |
| gtagattcgg tacgaaacta tataaacggt tggattccta gaaagggcca gatcagattg | 600 |
| tagstagtat atatagcata tagatccctg gaggatacccc acagacatta ctgctactaa | 660 |
| ttcataccat acttgacgta tatctgcgca tacatatcta ccccaacttt catataaaat | 720 |
| tcctagattt attgcatctt ctaatagagt catttttcag atttttcaat ttccatagaa | 780 |
| agcatacatt ttcatacagc ttctatttgt taatcgacct gataatttta ctagccatat | 840 |

```
ttcttttttt gattttttcac ttaatcgaca tataaatact cacgtagttg acactcacaa    900
tgaccactac cccatttgat gctccagata agctcttcct cgggttcgat ctttcgactc    960
agcagttgaa gatcatcgtc accgatgaaa acctcgctgc tctcaaaacc tacaatgtcg   1020
agttcgatag catcaacagc tctgtccaga agggtgtcat tgctatcaac gacgaaatca   1080
gcaagggtgc cattatttcc cccgtttaca tgtggttgga tgcccttgac catgtttttg   1140
aagacatgaa gaaggacgga ttccccttca caaggttgt tggtatttcc ggttcttgtc    1200
aacagcacgg ttcggtatac tggtctagaa cggccgagaa ggtcttgtcc gaattggacg   1260
ctgaatcttc gttatcgagc cagatgagat ctgctttcac cttcaagcac gctccaaact   1320
ggcaggatca ctctaccggt aaagagcttg aagagttcga aagagtgatt ggtgctgatg   1380
ccttggctga tatctctggt tccagagccc attacagatt cacagggctc cagattagaa   1440
agttgtctac cagattcaag cccgaaaagt acaacagaac tgctcgtatc tctttagttt   1500
cgtcatttgt tgccagtgtg ttgcttggta gaatcacctc cattgaagaa gccgatgctt   1560
gtggaatgaa cttgtacgat atcgaaaagc gcgagttcaa cgaagagctc ttggccatcg   1620
ctgctggtgt ccaccctgag ttggatggta gaacaagga cggtgaaatt tacagagctg   1680
gtatcaatga gttgaagaga aagttgggtc tgtcaaacc tataacatac gaaagcgaag   1740
gtgacattgc ctcttacttt gtcaccagat acggcttcaa ccccgactgt aaaatctact   1800
cgttcaccgg agacaatttg gccacgatta tctcgttgcc tttggctcca aatgatgctt   1860
tgatctcatt gggtacttct actacagttt taattatcac caagaactac gctccttctt   1920
ctcaataccca tttgttttaaa catccaacca tgcctgacca ctacatgggc atgatctgct   1980
actgtaacgg ttccttggcc agagaaaagg ttagagacga agtcaacgaa aagttcaatg   2040
tagaagacaa gaagtcgtgg gacaagttca atgaaatctt ggacaaatcc acagacttca   2100
acaacaagtt gggtatttac ttcccacttg gcgaaattgt ccctaatgcc gctgctcaga   2160
tcaagagatc ggtgttgaac agcaagaacg aaattgtaga cgttgagttg ggcgacaaga   2220
actggcaacc tgaagatgat gtttcttcaa ttgtagaatc acagactttg tcttgtagat   2280
tgagaactgg tccaatgttg agcaagagtg gagattcttc tgcttccagc tctgcctcac   2340
ctcaaccaga aggtgatggt acagatttgc acaaggtcta ccaagacttg gttaaaaagt   2400
ttggtgactt gttcactgat ggaaagaagc aaacctttga gtctttgacc gccagaccta   2460
accgttgtta ctacgtcggt ggtgcttcca acaacggcag cattatccsc aagatgggtt   2520
ccatcttggc tcccgtcaac ggaaactaca aggttgacat tcctaacgcc tgtgcattgg   2580
gtggtgctta caaggccagt tggagttacg agtgtgaagc caagaaggaa tggatcggat   2640
acgatcagta tatcaacaga ttgtttgaag taagtgacga gatgaatctg ttcgaagtca   2700
aggataaatg gctcgaatat gccaacgggg ttggaatgtt ggccaagatg gaaagtgaat   2760
tgaaacacta aaatccataa tagcttgtat agaggtatag aaaaagagaa cgttatagag   2820
taaagacaat gtagcatata tgtgcgaata tcacgataga cgttatacag aagattactt   2880
tcacatcatt ttgaaaatat cttgatatgt tcatatttca ttcgcctcta gcatttttca   2940
ga                                                                  2942
```

<210> SEQ ID NO 20
<211> LENGTH: 1455
<212> TYPE: DNA
<213> ORGANISM: E. coli

<400> SEQUENCE: 20

```
atgtatatcg gbatagatct tggcacctcg ggcgtaaaag ttattttgct caacgagcag      60
ggtgaggtgg ttgctgcgca acggaaaag ctgaccgttt cgcgcccgca tccactctgg     120
tcggaacaag acccggaaca gtggtggcag gcaactgatc gcgcaatgaa agctctgggc    180
gatcagcatt ctctgcagga cgttaaagca ttgggtattg ccggccagat gcacggagca    240
accttgctgg atgctcagca acgggtgtta cgccctgcca ttttgtggaa cgacgggcgc    300
tgtgcgcaag agtgcacttt gctggaagcg cgagttccgc aatcgcgggt gattaccggc    360
aacctgatga tgcccggatt tactgcgcct aaattgctat gggttcagcg gcatgagccg    420
gagatattcc gtcaaatcga caaagtatta ttaccgaaag attacttgcg tctgcgtatg    480
acggggagt tgccagcga tatgtctgac gcagctggca ccatgtggct ggatgtcgca      540
aagcgtgact ggagtgacgt catgctgcag gcttgcgact tatctcgtga ccagatgccc    600
gcattatacg aaggcagcga aattactggt gctttgttac ctgaagttgc gaaagcgtgg    660
ggtatggcga cggtgccagt tgtcgcaggc ggtggcgaca atgcagctgg tgcagttggt    720
gtgggaatgg ttgatgctaa tcaggcaatg ttatcgctgg ggacgtcggg ggtctatttt    780
gctgtcagcg aagggttctt aagcaagcca gaaagcgccg tacatagctt ttgccatgcg    840
ctaccgcaac gttggcattt aatgtctgtg atgctgagtg cagcgtcgtg tctggattgg    900
gccgcgaaat taaccggcct gagcaatgtc ccagctttaa tcgctgcagc tcaacaggct    960
gatgaaagtg ccgagccagt ttggtttctg ccttatcttt ccggcgagcg tacgccacac   1020
aataatcccc aggcgaaggg ggttttcttt ggtttgactc atcaacatgg ccccaatgaa   1080
ctggcgcgag cagtgctgga aggcgtgggt tatgcgctgg cagatggcat ggatgtcgtg   1140
catgcctgcg gtattaaacc gcaaagtgtt acgttgattg ggggcggggc gcgtagtgag   1200
tactggcgtc agatgctggc ggatatcagc ggtcagcagc tcgattaccg tacggggggg   1260
gatgtggggc cagcactggg cgcagcaagg ctggcgcaga tcgcggcgaa tccagagaaa   1320
tcgctcattg aattgttgcc gcaactaccg ttagaacagt cgcatctacc agatgcgcag   1380
cgttatgccg cttatcagcc acgacgagaa acgttccgtc gcctctatca gcaacttctg   1440
ccattaatgg cgtaa                                                    1455
```

<210> SEQ ID NO 21
<211> LENGTH: 1623
<212> TYPE: DNA
<213> ORGANISM: Aspergillus sp.

<400> SEQUENCE: 21

```
atggctatcg gcaatctta cttcattgcg gccatcgccg tcgtcggcgg tggtctgttc      60
ggtttcgata tctcgtcgat gtcggccatc atcgagaccg atgcctatct ctgttacttc    120
aaccaggctc ctgtcactta cgatgatgat ggcaagaggg tctgtcaggg ccccagcgcg    180
agtgtgcagg gtggtatcac cgcctccatg gctggtggtt cctggttggg ctcgttgatc    240
tcgggtttca tctcggacag gcttggtcgt cgtactgcca ttcagatcgg ttccatcatc    300
tggtgcattg gatccatcat tgtctgtgcc tcccagaaca ttcccatgct gatcgtcggt    360
cgtatcatca acggtctgag tgtgggtatc tgctccgctc aggtgccagt gtatatttcg    420
gagattgctc ctccaaccaa gcgtggtcgt gtcgtcggtc tgcaacaatg ggctattacc    480
tggggtatcc tgatcatgtt ctacgtctcc tatggatgca gcttcatcaa gggtacggcg    540
gccttccgga ttccctgggg tctgcagatg atccctgccg tgctattgtt cctgggtatg    600
```

```
atgctcctgc ctgagtcacc ccgctggctg gcacgcaagg accgatggga ggagtgccac      660
gctgttttga ccctcgtcca cggtcaggga gacccgagct ctccctttgt gcagcgtgaa      720
tatgaagaga tcaagagcat gtgcgagttt gagcgccaaa acgcggatgt ctcctacctc      780
gagctgttca agcccaacat gcttaaccgt acccatgtgg gtgttttcgt tcagatctgg      840
tctcagttga ctggaatgaa cgtcatgatg tactacatca cctacgtctt tgccatggcc      900
ggcttgaaag gtaacaacaa cttgatctcc tccagtatcc agtacgtgat caacgtgtgc      960
atgactgtgc cggctctggt gtggggtgat cagtggggcc gtcgcccgac cttcttgatc     1020
ggttccctct tcatgatgat ctggatgtac attaatgctg gtctgatggc cagctacggt     1080
catcccgcgc cgcccggcgg tctcaacaac gtggaagccg agtcctgggt catccacggc     1140
gcgcccagca aggctgtcat tgccagtacc tacctcttcg tagcctcata cgccatctcc     1200
ttcggccccg ccagctgggt gtaccgcgcc gaactcttcc ctctgcgtgt gcgcggcaag     1260
gctaccgccc tctgcacttc agccaactgg gccttcaact tcgccctcag ctattttgtc     1320
cccccggcat ttgtcaacat ccagtggaag gtctacatct tcttcggtgt cttctgtact     1380
gccatgttct tgcacatttt cttcttcttt cccgagacca cgggtaagac cctggaagag     1440
gtcgaggcca tcttcactga tcccaatggt attccgtaca tcggtactcc cgcctggaag     1500
acaaagaacg agtactcgcg cggtgcacac attgaggagg ttggctttga agatgagaag     1560
aaggttgctg gtgggcagac tatccaccag gaggtcacgg ctactccgga taagattgct     1620
tga                                                                    1623

<210> SEQ ID NO 22
<211> LENGTH: 1644
<212> TYPE: DNA
<213> ORGANISM: Candida sp.

<400> SEQUENCE: 22
atgtcacaag attcgcattc ttctggtgcc gctacaccag tcaatggttc catccttgaa       60
aaggaaaaag aagactctcc agttcttcaa gttgatgccc acaaaaggg tttcaaggac      120
tacattgtca tttctatctt ctgttttatg gttgccttcg gtggtttcgt cttcggtttc      180
gacactggta ccatttccgg tttcgtgaac atgtctgact taaagacag attcggtcaa      240
caccacgctg atggtactcc ttacttgtcc gacgttagag ttggtttgat gatttctatt      300
ttcaacgttg gttgcgctgt cggtggtatt ttcctctgca aggtcgctga tgtctggggt      360
agaagaattg tcttatgtt ctccatggct gtctacgttg ttggtattat tattcagatc      420
tcttcatcca ccaagtggta ccagttcttc attggtcgtc ttattgctgg tttggctgtt      480
ggtaccgttt ctgtcgtttc ccacttttc atctctgagg tttctccaaa gcaaattaga      540
ggtactttag tgtgctgctt ccagttgtgt atcaccttgg gtatcttctt gggttactgt      600
actacttacg gtactaagac ctacactgac tctagacagt ggagaattcc tttgggtttg      660
tgtttcgctt gggctatctt gttggttgtc ggtatgttga acatgccaga gtctccaaga      720
tacttggttg agaagcacag aattgatgag gccaagagat ccattgccag atccaacaag      780
atccctgagg aggacccatt cgtctacact gaggttcagc ttattcaggc cggtattgag      840
agagaagctt ggctggtca ggcatcttgg aaggagttga tcactggtaa gccaaagatc      900
ttcagaagag ttatcatggg tattatgctt cagtccttgc aacagttgac cggtgacaac      960
tacttcttct actacggtac taccattttc caggctgtcg gtttgaagga ttctttccag     1020
acttctatca ttttgggtat tgtcaactttt gcttccacct tcgttggtat ctatgtcatt     1080
```

| | |
|---|---|
| gagagattgg gtagaagatt gtgtcttttg accggttccg ctgctatgtt catctgtttc | 1140 |
| atcatctact ctttgattgg tactcagcac ttgtacaagc aaggttactc caacgagacc | 1200 |
| tccaacactt acaaggcttc tggtaacgct atgatcttca tcacttgtct ttacattttc | 1260 |
| ttctttgctt ctacctgggc tggtggtgtt tactgtatca tttccgagtc ctacccattg | 1320 |
| agaattagat ccaaggccat gtctattgct accgctgcta actggttgtg gggtttcttg | 1380 |
| atttccttct tcactccatt catcaccagt gccatccact tctactacgg tttcgttttc | 1440 |
| actggttgtt tggcttttctc tttcttctac gtctacttct tcgtctacga aaccaagggt | 1500 |
| ctttctttgg aggaggttga tgagatgtac gcttccggtg ttcttccact caagtctgcc | 1560 |
| agctgggttc caccaaatct tgagcacatg gctcactctg ccggttacgc tggtgctgac | 1620 |
| aaggccaccg acgaacaggt ttaa | 1644 |

<210> SEQ ID NO 23
<211> LENGTH: 1569
<212> TYPE: DNA
<213> ORGANISM: Candida sp.

<400> SEQUENCE: 23

| | |
|---|---|
| atgggtttgg aggacaatag aatggttaag cgtttcgtca acgttggcga aagaaggct | 60 |
| ggctctactg ccatggccat catcgtcggt cttttgctg cttctggtgg tgtccttttc | 120 |
| ggatacgata ctggtactat ttctggtgtg atgaccatgg actacgttct gctcgttac | 180 |
| ccttccaaca agcactcttt tactgctgat gaatcttctt tgattgtttc tatcttgtct | 240 |
| gttggtactt tctttggtgc actttgtgct ccattcctta cgacacccct cggtagacgt | 300 |
| tggtgtctta ttctttctgc tcttattgtc ttcaacattg gtgctatctt gcaggtcatc | 360 |
| tctactgcca ttccattgct ttgtgctggt agagttattg caggttttgg tgtcggtttg | 420 |
| atttctgcta ctattccatt gtaccaatct gagactgctc caaagtggat cagaggtgcc | 480 |
| attgtctctt gttaccagtg ggctattacc attggtcttt tcttggcctc ttgtgtcaac | 540 |
| aagggtactg agcacatgac taactctgga tcttacagaa ttccacttgc tattcaatgt | 600 |
| ctttggggtc ttatcttggg tatcggtatg atcttcttgc cagagactcc aagattctgg | 660 |
| atctccaagg gtaaccagga gaaggctgct gagtctttgg ccagattgag aaagcttcca | 720 |
| attgaccacc cagactctct cgaggaatta agagacatca ctgctgctta cgagttcgag | 780 |
| actgtgtacg gtaagtcctc ttggagccag gtgttctctc acaagaacca ccagttgaag | 840 |
| agattgttca ctggtgtggc tatccaggct ttccagcaat tgaccggtgt taacttcatt | 900 |
| ttctactacg gtactacctt cttcaagaga gctggtgtta acggtttcac tatctccttg | 960 |
| gccactaaca ttgtcaatgt cggttctact attccaggta ttcttttgat ggaagtcctc | 1020 |
| ggtagaagaa acatgttgat gggtggtgct actggtatgt ctctttctca attgatcgtt | 1080 |
| gccattgttg gtgttgctac ctcggaaaac aacaagtctt cccagtccgt ccttgttgct | 1140 |
| ttctcctgta ttttcattgc cttcttcgct gccacctggg gtccatgtgc ttgggttgtt | 1200 |
| gttggtgagt gttcccatt gagaaccaga gctaagtctg tctccttgtg tactgcttcc | 1260 |
| aactggttgt ggaactgggg tattgcttac gctactccat acatggtgga tgaagacaag | 1320 |
| ggtaacttgg gttccaatgt gttcttcatc tggggtggtt tcaacttggc ttgtgttttc | 1380 |
| ttcgcttggt acttcatcta cgagaccaag ggtcttcctt tggagcaggt cgacgagttg | 1440 |
| tacgagcatg tcagcaaggc ttggaagtct aagggcttcg ttccatctaa gcactctttc | 1500 |

```
agagagcagg tggaccagca aatggactcc aaaactgaag ctattatgtc tgaagaagct    1560
tctgtttaa                                                            1569

<210> SEQ ID NO 24
<211> LENGTH: 1662
<212> TYPE: DNA
<213> ORGANISM: Pichia sp.

<400> SEQUENCE: 24
atgtctgtag atgaaaatca attggagaat ggacaacttc tatcctccga aaatgaggca      60
tcatcacctt ttaaagagtc tatcccttct cgctcttccc tctacttaat agctcttaca     120
gtttcacttt tgggagttca attgacttgg tcggttgaac ttggttatgg tacaccgtat     180
ttattctcac ttggtcttcg taaagaatgg acttcaatta tatggattgc cggtcctttg     240
actggaatat taattcagcc aattgctggt atattgtccg accgggttaa ttcaagaata     300
ggtcggcgga gaccgttcat gctctgtgct agtttgttag gaacattcag cttattcctt     360
atgggctggg cccctgatat ttgcctcttt atatttagca atgaggttct aatgaaacgt     420
gttactatcg ttttggctac gattagcatt tatttgcttg acgtggccgt caatgtcgta     480
atggctagca ctcgatcttt aattgttgat tcagtccgtt cagatcaaca gcatgaagca     540
aattcctggg ctggaagaat gataggtgta ggcaatgtgc ttgggtactt actaggctat     600
ttacctctat atcgcatctt ctcctttctc aatttcacac agttacaggt gttttgcgta     660
cttgcctcca tttccttggt actcacagtt accatcacaa caatatttgt gagtgaaagg     720
agattcccac cagttgaaca cgagaaatcg gttgctggag aaatctttga attttttaca     780
actatgcgac aaagtattac cgcacttcca tttacattaa aaagaatttg ttttgttcaa     840
ttttttgcat actttggatg gtttccattt ttgtttttata ttactaccta tgtgggtatt     900
ttatatttac gccatgctcc taaaggccat gaagaagatt gggacatggc gactcgtcaa     960
gggtcgttcg cattactgct ttttgctatc atttctcttg ccgcaaatac agcacttcca    1020
ttgttgctcg aggacacgga ggatgatgag gaggacgaat cgagtgatgc atctaataat    1080
gaatacaaca ttcaagaaag aaacgatctc ggaaatataa gaactggtac taatacaccc    1140
cgtcttggta atttgagcga acaacttctt ttccgttcgg aaaatgagcc ctcacgacgc    1200
aggcttttac cgtctagtag atcaattatg acaacgatat cctccaaggt acaaatcaaa    1260
ggacttactc ttcctattct gtggttgagc tcccatgtcc ttttggtgt tgtatgttg     1320 agcacgatat tcttgcaaac atcatggcaa gcgcaggcaa tggtagctat ctgtggactg    1380
tcctgggcat gtactctatg gattccatat tcgctatttt cttcagaaat agggaagctt    1440
ggattacgag aaagcagtgg caaaatgatt ggtgttcaca atgtatttat atctgccccc    1500
caagtgttga gcaccatcat tgccaccatt gtatttattc aatcggaggg cagtcatcga    1560
gacatcgccg acaatagtat agcatgggtg ttgagaattg gaggtatatc tgcatttcta    1620
gccgcgtacc aatgccggca tcttttgccc atcaacttt ga                      1662

<210> SEQ ID NO 25
<211> LENGTH: 490
<212> TYPE: DNA
<213> ORGANISM: Thraustochytrium sp.

<400> SEQUENCE: 25
cgcggcttcc cgtctccaag cttcgtctcg gtagagattc tatcttcgcc cggcagcccg      60
ccgccgtccg gcaagtgtag aacggcagaa agcccacttg cacggaacgc ccgacaagtt     120
```

| | |
|---|---|
| gacgaaagcg gcccgcaagt gcggcagccc ggctggtttt tcctcgcggc gaggccaaac | 180 |
| cgccaacgcc accaagccag acaccaggta tgtgccgcac gcgccgccgc acgcgagccc | 240 |
| cgaggatgcc ccgtacgcgc tgacgccttt ctccgccccg cccgcgagaa gacgcgctcc | 300 |
| ggcaacggcg ggagccgagc gaacgggcga ggattgatcg agtagctgca ggttgagaaa | 360 |
| aaaggaaaac cgccgagatg gacaacggct ggatggacga aagacgcac gaggacgcga | 420 |
| ggactgacga tgatcacgtg cgcaggaaga cttgaaaaga agcaaggaag gtagaaaaaa | 480 |
| aagaagaaat | 490 |

```
<210> SEQ ID NO 26
<211> LENGTH: 1004
<212> TYPE: DNA
<213> ORGANISM: Thraustochytrium sp.

<400> SEQUENCE: 26
```

| | |
|---|---|
| ggcctgtctc ccttggccat ccattgcgct gcggaagcat tggattgcga actgcgtcgg | 60 |
| ccagatcgct tggtttccca acatgagacg cgctctgtcg gcaagaccat ttccgccccc | 120 |
| ggctttgctc acaaccaact cgtagtagat tttgtaaaga acactgcacg tctgactgct | 180 |
| cccagcccgc acgcattgcg cttggcagcc tcggtcccaa accgtcacgg tcgctgcccg | 240 |
| gtccacggga aaaataact tttgtccgcg agcggccgtt caaggcgcag ccgcgagcgt | 300 |
| gccaaccgtc cgtcccgcat tcttttccca atgttggatt cattcattct tgccaggcca | 360 |
| gatcatctgt gcctccctcg cgtgcccttc cttagcgtgc gcagatctct tcttcccaga | 420 |
| gcccgcgcgg cgcttcgtgg agtcggcgtc catgtcatgc gcgcgcggcg tcttgacccc | 480 |
| ctcggcccct ttggttcgcg gctgcgcaac gagccgtttc acgccattgc gaccaaccgc | 540 |
| gcgctaaaat cggattggcc gttgcacgcc gattttgcag cacctctggg ctgtgaggga | 600 |
| cgaccgtcca cttttacccg cacagagtgg actttcaccc cctcactcca ctgaagccaa | 660 |
| cttttcgccg tcttcccaac ccaaagttta tgctagccct catgccgcaa cggacgtcac | 720 |
| ccccatttcc actggcgacg tggggacctg ggcgcaataa ggcgcgagaa ggaaattacg | 780 |
| acggcacact ggggccagaa gagggcacta ggagcggcaa cccactgccg cggcacagcg | 840 |
| gtttggcgcg gggatcaaag caaaacccgg ctcatccaga gcaaacccga atcagccttc | 900 |
| agacggtcgt gcctaacaac acgccgttct accccgcctt ccttgcgtcc ctcgcctccc | 960 |
| ccgagcccaa gtcttccgcc cgctcctaac gccaaccaag caag | 1004 |

```
<210> SEQ ID NO 27
<211> LENGTH: 590
<212> TYPE: DNA
<213> ORGANISM: Thraustochytrium sp.

<400> SEQUENCE: 27
```

| | |
|---|---|
| atgcattcgc atggctccgc accaccacac accaccgccc ctcttctttc cttgctcact | 60 |
| cgatccatag ccacttacct gccccttccc tctaccactg ccacgtgcgg cgtatgagcg | 120 |
| cgcttgcacc cgcaaccttc tctctagttg ttcacaatta cacccgctat caatactcac | 180 |
| gcattcatct tccccttttt ttctacttta cgtaccggtg ctcacttact tacacctgcc | 240 |
| cgccttgttc attcattctt ctcgatgaca acggcaggct ctgcttgcgg cgcgcgcacg | 300 |
| catcccttac tccgccgcgc accgacaagc ctgcgcaaaa aacaaaaaaa acttatcttc | 360 |
| gctcgcggct ccgatgtcgc ggcggcgtac gagaccgcgc cgagttccgc ccgccatgcg | 420 |
| atcgagagtc tctctcgtag gagcgggacc gcgagcgacc tcggtgcctc cgatagccag | 480 |

| ctgggcttct agaccggctg ggggaccgcc cgcggcgtac ctctgcgctt cggtggccct | 540 |
| taaaaggctg atcgtggaaa aggtcgctct ccagtctgcg gtttagcggc | 590 |

<210> SEQ ID NO 28
<211> LENGTH: 640
<212> TYPE: DNA
<213> ORGANISM: Thraustochytrium sp.

<400> SEQUENCE: 28

| gcgccttcag gcaggctgat ccctactgtg ggggctctga cggacggccg gtctttgtac | 60 |
| gtaaacaggc gcttcttcgc ggcccgccga ggggggcggc aacgagccgg gtggcgtggc | 120 |
| acggacaagg caagagcctt tccatcccgc ataaagtgat gcaccatttt gaccttgttg | 180 |
| atcgttttg tgtgtttaga gcggccccgt gcgggtaggc gaagtgcgct tctgagcaag | 240 |
| gaagagagag gtgcagcttc ttcttgatca gtgtggtaat cttcaacggc cacgctcgct | 300 |
| tattcgatac ctgtaaagct accggtgcac ccgtgcaagt tgggcaccac gtagttgtac | 360 |
| tggtgaatcc aaatgttagc cgctagcttg gtgccctttt cgacaggaag ggcttggtga | 420 |
| aaagccatgc tgtcgatctc ccttgggtcc tcgttcgtga cgctaggcca gagaatagct | 480 |
| gtgtgccgcg cagtcgaagc cagcgcgcgc gcgtcgggc cgagcataga gttagcaatt | 540 |
| cagttgtttc gggctcttga tgaggccgcc agagagcgaa gaaggatgaa cttaccagat | 600 |
| ccgcgctccg gtgtattggt gatgggcggc ttggtctccg | 640 |

<210> SEQ ID NO 29
<211> LENGTH: 372
<212> TYPE: DNA
<213> ORGANISM: Artificial Sequence
<220> FEATURE:
<223> OTHER INFORMATION: Synthetic Construct

<400> SEQUENCE: 29

| atggccaagc tcacctcggc cgtcccggtg ctcaccgcgc gcgacgtcgc cggcgcggtc | 60 |
| gagttctgga ccgaccggct cgggttctcc cgggacttcg tggaggacga cttcgccggc | 120 |
| gtggtccggg acgacgtgac cctgttcatc agcgcggtcc aggaccaggt ggtgccggac | 180 |
| aacaccctgg cctgggtgtg ggtgcgcggc ctggacgagc tgtacgccga gtggtcggag | 240 |
| gtcgtgtcca cgaacttccg ggacgcctcc gggccggcca tgaccgagat cggcgagcag | 300 |
| ccgtggggc gggagttcgc cctgcgcgac ccggccggca actgcgtgca cttcgtggcc | 360 |
| gaggagcagg ac | 372 |

<210> SEQ ID NO 30
<211> LENGTH: 1017
<212> TYPE: DNA
<213> ORGANISM: Thraustochytrium sp.

<400> SEQUENCE: 30

| gcgttgtttc ggcacgcgca attgccggga tgggaatgtg cattggtgca cgggattgct | 60 |
| gcgtcggccg ggccgtctcc caacatgaga cgcgctcggc aggaccgctt ccggttggca | 120 |
| taacgtcgtt ttttcccctgc tgtcccagct cgcgctttcg agacgaagct atctgtacta | 180 |
| ccctctctac tcgcgatcac tcgctcgcaa ggaaaatgga agttaacgaa aggtcaatca | 240 |
| ttttttgcgc tctgcattca tttgctctct tcttgttgtt tgtggaacca aacggtcaga | 300 |
| cgcgtggatc gcttttgtta ggcactcggg aacggctgtc cctttaagca ctcaaccgaa | 360 |
| cagtcgggcc acttggtctg caacagcgag accaacttgg gtgcatggcg gcggctcatc | 420 |

-continued

```
ttccactgcc actccatggg caggtcgtga aaggagagcc acagcgagta gcccgcctgc      480
tggcggctct gtccgcacga ctggcacaca gacgtcccgg cgtcgttctg gccaaagcac      540
atggtctgga agcgggtccg gtaacaagag gcgcaacgcc aaggctcgct cgaggccggc      600
tcgttgtccg cgttgagcgt caaaatcacg ggggcggca cgcccgcagg gcgctcgggc       660
cccgtgatcg acggatcgtc gatagcgagc acgacctcgt aacgccaggc gcgaaaatcg      720
ttgggcttgg cagccttgtc gtcaggatgc gcctgcacaa tgtcctcgac ctcgccaggc      780
actggtttga agtacgcctc cttgtgctcc tccggggccg cctctgcctc cttgtcgccg      840
tggatctcga gttgggccat gcggggaccg gccggcggca gaccgttaaa atgccagagg      900
tgcagcggtg gcttgtacga gtcgagggcg tggtcgcaga agagtagcgt aaaatggtca      960
ccgccgtgca ggatccatac agggtgcccc ggcgtcttga ggcagtcgtg tacagga        1017
```

ENHANCING MICROBIAL METABOLISM OF C5 ORGANIC CARBON

CROSS-REFERENCE TO RELATED APPLICATIONS

This application claims the benefit of priority to U.S. Provisional Application No. 62/191,983, filed Jul. 13, 2015, and U.S. Provisional Application No. 62/354,444, filed Jun. 24, 2016, which are incorporated by reference herein in their entireties.

BACKGROUND OF THE INVENTION

Heterotrophic fermentation of microorganisms is an efficient way of generating high value oil and biomass products. Under certain cultivation conditions, microorganisms synthesize intracellular oil, which can be extracted and used to produce fuel (e.g., biodiesel, bio-jetfuel, and the like) and nutritional lipids (e.g., polyunsaturated fatty acids such as DHA, EPA, and DPA). The biomass of some microorganisms is of great nutritional value due to high polyunsaturated fatty acid (PUFA) and protein content, and can be used as a nutritional supplement for animal feed. Thraustochytrids are eukaryotic, single-cell, microorganisms which can be used in such fermentation processes to produce lipids. Heterotrophic fermentations with Thraustochytrids convert organic carbon provided in the growth medium to lipids, which are harvested from the biomass at the end of the fermentation process. However, existing microorganism fermentations use mainly expensive carbohydrates, such as glucose, as the carbon source.

BRIEF SUMMARY OF THE INVENTION

Provided herein are recombinant microorganisms having two or more copies of a nucleic acid sequence encoding xylose isomerase, wherein the nucleic acid encoding the xylose isomerase is an exogenous nucleic acid. Optionally, the recombinant microorganisms include at least one nucleic acid sequence encoding a xylulose kinase and/or at least one nucleic acid sequence encoding a xylose transporter. The provided recombinant microorganisms are capable of growing on xylose as a carbon source.

BRIEF DESCRIPTION OF THE DRAWINGS

FIG. 18 is a graph showing the alignment of the xylB sequence from E. coli (SEQ ID NO:20) with the codon optimized version of E. coli xylB (SEQ ID NO:5).
FIGS. 19A, 19B, and 19C are graphs showing xylose usage (FIG. 19A), glucose usage (FIG. 19B) and percent xylitol made (FIG. 19C) in strains comprising xylose isomerase, xylulose kinase and the sugar transporter Gxs1. WT is wild-type; IsoHis XylB "7-7" contains the xylose isomerase and xylB sequences, 36-2, 36-9 and 36-16 are transformants containing Gxs1, xylose isomerase and the xylB sequences (xylulose kinase).
FIGS. 23A and 23B are graphs showing xylose use and decreased xylitol production in a T18B strain engineered with a xylose isomerase "16" (squares) and strains engineered to express a xylose isomerase and xylulose kinase "7-7" (x) and "7-3" (triangles).
FIGS. 23C (xylose) and 23D (xylitol production) show the same data relative to wild type (diamonds) at 9 (gray) and 11 (black) days.

FIG. 26A is an image of a Southern blot to probe the Gxs1 gene within "7-7" T18B strains engineered with the xylose transporter Gxs1. FIG. 26B is an image of a Southern blot to probe the AspTx gene within "7-7" T18B strains engineered with the xylose transporter AspTx.

FIG. 27A is a graph showing the use of xylose in T18 strains engineered with a xylose isomerase, a xylulose kinase and either the Gxs1 transporter (triangles) or AspTx transporter (circles). Strain "7-7" is represented by diamonds. FIG. 27B is a bar graph of the ratio of xylitol production versus xylose use for each of the 3 modified strains.

DETAILED DESCRIPTION OF THE INVENTION

Figure 1:
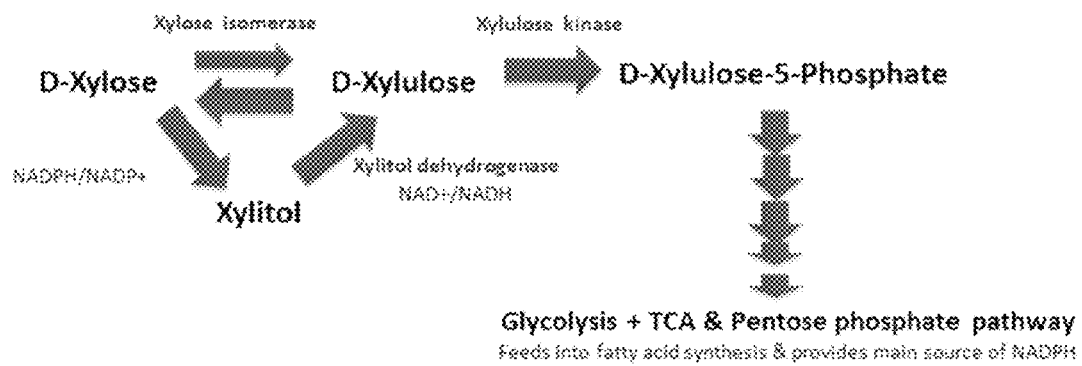
FIG. 1 is a schematic of the xylose metabolism pathway.
Figure 2:
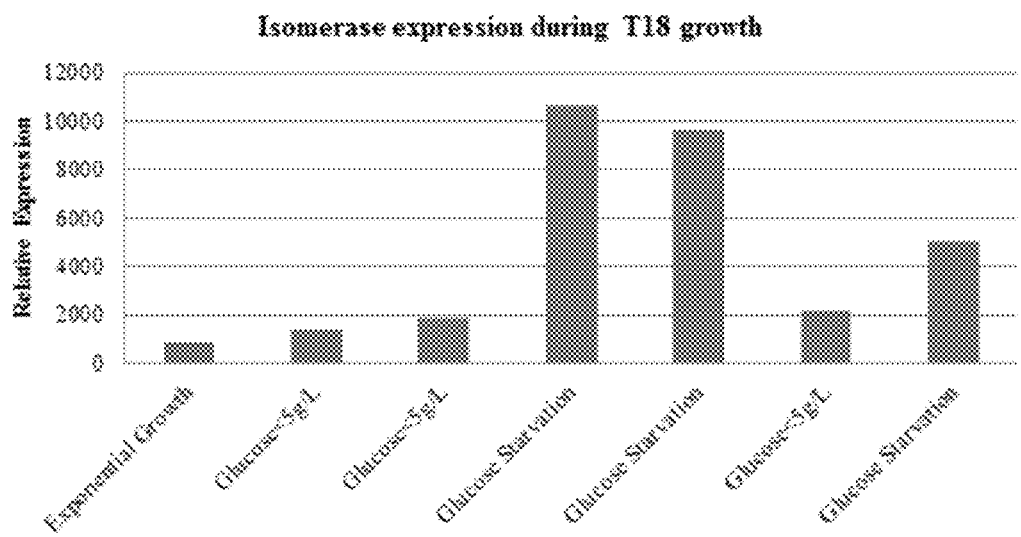
FIG. 2 is a graph showing expression of xylose isomerase in WT ONC-T18 during cycles of glucose starvation.
Figure 3:
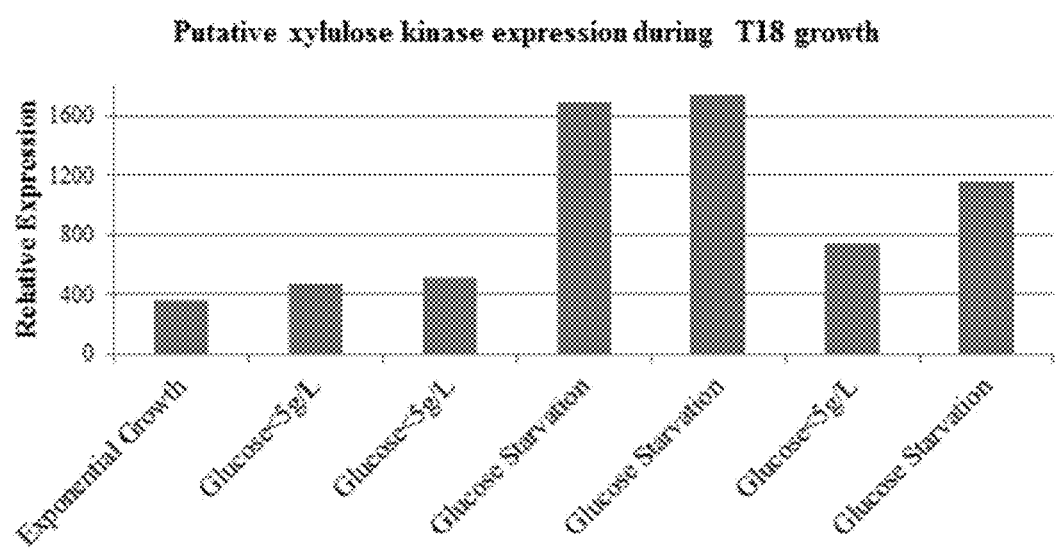
FIG. 3 is a graph showing expression of the putative xylulose kinase in WT ONC-T18 during cycles of glucose starvation.

Microorganisms such as Thraustochytrids encode genes required for the metabolism of xylose. However, the microorganism's innate metabolic pathways produce a large amount of the sugar alcohol, xylitol, which is secreted and potentially hinders growth of the microorganisms (see FIG. 14, WT). Furthermore, carbon atoms sequestered into xylitol are atoms that are diverted away from the target product in this process, namely, lipid production. In nature, two xylose metabolism pathways exist, the xylose reductase/xylitol dehydrogenase pathway and the xylose isomerase/xylulose kinase pathway (FIG. 1). Thraustochytrids have genes that encode proteins active in both pathways; however, the former pathway appears to be dominant as evidenced by a build-up of xylitol when grown in a xylose medium. In other organisms, the build-up of xylitol has been shown to be due to a redox co-factor imbalance required for xylose reductase/ xylitol dehydrogenase pathway. Since the isomerase/kinase pathway does not depend on redox co-factors, over-expression of the isomerase gene removes co-factor dependence in the conversion of xylose to xylulose. As shown herein, transcriptomic studies with ONC-T18 showed that its xylose isomerase and putative xylulose kinase genes are mostly expressed during glucose starvation (FIG. 2 and FIG. 3); whereas, the putatively identified genes encoding for the xylose reductase and xylitol dehydrogenase are constitutively expressed. To increase the expression of the isomerase and kinase throughout all growth stages, microorganisms were engineered to include ONC-T18 isomerase gene and an E. coli xylulose kinase gene (xylB) such that they are under the control of the constitutively expressed promoter and terminator, e.g., an α-tubulin promoter and terminator. Optionally, the genes can be under the control of a inducible promoter and/or terminator.

The provided recombinant microorganisms demonstrate a level of control of the amount of expression of a gene of interest via the number of integrated transgene copies. As shown in the examples below, a recombinant ONC-T18 strain (Iso-His #16) harbouring eight (8) transgene copies demonstrates higher levels of xylose isomerase transcript expression, enzyme activity and xylose metabolism than a strain harbouring a single copy of the transgene (Iso-His #6). When Iso-His #16 was further modified to incorporate the xylB gene, a similar phenomenon is observed. Multiple copies of the xylB gene conferred greater enzyme activity and xylose metabolism productivity compared to single insertions. Thus, unexpectedly, it was not only necessary to recreate a xylose metabolism pathway, but to do so with multiple copies of the necessary transgenes. It was not anticipated that the Thraustrochytrid genome could accommodate multiple transgene copies and remain viable; therefore, it was not expected to observe such variability in expression levels amongst transformant strains. However, as provided herein, recombinant microorganisms can be produced that allow for controlled expression levels of transgenes indirectly by selecting among transformant strains that possess a transgene copy number "tailored" to a particular expression level optimized for the metabolic engineering of a particular pathway, e.g., the xylose pathway.

Provided herein are nucleic acids encoding one or more genes involved in xylose metabolism. The present application provides recombinant microorganisms, methods for making the microorganisms, and methods for producing oil using the microorganisms that are capable of metabolizing xylose. Specifically, provided herein are nucleic acids and polypeptides encoding xylose isomerase, xylulose kinase and xylose transporters for modifying microorganisms to be capable of metabolizing xylose and/or growing on xylose as the sole carbon source. Thus, provided are nucleic acids encoding a xylose isomerase. The nucleic acid sequences can be endogenous or heterologous to the microorganism. Exemplary nucleic acids sequences of xylose isomerases include, but are not limited to, those from *Piromyces* sp., *Streptococcus* sp., and Thraustochytrids. For example, exemplary nucleic acid sequences encoding xylose isomerases include, but are not limited to, SEQ ID NO:2 and SEQ ID NO:15; and exemplary polypeptide sequences of xylose isomerase include, but are not limited to, SEQ ID NO:16. Exemplary nucleic acids sequences of xylulose kinases include, but are not limited to, those from *E. coli, Piromyces* sp., *Saccharomyces* sp., and *Pichia* sp. For example, exemplary nucleic acid sequences encoding xylulose kinases include, but are not limited to, SEQ ID NO:5, SEQ ID NO:17, SEQ ID NO:18, SEQ ID NO:19 and SEQ ID NO:20. Exemplary nucleic acid sequences encoding sugar transporters, e.g., xylose transporters, include, but are not limited to, those from *Aspergillus* sp., Gfx1, Gxs1 and Sut1. For example, exemplary nucleic acid sequences encoding xylose transporters include, but are not limited to, SEQ ID NO:21, SEQ ID NO:22, SEQ ID NO:23, and SEQ ID NO:24.

Nucleic acid, as used herein, refers to deoxyribonucleotides or ribonucleotides and polymers and complements thereof. The term includes deoxyribonucleotides or ribonucleotides in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, conservatively modified variants of nucleic acid sequences (e.g., degenerate codon substitutions) and complementary sequences can be used in place of a particular nucleic acid sequence recited herein. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A nucleic acid is operably linked when it is placed into a functional relationship with another nucleic acid sequence. For example, DNA that encodes a presequence or secretory leader is operably linked to DNA that encodes a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are near each other, and, in the case of a secretory leader, contiguous and in reading phase. However, enhancers do not have to be contiguous. For example, a nucleic acid sequence that is operably linked to a second nucleic acid sequence is covalently linked, either directly or indirectly, to such second sequence, although any effective three-dimensional association is acceptable. A single nucleic acid sequence can be operably linked to multiple other sequences. For example, a single promoter can direct transcription of multiple RNA species. Linking can be accomplished by ligation at convenient restriction sites. If such sites do not exist, the synthetic oligonucleotide adaptors or linkers are used in accordance with conventional practice.

The terms identical or percent identity, in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be substantially identical. This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A comparison window, as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981); by the homology alignment algorithm of Needleman & Wunsch, J. Mol. Biol. 48:443 (1970); by the search for similarity method of Pearson & Lipman, Proc. Nat'l. Acad. Sci. USA 85:2444 (1988); by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection (see, e.g., Current Protocols in Molecular Biology (Ausubel et al., eds. 1995 supplement)).

A preferred example of an algorithm that is suitable for determining percent sequence identity and sequence similarity are the BLAST and BLAST 2.0 algorithms, which are described in Altschul et al., Nuc. Acids Res. 25:3389-3402 (1977), and Altschul et al., J. Mol. Biol. 215:403-410 (1990), respectively. BLAST and BLAST 2.0 are used, with the parameters described herein, to determine percent sequence identity for nucleic acids or proteins. Software for performing BLAST analyses is publicly available through the National Center for Biotechnology Information, as known in the art. This algorithm involves first identifying high scoring sequence pairs (HSPs) by identifying short words of a selected length (W) in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The Expectation value (E) represents the number of different alignments with scores equivalent to or better than what is expected to occur in a database search by chance. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, expectation (E) of 10, and the BLOSUM62 scoring matrix (see Henikoff & Henikoff, Proc. Natl. Acad. Sci. USA 89:10915 (1989)), alignments (B) of 50, expectation (E) of 10, M=5, N=−4, and a comparison of both strands.

The term polypeptide, as used herein, generally has its art-recognized meaning of a polymer of at least three amino acids and is intended to include peptides and proteins. However, the term is also used to refer to specific functional classes of polypeptides, such as, for example, desaturases, elongases, etc. For each such class, the present disclosure provides several examples of known sequences of such polypeptides. Those of ordinary skill in the art will appreciate, however, that the term polypeptide is intended to be sufficiently general as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreover, those in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term polypeptide as used herein. Those in the art can determine other regions of similarity and/or identity by analysis of the sequences of various polypeptides described herein. As is known by those in the art, a variety of strategies are known, and tools are available, for performing comparisons of amino acid or nucleotide sequences in order to assess degrees of identity and/or similarity. These strategies include, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2: 482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTALW, etc. When utilizing BLAST and Gapped BLAST programs, default parameters of the respective programs may be used. Alternatively, the practitioner may use non-default parameters depending on his or her experimental and/or other requirements (see for example, the Web site having URL www.ncbi.nlm.nih.gov).

As discussed above, the nucleic acids encoding the xylose transporter, xylulose kinase and xylose isomerase, can be linked to a promoter and/or terminator. Examples of promoters and terminators include, but are not limited to, tubulin promoters and terminators. By way of example, the promoter is a tubulin promoter, e.g., an alpha-tubulin promoter. Optionally, the promoter is at least 80% identical to SEQ ID NO:25 or SEQ ID NO:26. Optionally, the terminator is a tubulin terminator. Optionally, the terminator is at least 80% identical to SEQ ID NO:27, SEQ ID NO:28, or SEQ ID NO:30.

As used herein, the terms promoter, promoter element, and regulatory sequence refer to a polynucleotide that regulates expression of a selected polynucleotide sequence operably linked to the promoter, and that effects expression of the selected polynucleotide sequence in cells. The term *Thraustochytrium* promoter, as used herein, refers to a promoter that functions in a *Thraustochytrium* cell. In some embodiments, a promoter element is or comprises untranslated regions (UTR) in a position 5' of coding sequences. 5' UTRs form part of the mRNA transcript and so are an integral part of protein expression in eukaryotic organisms. Following transcription 5'UTRs can regulate protein expression at both the transcription and translation levels.

As used herein, the term terminator refers to a polynucleotide that abrogates expression of, targets for maturation (e.g., adding a polyA tail), or imparts mRNA stability to a selected polynucleotide sequence operably linked to the terminator in cells. A terminator sequence may be downstream of a stop codon in a gene. The term *Thraustochytrium* terminator, as used herein, refers to a terminator that functions in a *Thraustochytrium* cell. Provided herein are also nucleic acid constructs that include nucleic acid sequences encoding xylose isomerase, xylulose kinase and xylose transporter as well as promoters, terminators, selectable markers, 2A peptides or any combination thereof. By way of example, provided is a first nucleic acid construct including a promoter, a selectable marker, a nucleic acid sequence encoding a 2A peptide, a nucleic acid sequence encoding a xylose isomerase, and a terminator. Also provided is a second nucleic acid construct including a promoter, selectable marker, a nucleic acid sequence encoding a 2A peptide, a nucleic acid sequence encoding a xylulose kinase, and a terminator. Further provided is a third nucleic acid construct including a promoter, a nucleic acid sequence encoding a xylose transporter, a nucleic acid sequence encoding a 2A peptide, a selectable marker, and a terminator. These constructs are exemplary and the nucleic acid sequences encoding the xylose isomerase, xylulose kinase and xylose transporter can be included on the same construct under control of the same or different promoters. Optionally, each of the nucleic acid sequences encoding the xylose isomerase, xylulose kinase and xylose transporter are on the same construct and are separated by 2A polypeptide sequences, e.g., as shown in SEQ ID NO:6. Thus, by way of example, a nucleic acid construct can include a tubulin promoter, a nucleic acid sequences encoding a xylose isomerase, xylulose kinase, and xylose transporter separated by a nucleic acid sequence encoding SEQ ID NO:6, a tubulin terminator and a selectable marker. Optionally, the selectable marker is the ble gene. Optionally, the selectable marker comprises SEQ ID NO:29.

The phrase selectable marker, as used herein, refers either to a nucleotide sequence, e.g., a gene, that encodes a product (polypeptide) that allows for selection, or to the gene product (e.g., polypeptide) itself. The term selectable marker is used herein as it is generally understood in the art and refers to a marker whose presence within a cell or organism confers a significant growth or survival advantage or disadvantage on the cell or organism under certain defined culture conditions (selective conditions). For example, the conditions may be the presence or absence of a particular compound or a particular environmental condition such as increased temperature, increased radiation, presence of a compound that is toxic in the absence of the marker, etc. The presence or absence of such compound(s) or environmental condition(s) is referred to as a selective condition or selective conditions. By growth advantage is meant either enhanced viability (e.g., cells or organisms with the growth advantage have an increased life span, on average, relative to otherwise identical cells), increased rate of proliferation (also referred to herein as growth rate) relative to otherwise identical cells or organisms, or both. In general, a population of cells having a growth advantage will exhibit fewer dead or nonviable cells and/or a greater rate of cell proliferation than a population of otherwise identical cells lacking the growth advantage. Although typically a selectable marker will confer a growth advantage on a cell, certain selectable markers confer a growth disadvantage on a cell, e.g., they make the cell more susceptible to the deleterious effects of certain compounds or environmental conditions than otherwise identical cells not expressing the marker. Antibiotic resistance markers are a non-limiting example of a class of selectable marker that can be used to select cells that express the marker. In the presence of an appropriate concentration of antibiotic (selective conditions), such a marker confers a growth advantage on a cell that expresses the marker. Thus, cells that express the antibiotic resistance marker are able to survive and/or proliferate in the presence of the antibiotic while cells that do not express the antibiotic resistance marker are not able to survive and/or are unable to proliferate in the presence of the antibiotic.

Examples of selectable markers include common bacterial antibiotics, such as but not limited to ampicillin, kanamycin and chloramphenicol, as well as selective compounds known to function in microalgae; examples include rrnS and AadA (Aminoglycoside 3'-adenylytranferase), which may be isolated from *E. coli* plasmid R538-1, conferring resistance to spectinomycin and streptomycin, respectively in *E. coli* and some microalgae (Hollingshead and Vapnek, Plasmid 13:17-30, 1985; Meslet-Cladière and Vallon, Eukaryot Cell. 10(12):1670-8 2011). Another example is the 23S RNA protein, rrnL, which confers resistance to erythromycin (Newman, Boynton et al., Genetics, 126:875-888 1990; Roffey, Golbeck et al., Proc. Natl Acad. Sci. USA, 88:9122-9126 1991). Another example is Ble, a GC rich gene isolated from *Streptoalloteichus hindustanus* that confers resistance to zeocin (Stevens, Purton et al., Mol. Gen. Genet., 251:23-30 1996). Aph7 is yet another example, which is a *Streptomyces hygroscopicus*-derived aminoglycoside phosphotransferase gene that confers resistance to hygromycin B (Berthold, Schmitt et al., Protist 153(4):401-412 2002). Additional examples include: AphVIII, a *Streptomyces rimosus* derived aminoglycoside 3'-phosphotransferase type VIII that confers resistance to Paromycin in *E. coli* and some microalgae (Sizova, Lapina et al., Gene 181(1-2):13-18 1996; Sizova, Fuhrmann et al., Gene 277(1-2):221-229 2001); Nat & Sat-1, which encode nourseothricin acetyl transferase from *Streptomyces noursei* and streptothricin acetyl transferase from *E. coli*, which confer resistance to nourseothricin (Zaslayskaia, Lippmeier et al., Journal of Phycology 36(2):379-386, 2000); Neo, an aminoglycoside 3'-phosphotransferase, conferring resistance to the aminoglycosides; kanamycin, neomycin, and the analog G418 (Hasnain, Manavathu et al., Molecular and Cellular Biology 5(12):3647-3650, 1985); and Cry1, a ribosomal protein S14 that confers resistance to emetine (Nelson, Savereide et al., Molecular and Cellular Biology 14(6): 4011-4019, 1994).

Other selectable markers include nutritional markers, also referred to as auto- or auxo-trophic markers. These include photoautotrophy markers that impose selection based on the restoration of photosynthetic activity within a photosynthetic organism. Photoautotrophic markers include, but are not limited to, AtpB, TscA, PetB, NifH, psaA and psaB (Boynton, Gillham et al., Science 240(4858):1534-1538 1988; Goldschmidt-Clermont, Nucleic Acids Research 19(15):4083-4089, 1991; Kindle, Richards et al., PNAS, 88(5):1721-1725, 1991; Redding, MacMillan et al., EMBO J 17(1):50-60, 1998; Cheng, Day et al., Biochemical and Biophysical Research Communications 329(3):966-975, 2005). Alternative or additional nutritional markers include ARG7, which encodes argininosuccinate lyase, a critical step in arginine biosynthesis (Debuchy, Purton et al., EMBO J 8(10):2803-2809, 1989); NIT1, which encodes a nitrate reductase essential to nitrogen metabolism (Fernandez, Schnell et al., PNAS, 86(17):6449-6453, 1989); THI10, which is essential to thiamine biosynthesis (Ferris, Genetics 141(2):543-549, 1995); and NIC1, which catalyzes an essential step in nicotinamide biosynthesis (Ferris, Genetics 141(2):543-549, 1995). Such markers are generally enzymes that function in a biosynthetic pathway to produce a compound that is needed for cell growth or survival. In general, under nonselective conditions, the required compound is present in the environment or is produced by an alternative pathway in the cell. Under selective conditions, functioning of the biosynthetic pathway, in which the marker is involved, is needed to produce the compound.

The phrase selection agent, as used herein refers to an agent that introduces a selective pressure on a cell or populations of cells either in favor of or against the cell or population of cells that bear a selectable marker. For example, the selection agent is an antibiotic and the selectable marker is an antibiotic resistance gene. Optionally, zeocin is used as the selection agent.

Suitable microorganisms that can be transformed with the provided nucleic acids encoding the genes involved in xylose metabolism and nucleic acid constructs containing the same include, but are not limited to, algae (e.g., microalgae), fungi (including yeast), bacteria, or protists. Optionally, the microorganism includes Thraustochytrids of the order Thraustochytriales, more specifically Thraustochytriales of the genus *Thraustochytrium*. Optionally, the population of microorganisms includes Thraustochytriales as described in U.S. Pat. Nos. 5,340,594 and 5,340,742, which are incorporated herein by reference in their entireties. The microorganism can be a *Thraustochytrium* species, such as the *Thraustochytrium* species deposited as ATCC Accession No. PTA-6245 (i.e., ONC-T18) as described in U.S. Pat. No. 8,163,515, which is incorporated by reference herein in its entirety. Thus, the microorganism can have an 18s rRNA sequence that is at least 95%, 96%, 97%, 98%, 99%, 99.1%, 99.2%, 99.3%, 99.4%, 99.5%, 99.6%, 99.7%, 99.8%, 99.9% or more (e.g., including 100%) identical to SEQ ID NO:1.

Microalgae are acknowledged in the field to represent a diverse group of organisms. For the purpose of this document, the term microalgae will be used to describe unicellular microorganisms derived from aquatic and/or terrestrial environments (some cyanobacteria are terrestrial/soil dwelling). Aquatic environments extend from oceanic environments to freshwater lakes and rivers, and also include brackish environments such as estuaries and river mouths. Microalgae can be photosynthetic; optionally, microalgae are heterotrophic. Microalgae can be of eukaryotic nature or of prokaryotic nature. Microalgae can be non-motile or motile.

The term thraustochytrid, as used herein, refers to any member of the order Thraustochytriales, which includes the family Thraustochytriaceae. Strains described as thraustochytrids include the following organisms: Order: Thraustochytriales; Family: Thraustochytriaceae; Genera: *Thraustochytrium* (Species: sp., *arudimentale, aureum, benthicola, globosum, kinnei, motivum, multirudimentale, pachydermum, proliferum, roseum, striatum*), *Ulkenia* (Species: sp., *amoeboidea, kerguelensis, minuta, profunda, radiata, sailens, sarkariana, schizochytrops, visurgensis, yorkensis*), *Schizochytrium* (Species: sp., *aggregatum, limnaceum, mangrovei, minutum, octosporuni*), *Japonochytrium* (Species: sp., *marinum*), *Aplanochytrium* (Species: sp., *haliotidis, kerguelensis, profunda, stocchinoi*), *Althornia* (Species: sp., *crouchii*), or *Elina* (Species: sp., *marisalba, sinorifica*). Species described within *Ulkenia* will be considered to be members of the genus *Thraustochytrium*. Strains described as being within the genus *Thrautochytrium* may share traits in common with and also be described as falling within the genus *Schizochytrium*. For example, in some taxonomic classifications ONC-T18 may be considered within the genus *Thrautochytrium*, while in other classifications it may be described as within the genus *Schizochytrium* because it comprises traits indicative of both genera.

The term transformation, as used herein refers to a process by which an exogenous or heterologous nucleic acid molecule (e.g., a vector or recombinant nucleic acid molecule) is introduced into a recipient cell or microorganism. The exogenous or heterologous nucleic acid molecule may or may not be integrated into (i.e., covalently linked to) chromosomal DNA making up the genome of the host cell or microorganism. For example, the exogenous or heterologous polynucleotide may be maintained on an episomal element, such as a plasmid. Alternatively or additionally, the exogenous or heterologous polynucleotide may become integrated into a chromosome so that it is inherited by daughter cells through chromosomal replication. Methods for transformation include, but are not limited to, calcium phosphate precipitation; $Ca^{2+}$ treatment; fusion of recipient cells with bacterial protoplasts containing the recombinant nucleic acid; treatment of the recipient cells with liposomes containing the recombinant nucleic acid; DEAE dextran; fusion using polyethylene glycol (PEG); electroporation; magnetoporation; biolistic delivery; retroviral infection; lipofection; and micro-injection of DNA directly into cells.

The term transformed, as used in reference to cells, refers to cells that have undergone transformation as described herein such that the cells carry exogenous or heterologous genetic material (e.g., a recombinant nucleic acid). The term transformed can also or alternatively be used to refer to microorganisms, strains of microorganisms, tissues, organisms, etc. that contain exogenous or heterologous genetic material.

The term introduce, as used herein with reference to introduction of a nucleic acid into a cell or organism, is intended to have its broadest meaning and to encompass introduction, for example by transformation methods (e.g., calcium-chloride-mediated transformation, electroporation, particle bombardment), and also introduction by other methods including transduction, conjugation, and mating. Optionally, a construct is utilized to introduce a nucleic acid into a cell or organism.

The microorganisms for use in the methods described herein can produce a variety of lipid compounds. As used herein, the term lipid includes phospholipids, free fatty acids, esters of fatty acids, triacylglycerols, sterols and sterol esters, carotenoids, xanthophyls (e.g., oxycarotenoids), hydrocarbons, and other lipids known to one of ordinary skill in the art. Optionally, the lipid compounds include unsaturated lipids. The unsaturated lipids can include polyunsaturated lipids (i.e., lipids containing at least 2 unsaturated carbon-carbon bonds, e.g., double bonds) or highly unsaturated lipids (i.e., lipids containing 4 or more unsaturated carbon-carbon bonds). Examples of unsaturated lipids include omega-3 and/or omega-6 polyunsaturated fatty acids, such as docosahexaenoic acid (i.e., DHA), eicosapentaenoic acid (i.e., EPA), and other naturally occurring unsaturated, polyunsaturated and highly unsaturated compounds.

Provided herein are recombinant microorganisms engineered to express polypeptides for metabolizing C5 carbon sugars such as xylose. Specifically, provided is a recombinant microorganism having one or more copies of a nucleic acid sequence encoding xylose isomerase, wherein the nucleic acid encoding xylose isomerase is a exogenous nucleic acid. Optionally, the recombinant microorganism comprises two or more copies of the nucleic acid sequence encoding xylose isomerase. Optionally, the recombinant microorganisms also contains one or two copies of an endogenous nucleic acid sequence encoding xylose isomerase. By way of example, the recombinant microorganisms can contain one or two copies of an endogenous nucleic acid sequence encoding xylose isomerase and one copy of an exogenous nucleic acid sequence encoding xylose isomerase. Optionally, the recombinant microorganism includes three copies of a nucleic acid sequence encoding xylose isomerase, one being exogenously introduced and the other two being endogenous. The term recombinant when used with reference to a cell, nucleic acid, polypeptide, vector, or the like indicates that the cell, nucleic acid, polypeptide, vector or the like has been modified by or is the result of laboratory methods and is non-naturally occurring. Thus, for example, recombinant microorganisms include microorganisms produced by or modified by laboratory methods, e.g., transformation methods for introducing nucleic acids into the microorganism. Recombinant microorganisms can include nucleic acid sequences not found within the native (non-recombinant) form of the microorganisms or can include nucleic acid sequences that have been modified, e.g., linked to a non-native promoter.

As used herein, the term exogenous refers to a substance, such as a nucleic acid (e.g., nucleic acids including regulatory sequences and/or genes) or polypeptide, that is artificially introduced into a cell or organism and/or does not naturally occur in the cell in which it is present. In other words, the substance, such as nucleic acid or polypeptide, originates from outside a cell or organism into which it is introduced. An exogenous nucleic acid can have a nucleotide sequence that is identical to that of a nucleic acid naturally present in the cell. For example, a Thraustochytrid cell can be engineered to include a nucleic acid having a Thraustochytrid or *Thraustochytrium* regulatory sequence. In a particular example, an endogenous Thraustochytrid or *Thraustochytrium* regulatory sequence is operably linked to a gene with which the regulatory sequence is not involved under natural conditions. Although the Thraustochytrid or *Thraustochytrium* regulatory sequence may naturally occur in the host cell, the introduced nucleic acid is exogenous according to the present disclosure. An exogenous nucleic acid can have a nucleotide sequence that is different from that of any nucleic acid that is naturally present in the cell. For example, the exogenous nucleic acid can be a heterologous nucleic acid, i.e., a nucleic acid from a different species or organism. Thus, an exogenous nucleic acid can have a nucleic acid sequence that is identical to that of a nucleic acid that is naturally found in a source organism but that is different from the cell into which the exogenous nucleic acid is introduced. As used herein, the term endogenous, refers to a nucleic acid sequence that is native to a cell. As used herein, the term heterologous refers to a nucleic acid sequence that is not native to a cell, i.e., is from a different organism than the cell. The terms exogenous and endogenous or heterologous are not mutually exclusive. Thus, a nucleic acid sequence can be exogenous and endogenous, meaning the nucleic acid sequence can be introduced into a cell but have a sequence that is the same as or similar to the sequence of a nucleic acid naturally present in the cell. Similarly, a nucleic acid sequence can be exogenous and heterologous meaning the nucleic acid sequence can be introduced into a cell but have a sequence that is not native to the cell, e.g., a sequence from a different organism.

As discussed above, the provided recombinant microorganisms contain at least two copies of a nucleic acid sequence encoding a xylose isomerase. The provided microorganisms optionally also contain at least one nucleic acid sequence encoding a xylulose kinase. Optionally, the recombinant microorganisms comprise at least one nucleic acid sequence encoding a xylose transporter. The nucleic acid sequences encoding the xylose isomerase, xylulose kinase, and/or xylose transporter are, optionally, exogenous nucleic acid sequences. Optionally, the nucleic acid sequence encoding the xylose isomerase is an endogenous nucleic acid sequence. Optionally, the nucleic acid sequence encoding the xylulose kinase and/or xylose transporter is a heterologous nucleic acid. Optionally, the microorganism contains at least two copies of a nucleic acid sequence encoding a xylose isomerase, at least two copies of a nucleic acid sequence encoding a xylulose kinase, and at least one nucleic acid sequence encoding a xylose transporter. Optionally, the heterologous nucleic acid sequence encoding the xylose isomerase is at least 90% identical to SEQ ID NO:2. Optionally, the heterologous nucleic acid sequence encoding the xylulose kinase is at least 90% identical to SEQ ID NO:5. As noted above, optionally, the nucleic acid encoding the xylose transporter is a heterologous nucleic acid. Optionally, the xylose transporter encoded by the heterologous nucleic acid is GXS1 from *Candida intermedia*. Optionally, the heterologous nucleic acid sequence encoding the xylose transporter is at least 90% identical to SEQ ID NO:23.

The provided recombinant microorganisms not only contain nucleic acid sequences encoding genes involved in xylose metabolism, they can include multiple copies of such sequences. Thus, the microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the nucleic acid sequence encoding xylose isomerase. Optionally, the microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the nucleic acid sequence encoding the xylulose kinase. Optionally, the microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the nucleic acid sequence encoding the xylose transporter.

In the provided microorganisms, the nucleic acids, e.g., xylose isomerase, xylulose kinase or xylose transporter can be operably linked to a promoter and/or terminator. Optionally, the exogenous nucleic acid sequence encoding the xylose isomerase is operably linked to a promoter. Optionally, the nucleic acid sequence encoding the xylulose kinase and/or the nucleic acid sequence encoding the xylose transporter are also operably linked to a promoter. Optionally, the promoter is a tubulin promoter. Optionally, the promoter is at least 80% identical to SEQ ID NO:25 or SEQ ID NO:26. Optionally, the exogenous nucleic acid sequence encoding the xylose isomerase comprises a terminator. Optionally, the nucleic acid sequence encoding the xylulose kinase comprises a terminator. Optionally, the nucleic acid sequence encoding the xylose transporter comprises a terminator. Optionally, the terminator is a tubulin terminator. Optionally, the terminator is at least 80% identical to SEQ ID NO:27, SEQ ID NO:28, or SEQ ID NO:30.

The provided microorganisms can include a selectable marker to confirm transformation of genes of interest. Thus, the microorganism can further include a selectable marker. Optionally, the selectable marker is an antibiotic resistance gene. Optionally, the antibiotic is zeocin, hygromycin B, kanamycin or neomycin. Optionally, the microorganism is either a *Thraustochytrium* or a *Schizochytrium* microorganism. Optionally, the microorganism is ONC-T18.

The provided microorganisms have distinguishing features over wild type microorganisms. For example, the recombinant microorganisms can have increased xylose transport activity as compared to a non-recombinant control (or wild type) microorganism, increased xylose isomerase activity as compared to a non-recombinant control (or wild type) microorganism, increased xylulose kinase activity as compared to a non-recombinant control (or wild type) microorganism, or any combination of these activities. Optionally, the recombinant microorganism grows with xylose as the sole carbon source.

Also provided are methods of making the recombinant microorganisms. Thus, provided is a method of making a recombinant xylose-metabolizing microorganism including providing one or more nucleic acid constructs comprising a nucleic acid sequence encoding a xylose isomerase, a nucleic acid sequence encoding a xylulose kinase and a nucleic acid sequence encoding a xylose transporter; transforming the microorganism with the one or more nucleic acid constructs; and isolating microorganisms comprising at least two copies of the nucleic acid sequences encoding the xylose isomerase. Optionally, the methods further include isolating microorganisms comprising at least two copies of the nucleic acid sequence encoding the xylulose kinase. Optionally, the method includes isolating microorganisms comprising at least one copy of the xylose transporter. Optionally, the one or more nucleic acid constructs further comprise a selectable marker.

In the provided methods, the nucleic acid sequences encoding the xylose isomerase, xylulose kinase and xylose transporter can be located on the same or different constructs. Optionally, the method includes providing a first nucleic acid construct comprising a nucleic acid sequence encoding a xylose isomerase, a second nucleic acid construct comprising a nucleic acid sequence encoding a xylulose kinase and a third nucleic acid construct comprising a nucleic acid sequence encoding a xylose transporter. Optionally, the first, second and third nucleic acid constructs comprise the same selectable marker. Optionally, the first nucleic acid construct comprises a promoter, a selectable marker, a nucleic acid sequence encoding a 2A peptide, the nucleic acid sequence encoding the xylose isomerase, and a terminator. Optionally, the second nucleic acid construct comprises a promoter, selectable marker, a nucleic acid sequence encoding a 2A peptide, the nucleic acid sequence encoding the xylulose kinase, and a terminator. Optionally, the third nucleic acid construct comprises a promoter, the nucleic acid sequence encoding the xylose transporter, a nucleic acid sequence encoding a 2A peptide, a selectable marker, and a terminator. As noted above, selectable markers include, but are not limited to, antibiotic resistance genes. Optionally, the antibiotic is zeocin, hygromycin B, kanamycin or neomycin. Promoters used for the constructs include, but are not limited to, a tubulin promoter. Optionally, the promoter is at least 80% identical to SEQ ID NO:25 or SEQ ID NO:26. Terminators used for the constructs include, but are not limited to, a tubulin terminator. Optionally, the terminator is at least 80% identical to SEQ ID NO:27, SEQ ID NO:28, or SEQ ID NO:30.

In the provided methods, the isolated recombinant microorganisms can include one or more copies of the xylose isomerase, xylulose kinase and xylose transporter. Optionally, the isolated recombinant microorganism comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the nucleic acid sequence encoding xylose isomerase. Optionally, the xylose isomerase is an endogenous xylose isomerase or a heterologous xylose isomerase. Optionally, the nucleic acid sequence encoding the xylose isomerase is at least 90% identical to SEQ ID NO:2. Optionally, the isolated recombinant microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the nucleic acid sequence encoding the xylulose kinase. Optionally, the xylulose kinase is a heterologous xylulose kinase. Optionally, the nucleic acid sequence encoding the xylulose kinase is at least 90% identical to SEQ ID NO:5. Optionally, the isolated recombinant microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the nucleic acid sequence encoding the xylose transporter. Optionally, the xylose transporter is a heterologous xylose transporter. Optionally, the xylose transporter is GXS1 from *Candida intermedia*. Optionally, the nucleic acid sequence encoding the xylose transporter is at least 90% identical to SEQ ID NO:23. Optionally, the microorganism is either a *Thraustochytrium* or a *Schizochytrium* microorganism. Optionally, the microorganism is ONC-T18.

As noted above, the isolated recombinant microorganisms can have increased xylose transport activity as compared to a control non-recombinant microorganism, increased xylose isomerase activity as compared to a control non-recombinant microorganism, increased xylulose kinase activity as compared to a control non-recombinant microorganism, or a combination thereof. Optionally, the isolated recombinant microorganism grows with xylose as the sole carbon source.

As described herein, a control or standard control refers to a sample, measurement, or value that serves as a reference, usually a known reference, for comparison to a test sample, measurement, or value. For example, a test microorganism, e.g., a microorganism transformed with nucleic acid sequences encoding genes for metabolizing xylose can be compared to a known normal (wild-type) microorganism (e.g., a standard control microorganism). A standard control can also represent an average measurement or value gathered from a population of microorganisms (e.g., standard control microorganisms) that do not grow or grow poorly on xylose as the sole carbon source or that do not have or have minimal levels of xylose isomerase activity, xylulose kinase activity and/or xylose transport activity. One of skill will recognize that standard controls can be designed for assessment of any number of parameters (e.g., RNA levels, polypeptide levels, specific cell types, and the like).

Provided herein are also methods of producing oil using the recombinant microorganisms. The method includes providing the recombinant microorganism, wherein the microorganism grows on xylose as the sole carbon source, and culturing the microorganism in a culture medium under suitable conditions to produce the oil. Optionally, the oil comprises triglycerides. Optionally, the oil comprises alpha linolenic acid, arachidonic acid, docosahexanenoic acid, docosapentaenoic acid, eicosapentaenoic acid, gamma-linolenic acid, linoleic acid, linolenic acid, or a combination thereof. Optionally, the method further includes isolating the oil.

The provided methods include or can be used in conjunction with additional steps for culturing microorganisms according to methods known in the art. For example, a Thraustochytrid, e.g., a *Thraustochytrium* sp., can be cultivated according to methods described in U.S. Patent Publications 2009/0117194 or 2012/0244584, which are herein incorporated by reference in their entireties for each step of the methods or composition used therein.

Microorganisms are grown in a growth medium (also known as culture medium). Any of a variety of medium can be suitable for use in culturing the microorganisms described herein. Optionally, the medium supplies various nutritional components, including a carbon source and a nitrogen source, for the microorganism. Medium for Thraustochytrid culture can include any of a variety of carbon sources. Examples of carbon sources include fatty acids, lipids, glycerols, triglycerols, carbohydrates, polyols, amino sugars, and any kind of biomass or waste stream. Fatty acids include, for example, oleic acid. Carbohydrates include, but are not limited to, glucose, cellulose, hemicellulose, fructose, dextrose, xylose, lactulose, galactose, maltotriose, maltose, lactose, glycogen, gelatin, starch (corn or wheat), acetate, m-inositol (e.g., derived from corn steep liquor), galacturonic acid (e.g., derived from pectin), L-fucose (e.g., derived from galactose), gentiobiose, glucosamine, alpha-D-glucose-1-phosphate (e.g., derived from glucose), cellobiose, dextrin, alpha-cyclodextrin (e.g., derived from starch), and sucrose (e.g., from molasses). Polyols include, but are not limited to, maltitol, erythritol, and adonitol. Amino sugars include, but are not limited to, N-acetyl-D-galactosamine, N-acetyl-D-glucosamine, and N-acetyl-beta-D-mannosamine.

Optionally, the microorganisms provided herein are cultivated under conditions that increase biomass and/or production of a compound of interest (e.g., oil or total fatty acid (TFA) content). Thraustochytrids, for example, are typically cultured in saline medium. Optionally, Thraustochytrids can be cultured in medium having a salt concentration from about 0.5 g/L to about 50.0 g/L. Optionally, Thraustochytrids are cultured in medium having a salt concentration from about 0.5 g/L to about 35 g/L (e.g., from about 18 g/L to about 35 g/L). Optionally, the Thraustochytrids described herein can be grown in low salt conditions. For example, the Thraustochytrids can be cultured in a medium having a salt concentration from about 0.5 g/L to about 20 g/L (e.g., from about 0.5 g/L to about 15 g/L). The culture medium optionally includes NaCl. Optionally, the medium includes natural or artificial sea salt and/or artificial seawater.

The culture medium can include non-chloride-containing sodium salts as a source of sodium. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein. A significant portion of the total sodium, for example, can be supplied by non-chloride salts such that less than about 100%, 75%, 50%, or 25% of the total sodium in culture medium is supplied by sodium chloride.

Medium for Thraustochytrids culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$)), peptone, tryptone, yeast extract, malt extract, fish meal, sodium glutamate, soy extract, casamino acids and distiller grains. Concentrations of nitrogen sources in suitable medium typically range between and including about 1 g/L and about 25 g/L.

The medium optionally includes a phosphate, such as potassium phosphate or sodium-phosphate. Inorganic salts and trace nutrients in medium can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium can be sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar or agarose) that provide structural support and/or allow the medium to be in solid form.

Optionally, the resulting biomass is pasteurized to inactivate undesirable substances present in the biomass. For example, the biomass can be pasteurized to inactivate compound degrading substances. The biomass can be present in the fermentation medium or isolated from the fermentation medium for the pasteurization step. The pasteurization step can be performed by heating the biomass and/or fermentation medium to an elevated temperature. For example, the biomass and/or fermentation medium can be heated to a temperature from about 50° C. to about 95° C. (e.g., from about 55° C. to about 90° C. or from about 65° C. to about 80° C.). Optionally, the biomass and/or fermentation medium can be heated from about 30 minutes to about 120 minutes (e.g., from about 45 minutes to about 90 minutes, or from about 55 minutes to about 75 minutes). The pasteurization can be performed using a suitable heating means, such as, for example, by direct steam injection.

Optionally, no pasteurization step is performed. Stated differently, the method taught herein optionally lacks a pasteurization step.

Optionally, the biomass can be harvested according to a variety of methods, including those currently known to one skilled in the art. For example, the biomass can be collected from the fermentation medium using, for example, centrifugation (e.g., with a solid-ejecting centrifuge) or filtration (e.g., cross-flow filtration). Optionally, the harvesting step includes use of a precipitation agent for the accelerated collection of cellular biomass (e.g., sodium phosphate or calcium chloride).

Optionally, the biomass is washed with water. Optionally, the biomass can be concentrated up to about 20% solids. For example, the biomass can be concentrated to about 5% to about 20% solids, from about 7.5% to about 15% solids, or from about solids to about 20% solids, or any percentage within the recited ranges. Optionally, the biomass can be concentrated to about 20% solids or less, about 19% solids or less, about 18% solids or less, about 17% solids or less, about 16% solids or less, about 15% solids or less, about 14% solids or less, about 13% solids or less, about 12% solids or less, about 11% solids or less, about 10% solids or less, about 9% solids or less, about 8% solids or less, about 7% solids or less, about 6% solids or less, about 5% solids or less, about 4% solids or less, about 3% solids or less, about 2% solids or less, or about 1% solids or less.

The provided methods, optionally, include isolating the polyunsaturated fatty acids from the biomass or microorganisms. Isolation of the polyunsaturated fatty acids can be performed using one or more of a variety of methods, including those currently known to one of skill in the art. For example, methods of isolating polyunsaturated fatty acids are described in U.S. Pat. No. 8,163,515, which is incorporated by reference herein in its entirety. Optionally, the medium is not sterilized prior to isolation of the polyunsaturated fatty acids. Optionally, sterilization comprises an increase in temperature. Optionally, the polyunsaturated fatty acids produced by the microorganisms and isolated from the provided methods are medium chain fatty acids. Optionally, the one or more polyunsaturated fatty acids are selected from the group consisting of alpha linolenic acid, arachidonic acid, docosahexanenoic acid, docosapentaenoic acid, eicosapentaenoic acid, gamma-linolenic acid, linoleic acid, linolenic acid, and combinations thereof.

Oil including polyunsaturated fatty acids (PUFAs) and other lipids produced according to the method described herein can be utilized in any of a variety of applications exploiting their biological, nutritional, or chemical properties. Thus, the provided methods optionally include isolating oil from the harvested portion of the threshold volume. Optionally, the oil is used to produce fuel, e.g., biofuel. Optionally, the oil can be used in pharmaceuticals, food supplements, animal feed additives, cosmetics, and the like. Lipids produced according to the methods described herein can also be used as intermediates in the production of other compounds.

By way of example, the oil produced by the microorganisms cultured using the provided methods can comprise fatty acids. Optionally, the fatty acids are selected from the group consisting of alpha linolenic acid, arachidonic acid, docosahexaenoic acid, docosapentaenoic acid, eicosapentaenoic acid, gamma-linolenic acid, linoleic acid, linolenic acid, and combinations thereof. Optionally, the oil comprises triglycerides. Optionally, the oil comprises fatty acids selected from the group consisting of palmitic acid (C16:0), myristic acid (C14:0), palmitoleic acid (C16:1(n-7)), cis-vaccenic acid (C18:1(n-7)), docosapentaenoic acid (C22:5(n-6)), docosahexaenoic acid (C22:6(n-3)), and combinations thereof.

Optionally, the lipids produced according to the methods described herein can be incorporated into a final product (e.g., a food or feed supplement, an infant formula, a pharmaceutical, a fuel, etc.). Suitable food or feed supplements into which the lipids can be incorporated include beverages such as milk, water, sports drinks, energy drinks, teas, and juices; confections such as candies, jellies, and biscuits; fat-containing foods and beverages such as dairy products; processed food products such as soft rice (or porridge); infant formulae; breakfast cereals; or the like. Optionally, one or more produced lipids can be incorporated into a dietary supplement, such as, for example, a vitamin or multivitamin. Optionally, a lipid produced according to the method described herein can be included in a dietary supplement and optionally can be directly incorporated into a component of food or feed (e.g., a food supplement).

Examples of feedstuffs into which lipids produced by the methods described herein can be incorporated include pet foods such as cat foods; dog foods; feeds for aquarium fish, cultured fish or crustaceans, etc.; feed for farm-raised animals (including livestock and fish or crustaceans raised in aquaculture). Food or feed material into which the lipids produced according to the methods described herein can be incorporated is preferably palatable to the organism which is the intended recipient. This food or feed material can have any physical properties currently known for a food material (e.g., solid, liquid, soft).

Optionally, one or more of the produced compounds (e.g., PUFAs) can be incorporated into a nutraceutical or pharmaceutical product. Examples of such a nutraceuticals or pharmaceuticals include various types of tablets, capsules, drinkable agents, etc. Optionally, the nutraceutical or pharmaceutical is suitable for topical application. Dosage forms can include, for example, capsules, oils, granula, granula subtilae, pulveres, tabellae, pilulae, trochisci, or the like.

The oil or lipids produced according to the methods described herein can be incorporated into products as described herein in combination with any of a variety of other agents. For instance, such compounds can be combined with one or more binders or fillers, chelating agents, pigments, salts, surfactants, moisturizers, viscosity modifiers, thickeners, emollients, fragrances, preservatives, etc., or any combination thereof.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

Example 1. C5 Carbon Metabolism by Recombinant Thraustochytrids

In nature, two xylose metabolism pathways exist, the xylose reductase/xylitol dehydrogenase pathway and the xylose isomerase/xylulose kinase pathway (FIG. 1). ONC-T18 encodes genes from both pathways, and, as described above, the xylose reductase/xylitol dehydrogenase pathway is dominant, as evidenced by a build-up of xylitol when grown in a xylose medium. Since the isomerase/kinase pathway does not depend on redox co-factors, over-expression of ONC-T18's isomerase gene removes co-factor dependence in the conversion of xylose to xylulose. As shown herein in FIGS. 2 and 3, transcriptomic studies with ONC-T18 showed that its xylose isomerase and putative xylulose kinase genes were mostly expressed during glucose starvation; whereas, the putatively identified genes encoding for the xylose reductase and xylitol dehydrogenase were constitutively expressed.

Figure 20A:
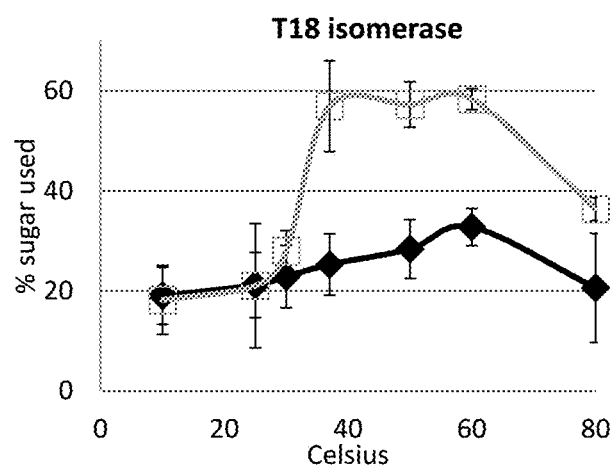
FIGS. 20A and 20B are graphs showing the impact of temperature incubation on the activity of isomerase from T18 (FIG. 20A) and E. coli (FIG. 20B) with xylose (diamond) and xylulose (square).
Figure 20B:
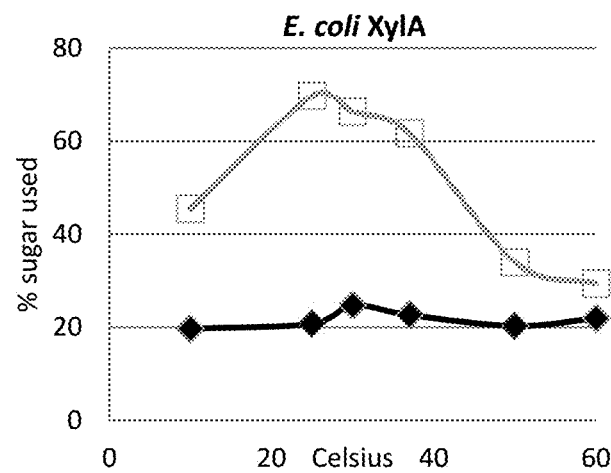

T18 isomerase was purified by metal-affinity chromatography following his-tagging and over-expression in yeast INVSc1. As a positive control, his-tagged XylA from $E.\ coli$ strain W3110 was over-expressed and purified from $E.\ coli$ strain BL21(DE3)plysS. The protein concentration of purified proteins was determined by a standard Bradford assay. The impact of temperature on the activity of T18 isomerase and $E.\ coli$ isomerase was determined using 5 μg of protein and 0.75 g/L of either xylose or xylulose in 5 mM MgATP, 50 mM Hepes (pH 7.4), 10 mM MgCl2. Reactions were incubated overnight at 10° C., 25° C., 30° C., 37° C., 50° C., 60° C., and 80° C. Reactions were stopped by heat inactivation at 95° C. for 5 mins. Reactions were analyzed by HPLC and the concentration of the sugars present was determined from the area under the peak relative to a standard curve. T18 isomerase had higher activity on both xylose and xylulose at temperatures at and above 37° C. (FIG. 20A). This is in contrast to $E.\ coli$ isomerase, which had higher activity at temperatures between 25° C. and 30° C. (FIG. 20B).

Figure 21A:
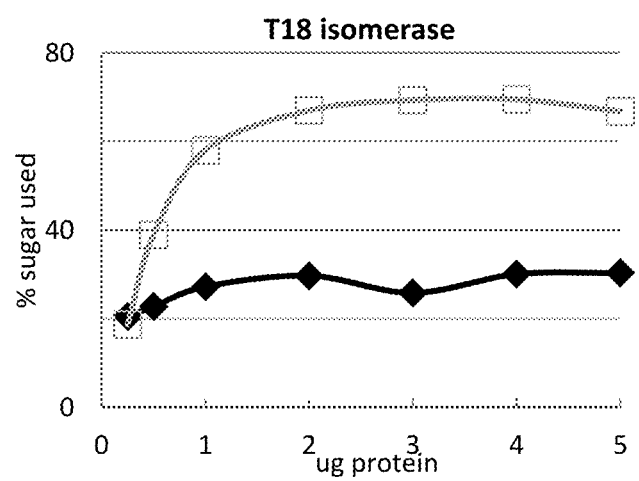
FIGS. 21A and 21B are graphs showing dose dependency of isomerase from T18 (FIG. 21A) and E. coli (FIG. 21B) with xylose (diamond) and xylulose (square).
Figure 21B:
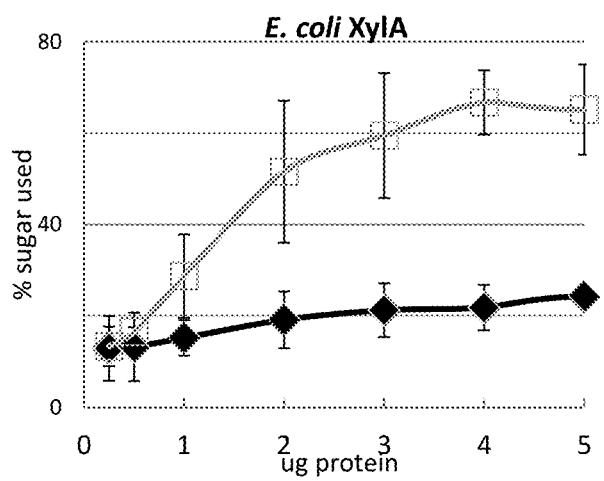
Figures 22A, 22B:
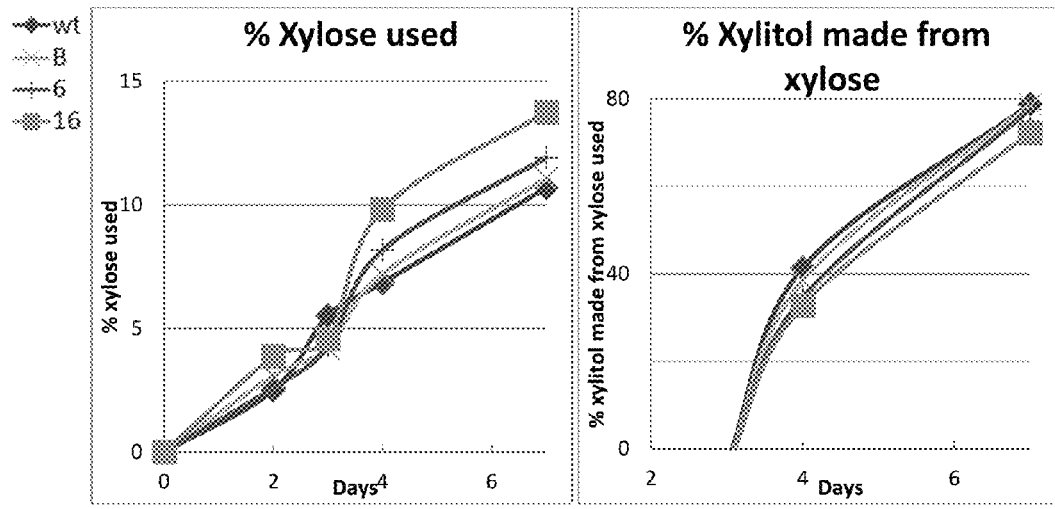
FIGS. 22A and 22B are graphs showing xylose use (FIG. 22A) and decreased xylitol production (FIG. 22B) in a T18B strain engineered with xylose isomerases ("16" (squares), "B" (x), and "6" (crosses)).
Figures 22C, 22D:
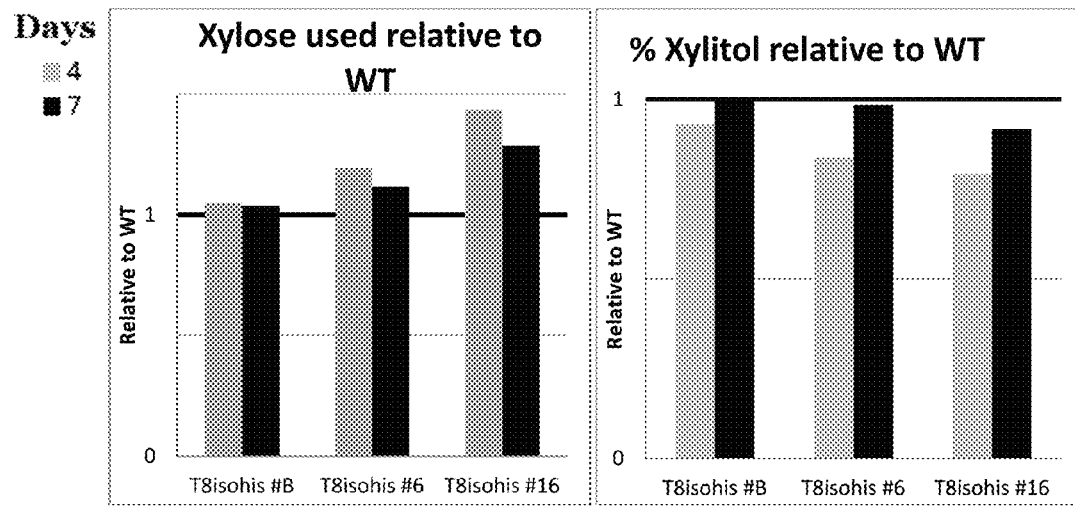
FIGS. 22C (xylose) and 22D (xylitol production) show the same data expressed relative to wild type (diamonds) at 4 (gray) and 7 (black) days.

Dose-dependency was determined by incubating increasing protein concentrations of the isomerase with 0.75 g/L xylose or xylulose in 5 mM MgATP, 50 mM Hepes (pH 7.4), 10 mM MgCl$_2$. Reactions were incubated overnight at 30° C. ($E.\ coli$) or 50° C. (T18) then stopped by heat inactivation at 95° C. for 5 mins. Reactions were analyzed by HPLC and the concentration of the sugars present was determined from the area under the peak relative to a standard curve. Observed was a dose dependency of T18 isomerase on both xylose and xylulose (FIGS. 21A and 21B).

Figure 4:
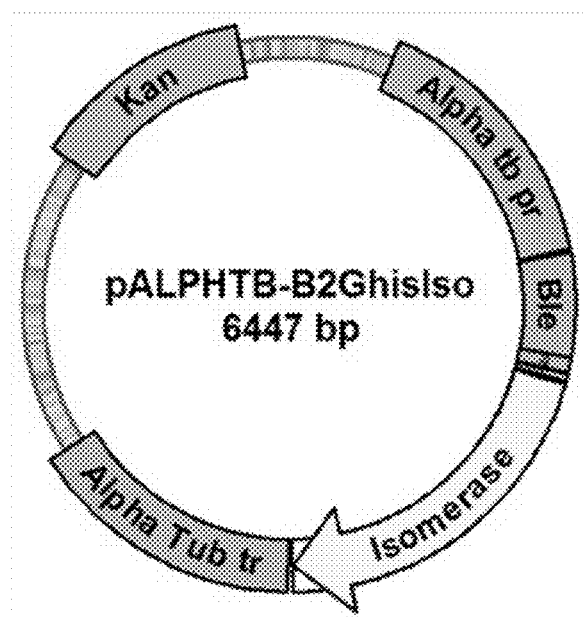
FIG. 4 is a schematic showing an alpha-tubulin ble-isomerase plasmid construct.
Figure 5:
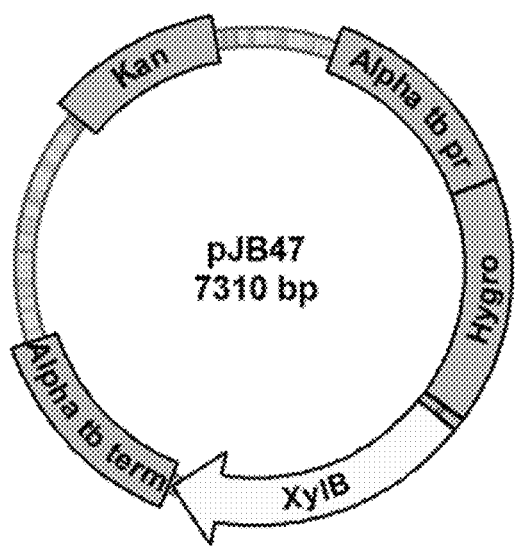
FIG. 5 is a schematic showing an alpha-tubulin hygro-xylB plasmid construct.

This example describes the use of a *Thraustochytrium* ONC-T18-derived (ONC-T18) alpha-tubulin promoter to express endogenous and/or heterologous xylose metabolism transgenes in Thraustochytrid species, including ONC-T18. However, as discussed throughout, other regulatory elements can be used. FIGS. 4 and 5 show constructs of the plasmids containing the xylose isomerase and xylulose kinase genes, respectively. As described herein, the xylose metabolism transgenes were present in multiple (≥8) copies within the genome of the host. In the case of ONC-T18, the modified organisms demonstrated an increased metabolism of xylose compared to wild-type (WT) cells. For example, a strain modified to express an endogenous xylose isomerase gene (SEQ ID NO:2) (strain Iso-His #16) and a strain modified to express an endogenous xylose isomerase gene (SEQ ID NO:2) and a xylulose kinase gene (SEQ ID NO:5) (Iso-His+xylB, strain 7-7) both used 40% more xylose than the WT strain. Both Iso-His #16 and 7-7 converted less xylose to xylitol than the WT strain, 40% less and 420% less, respectively. The constructs used for transformation of ONC-T18 are shown in FIGS. 4 and 5. ONC-T18 tranformants were created using standard biolistics protocols as described by BioRad's Biolistic PDS-1000/He Particle Delivery System (Hercules, Calif.). Briefly, 0.6 μm gold particles were coated with 2.5 μg of linearized plasmid DNA (EcoRI, 37° C., overnight). The coated gold particles were used to bombard plates previously spread with 1 ml of ONC-T18 cells at an OD600 of 1.0. The bombardment parameters included using a helium pressure of 1350 or 1100 psi with a target distance of 3 or 6 cm. After an overnight recovery, the cells were washed off the plate and plated on media containing selection antibiotics (Zeo 250 μg/mL and hygro 400 μg/mL). Plates were incubated for 1 week at 25° C. to identify resistant colonies. The resulting transformants were screened by PCR and Southern blot.

Southern blots were performed using standard protocols. Briefly, approximately 20 μg of genomic DNA were digested with 40 units of BamHI restriction enzyme in a total volume of 50 μL overnight at 37° C. 7.2 μg of each digested sample was run on a 1.0% agarose gel at 50V for approximately 1.5. hours, with a digoxigenin (DIG) DNA molecular-weight marker II (Roche, Basel, Switzerland). DNA was depurinated in the gel by submerging the gel in 250 mM HCl for 15 minutes. The gel was further denatured by incubation in a solution containing 0.5 M NaOH and 1.5 M NaCL (pH 7.5) for two 15 minute washes. The reaction was then neutralized by incubation in 0.5 M Tris-HCl (pH 7.5) for two 15 minute washes. Finally, the gel was equilibrated in 20× saline-sodium citrate (SSC) buffer for 15 minutes. DNA was transferred to a positively charged nylon membrane using a standard transfer apparatus. DNA was fixed to the membrane using a UV Stratalinker at an exposure of 120,000 μJ. Southern blot probe was generated using a PCR DIG Probe Synthesis Kit (Roche, Basel, Switzerland) to generate a DIG-labelled probe according to the manufacturer's instructions. The DNA affixed to the nylon membrane was prehybridized with 20 mL of DIG EasyHyb solution (DIG Easy-Hyb Granules, Roche, Basel, Switzerland). The DIG-labelled probe was denatured by adding 40 μL of the ble-probe reaction mixture to 300 μL of ddH$_2$O and incubated at 99° C. for 5 minutes. This solution was then added to 20 mL of DIG hybridization solution to create the probe solution. The probe solution was then added to the DNA-affixed nylon membrane and incubated at 53° C. overnight. The following day, the membrane was washed twice in 2×SSC, 0.1% SDS at room temperature. The membrane was further washed twice in 0.1×SSC, 0.1% SDS at 68° C. for 15 minutes. For detection, the membrane was washed and blocked using DIG Wash and Block Buffer set (Roche, Basel, Switzerland) according to the manufacturer's instructions. An anti-DIG-AP conjugated antibody from a DIG Nucleic Acid Detection Kit (Roche, Basel, Switzerland) was used for detection. 2 μL of the antibody solution was added to 20 mL detection solution and incubated with the membrane at room temperature for 30 minutes. The blot was then immersed in a washing buffer provided with the kit. CDP-Star (Roche, Basel, Switzerland) was used for visualization. 10 μL of the CDP-star solution was incubated on the membrane in 1 mL of detection solution, which was covered in a layer of 'sheet-protector' plastic to hold the solution to the membrane. Signal was immediately detected using a ChemiDoc imaging system (BioRad Laboratories, Hercules, Calif.).

Figure 6:
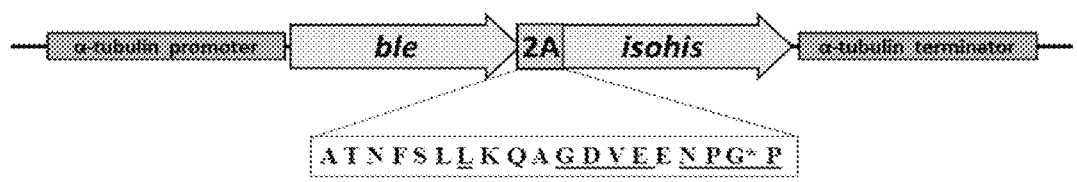
FIG. 6 is a schematic showing a nucleic acid construct having an alpha-tubulin promoter a ble sequence a 2A sequence an xylose isomerase sequence and an alpha-tubulin terminator.

The codon optimized ble gene was cloned under the control of T18B α-tubulin promoter and terminator elements (FIG. 6). The isomerase gene was cloned from T18B in such a way as to add a six-histidine tag on the N-terminus of the expressed protein (Iso-His). Xylose isomerase enzymatic activity was confirmed by over-expression and purification of the histidine-tagged protein in yeast. The isomerase gene (along with the introduced six-histidine tag) was cloned under the control of the α-tubulin promoter and terminators by cloning the gene downstream of the ble gene and a 2A sequence (FIG. 4 and FIG. 6). Biolistic transformation of T18B with this plasmid (pALPHTB-B2G-hisIso) resulted in Zeocin (zeo) resistant transformants. Many transformant strains were obtained from this procedure. Two of these strains are shown as example #6 containing one copy of the transgene and example #16 containing eight copies of the transgene (FIG. 7).

Figure 7:
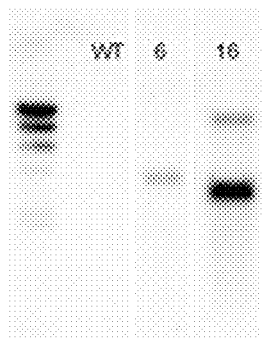
FIG. 7 is an image of a Southern blot to probe the xylose isomerase His-tagged gene within recombinant ONC-T18 strains "6" and "16".
Figure 8:
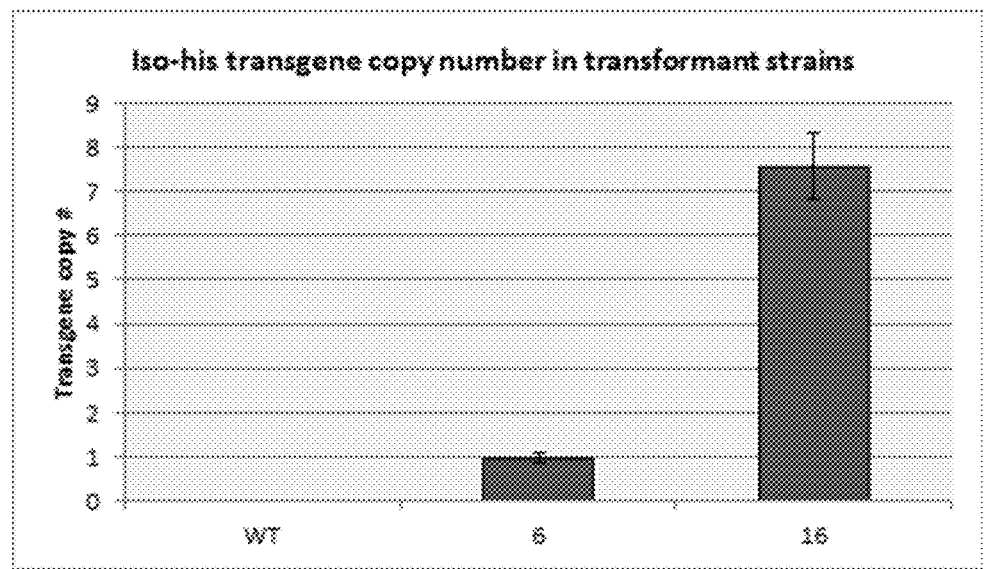
FIG. 8 is a graph showing the qPCR determination of the number of xylose isomerase His-tagged gene insertions in recombinant ONC-T18 strains.
Figure 11:
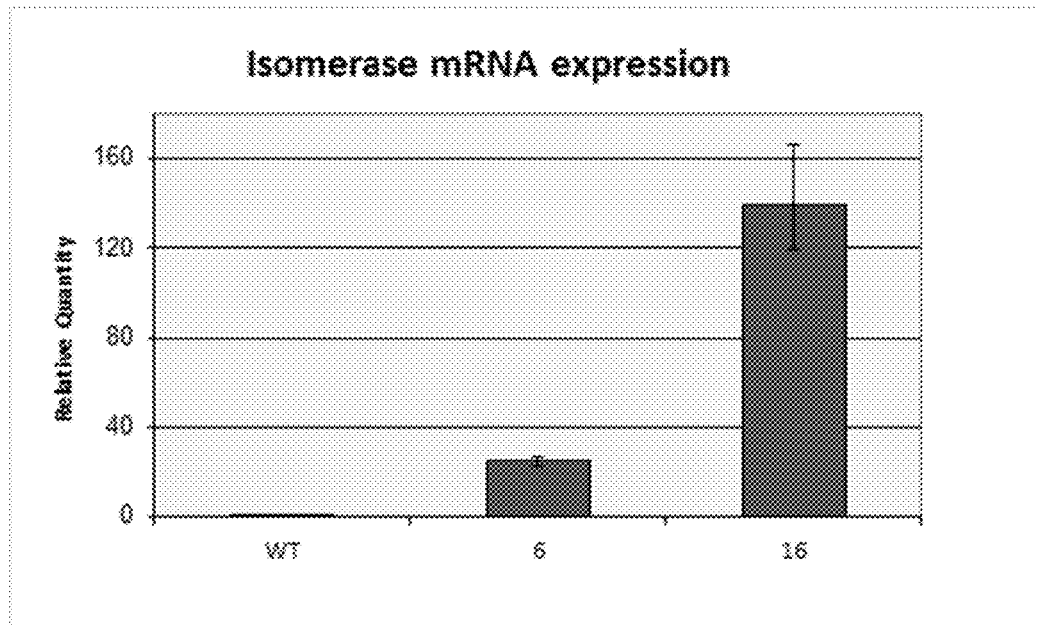
FIG. 11 is a graph showing the expression of the xylose isomerase gene transcript in recombinant ONC-T18 strains "6" and "16.
Figure 12:
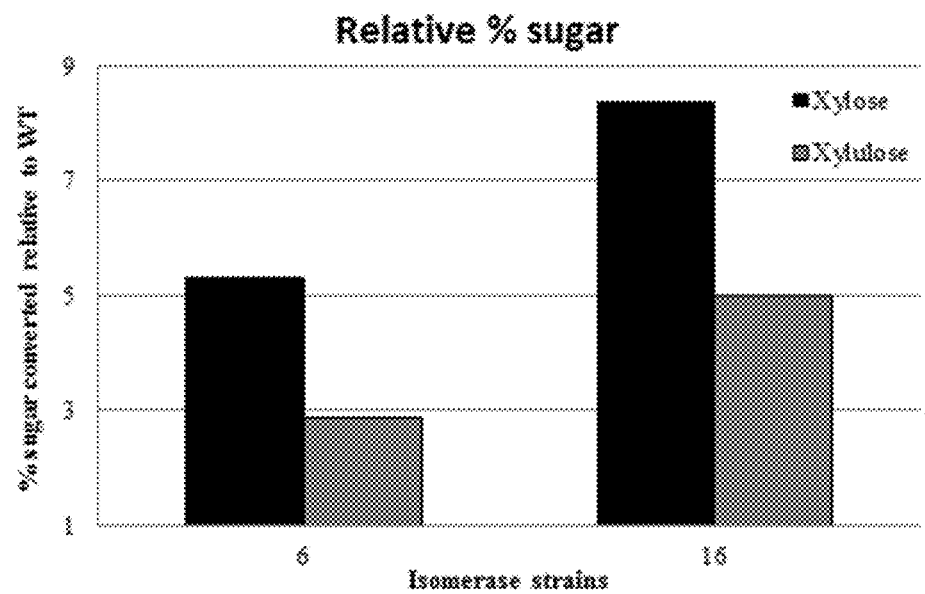
"
FIG. 12 is a graph showing the in vitro xylose isomerase activity in Wt ONC-T18 and recombinant ONC-T18 strains "6" and "16.
Figure 14A:
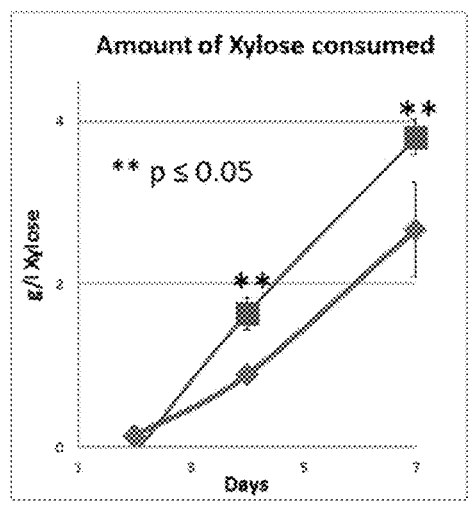
FIGS. 14A and 14B are graphs showing xylose uptake improvement and decreased xylitol production in recombinant ONC-T18 strain "16" (squares). The Wild Type (WT) strain is represented by diamonds.
Figure 14B:
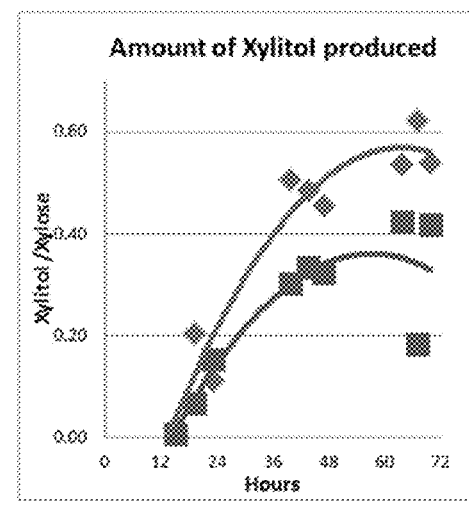

The insertion of the Iso-His transgene within the T18B genome was confirmed by PCR and Southern blot analysis (FIG. 7). Qualitatively, these data showed the presence of a single copy of the transgene in strain #6 and multiple, concatameric, transgene copies, at a single site, in strain #16. The precise number of Iso-His transgene insertions was determined by qPCR on genomic DNA (FIG. 8). These data showed the presence of one copy of the transgene in strain #6 and eight copies of the transgene in strain #16 (FIG. 8). To test whether an increase in copy number correlated with an increase in expression level, mRNA was isolated from WT, Iso-His #6 and Iso-His #16 T18B cells and qRT-PCR was performed. FIG. 11 shows significantly increased expression of the Iso-His transcript in strain #16 cells, containing eight copies of the transgene, compared to strain #6, containing a single copy of the transgene. No Iso-His transcript is detectable in WT cells (FIG. 11). To assess whether increased mRNA expression correlated with increased isomerase enzymatic activity, cell extracts were harvested from WT, Iso-His #6 and Iso-His #16 cells. Enhanced isomerase enzyme activity is observed in strain #16 cells compared with strain #6 and WT cells (FIG. 12). Finally, the ability of strain #16 to metabolize xylose was examined in xylose depletion assays (FIG. 14) and compared with WT cells. These flask fermentations demonstrated the ability to metabolise xylose and quantify the amount of xylose converted to xylitol. Thus, FIG. 14 shows an increase in xylose metabolism in Iso-His strain #16 compared with WT cells and significantly less production of xylitol.

For flasks assays, cells were grown in media for 2 to 3 days. Pellets were washed twice in Media 2 (9 g/L NaCl, 4 g/L MgSO$_4$, 100 mg/L CaCl$_2$, 5 mg/L FeCl$_3$, 20 g/L (NH$_4$)$_2$SO$_4$, 0.86 g/L KH$_2$PO$_4$, 150 μg/L vitamin B12, 30 μg/L biotin, 6 mg/L thiamine hydrochloride, 1.5 mg/L cobalt (II) chloride, 3 mg/L manganese chloride) containing no sugar. Then, minimal media containing 20 g/L glucose & 50 g/L xylose was inoculated to an OD600 of 0.05 with the washed cells. Samples were taken at various time points and the amount of sugar remaining in the supernatant was analyzed by HPLC. As shown in FIGS. 22A, 22B, 22C and 22D, with increased xylose isomerase gene copy number, up to 40% more xylose usage and 20% decrease in xylitol production when compared to WT.

Figure 9:
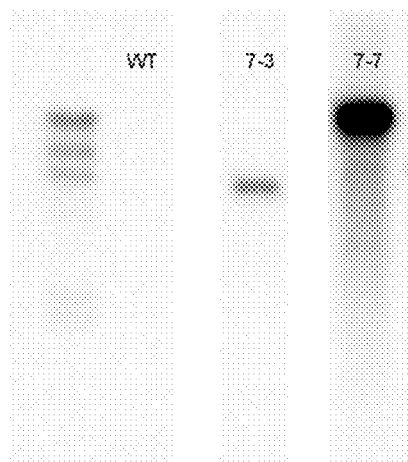
FIG. 9 is an image of a Southern blot to probe the xylB gene within recombinant ONC-T18 strains containing both xylose isomerase and xylulose kinase referred to in the graph as "7-3" and "7-7".
Figure 10:
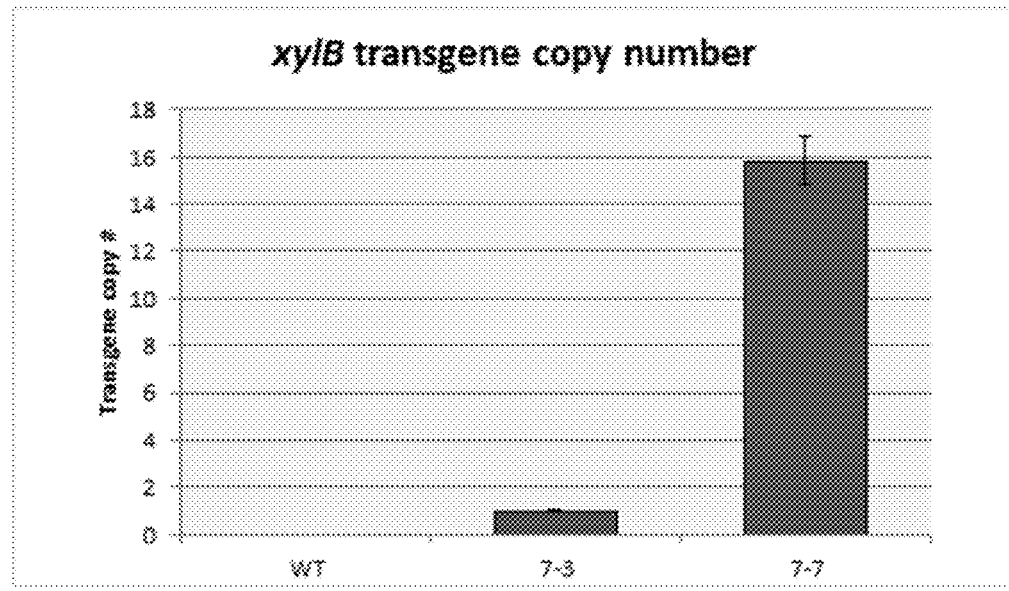
FIG. 10 is a graph of qPCR determination of the number of xylB gene insertions in recombinant 7-3 and 7-7 ONC-T18 strains.
Figure 13:
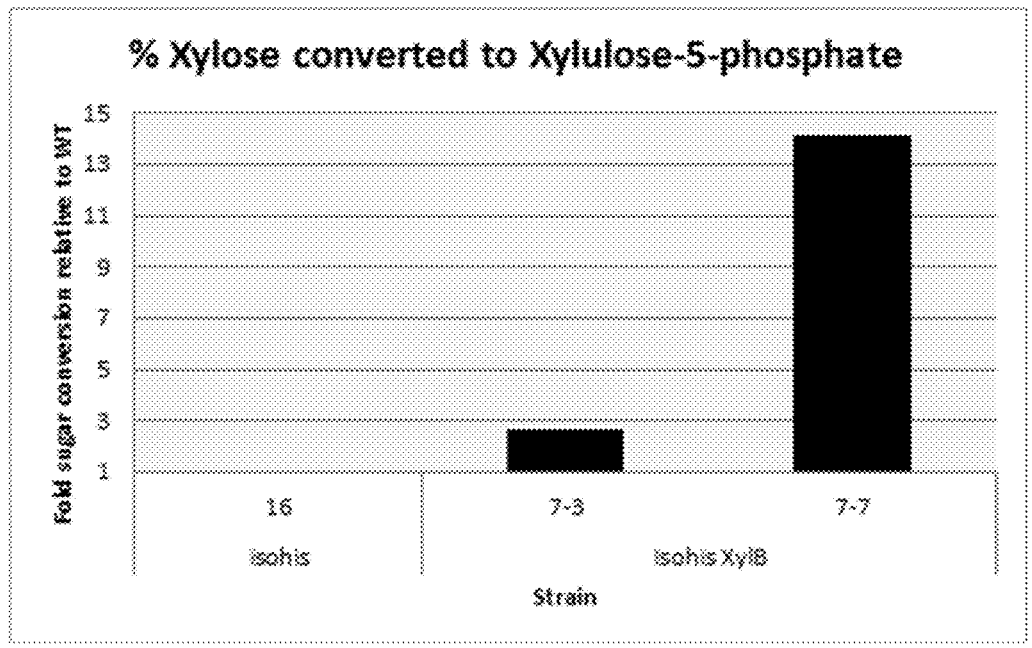
"
FIG. 13 is a graph showing the combined xylose isomerase and xylulose kinase activity in vitro of recombinant ONC-T18 strain "16" encoding only xylose isomerase and recombinant ONC-T18 strains "7-3" and "7-7" encoding xylose isomerase and xylulose kinase.
Figure 15A:
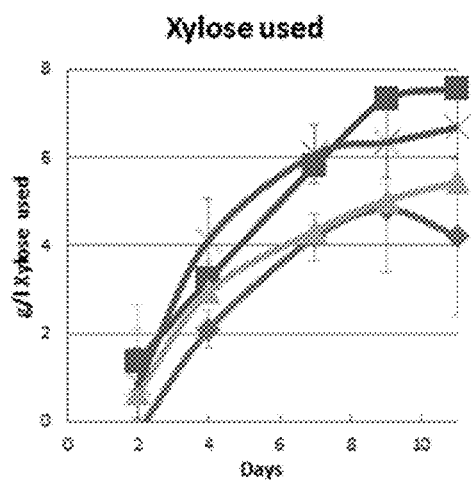
FIGS. 15A and 15B are graphs showing xylose usage improvement and decreased xylitol production in recombinant ONC-T18 strain "16" (squares) and recombinant ONC-T18 strains "7-3" (triangles) and "7-7" (asterisks). The Wild Type (WT) strain is represented by diamonds.
Figure 15B:
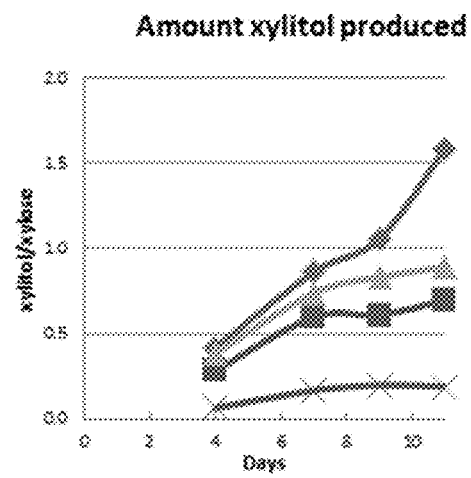
Figure 16:
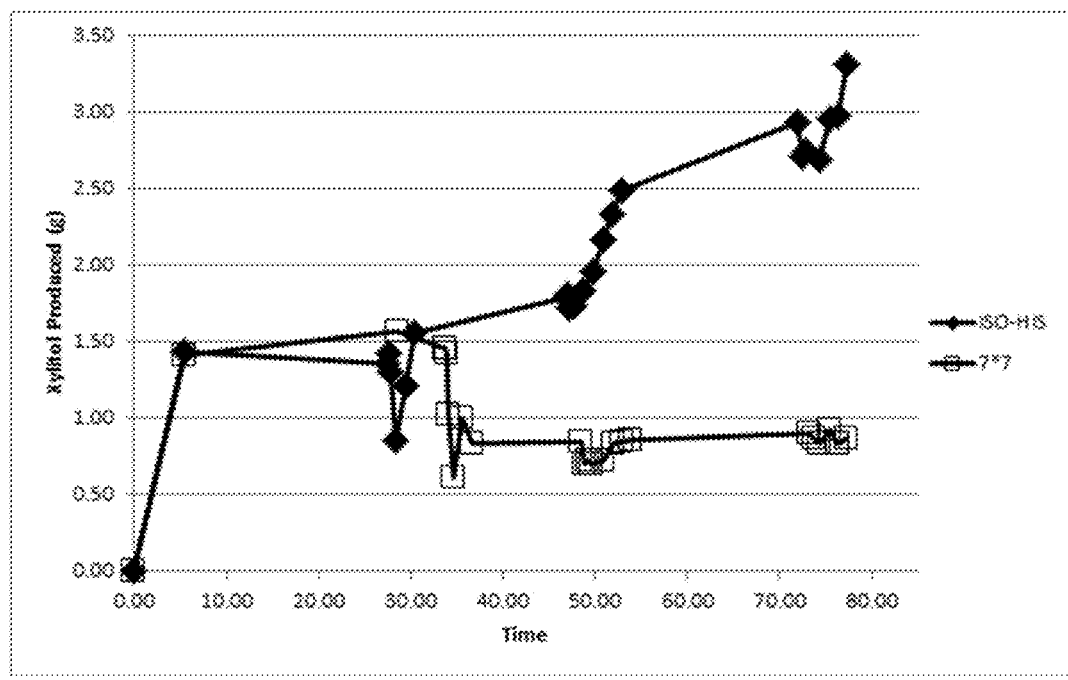
FIG. 16 is a graph showing accumulation of xylitol during a glucose:xylose fermentation with recombinant ONC-T18 strain "16" and recombinant ONC-T18 strain "7-7.

Iso-His strain #16 was then used as the parent strain for a second round of transformation to introduce the E. coli xylB gene. This gene was introduced under hygromycin (hygro) selection. The hygro gene from pChlamy_3, the 2A sequence, and the T18B codon optimized W3110 E. coli xylB gene were cloned under the control of the T18B α-tubulin promoter and terminator elements for expression in T18B iso-his #16 (FIG. 5). The in vitro ability of the E. coli xylulose kinase to work in concert with the T18B isomerase was confirmed by over-expression and purification of the histidine-tagged proteins in yeast followed by enzymatic reactions with xylose and xylulose. Biolistic transformation of T18B iso-his strain #16 with the xylB plasmid (pJB47) resulted in hygro and zeo resistant transformants. The insertion of the hygro-2A-xylB genes within the T18B genome was confirmed by PCR and Southern blot analysis (FIG. 9). Qualitatively, these data show the presence of a single copy of the transgene in strain #7-3 and multiple, concatameric, transgene copies, at a single site, in strain #7-7. The number of xylB gene insertions was determined by qPCR on genomic DNA isolations (FIG. 10). FIG. 10 shows sixteen insertions of the transgene in strain 7-7 and one copy in strain 7-3. To determine whether multiple copies of the transgene confer enhanced xylose metabolism in vitro, cell extract assays were performed and the ability of the cells extracts to metabolize xylose was analysed (FIG. 13). The ability of the transformant cells to metabolize xylose was examined through flask-based xylose depletion assays (FIG. 15). In this experiment, WT cells consumed the least amount of xylose and made the most xylitol. Strain Iso-His #16, 7-3 and 7-7 all consumed similar amounts of xylose; however, only 7-7, containing multiple copies of the xylB transgene, did not make significant amounts of xylitol. Finally, strains Iso-His #16 and 7-7 were tested at in 5 L fermentation vessels in media containing glucose and xylose. During a seventy-seven (77) hour fermentation, strain Iso-His #16 converted approximately 8% of xylose to xylitol, whereas strain 7-7 converted approximately 2% of xylose to xylitol. Xylitol accumulation in this fermentation is shown in FIG. 16.

For flasks assays, cells were grown in media for 2 to 3 days. Pellets were washed twice in media containing no sugar. Media containing 20 g/L:50 g/L glucose:xylose was inoculated to an OD600 of 0.05 with the washed cells. Samples were taken at various time points and the amount of sugar remaining in the supernatant was analyzed by HPLC. As shown in FIGS. 23A, 23B, 23C and 23D, up to 50% more xylose was used and an 80% reduction in xylitol was observed in strains over-expressing both a xylose isomerase and a xylulose kinase when compared to WT.

Figure 24:
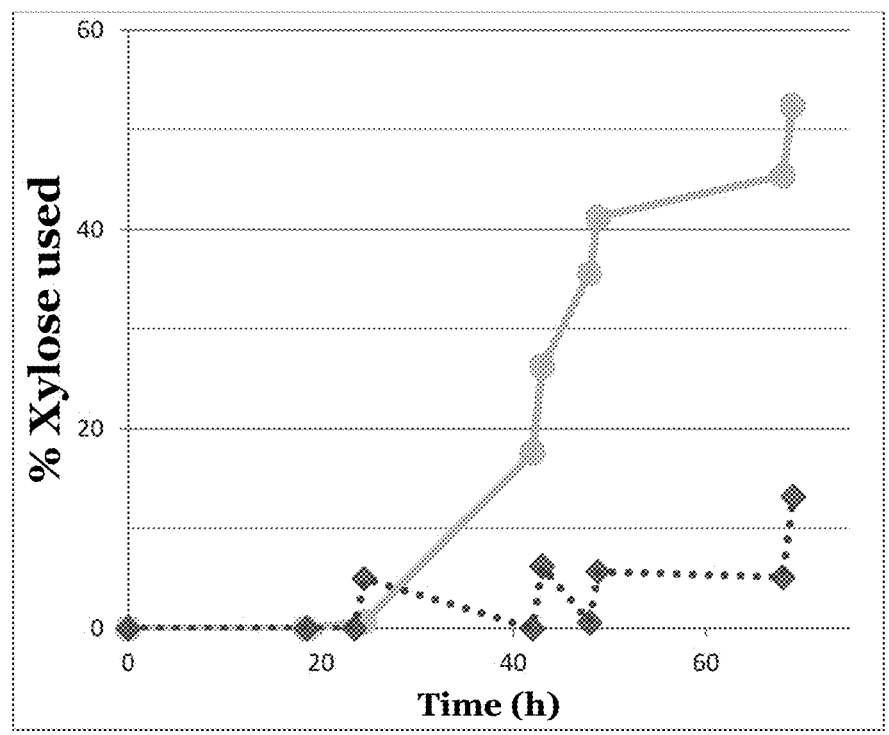
FIG. 24 is a graph showing improved xylose usage and decreased xylitol production in a T18B strain engineered to express a xylose isomerase and xylulose kinase "7-7" in fermentation. The wild type strain is represented by diamonds and the dotted line and the strain "7-7" is represented by circles.

To further analyze these strains, the strains were grown in parallel 5 L Sartorius fermenters. Initial media contained 20 g/L Glucose and 50 g/L xylose along with other basal media components. Both cultures were maintained at 28° C. and 5.5 pH, with constant mixing at 720 RPM and constant aeration at 1 Lpm of environmental air. The cultures were fed glucose for 16 hrs followed by 8 hr starvation period. This cycle was completed 3 times. During starvation periods, 10 mL samples were taken every 0.5 hr. Glucose, xylose and xylitol concentrations were quantified in these samples by HPLC. Larger 50 mL samples were taken periodically for further biomass and oil content quantification. Glucose feed rates matched glucose consumption rates, which was quantified by $CO_2$ detected in the culture exhaust gas. As shown in FIG. 24, the 7-7 strain used up to 52% more xylose than WT under these conditions.

By Southern blot analysis, it was observed that strain Iso-His #16 contains eight (8) insertions of the isomerase transgene (FIG. 8). This unexpected multiple insertion resulted in an increase in isomerase gene expression relative to strains harbouring a single copy (FIG. 11) as well as increased isomerase in vitro activity (FIG. 12). Strain Iso-His #16 demonstrated increased xylose productivity than strains harbouring a single copy of the isomerase transgene (FIG. 14).

Similarly, within the Iso-His+xylB transformants, one of the clones (Iso-His+xylB 7-7) also had multiple insertions of the xylB gene (FIG. 10), which resulted in increased in vivo activity of both the xylose isomerase and xylulose kinase within the cell (FIG. 13). This clone was capable of using either as much or more xylose than the parental strain, Iso-His #16, while producing significantly less xylitol (FIG. 15). Furthermore the Iso-His+xylB 7-7 produced more biomass than WT in the presence of xylose. These two strains showed that, not only is the presence of both the isomerase and the kinase genes important, but the number of insertions is as well.

Figure 17:
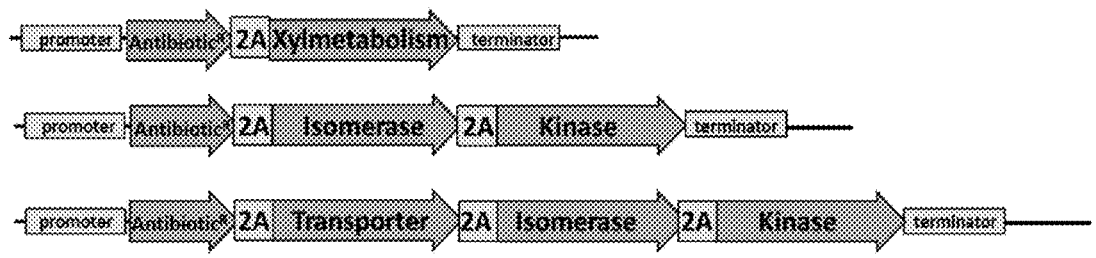
"
FIG. 17 is a schematic of different versions of the constructs used for transformation of ONC-T18.

To further optimize the iso-his & xylB containing "7-7" strain, this strain was transformed with a xylose transporter. FIG. 17 shows exemplary constructs for transformation. Examples of xylose transporters to be used include, but are not limited to, At5g17010 and At5g59250 (*Arabidopsis thaliana*), Gfx1 and GXS1 (*Candida*), AspTx (*Aspergillus*), and Sut1 (*Pichia*). Gxs1 (SEQ ID NO:23) was selected for transformation. The results are shown in FIGS. 19A, 19B, and 19C. The transformants 36-2, 36-9, and 36-16, containing GXS1 use more xylose than 7-7 and WT strains. They also use glucose slower than WT and 7-7 strains. The data demonstrate both xylose and glucose being used in the earlier stages by the GXS1 containing strains. Further, the percent of xylitol made by the GXS1 containing strains is lower than both WT and 7-7 strains.

Figure 25:
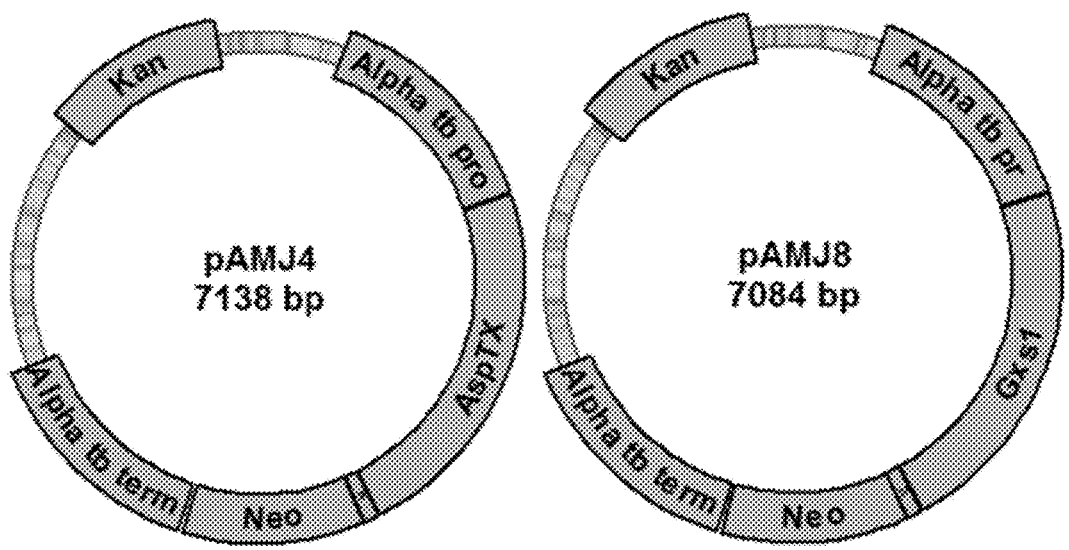
FIG. 25 is a schematic showing α-tubulin aspTx-neo and α-tubulin gxs1-neo constructs.
Figure 27C:
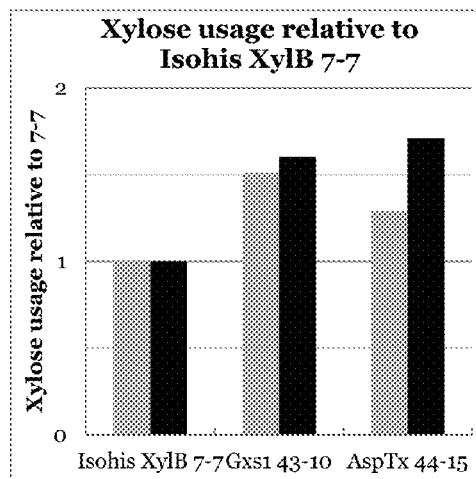
FIG. 27C is a bar graph showing xylose use relative to strain "7-7.
Figure 27D:
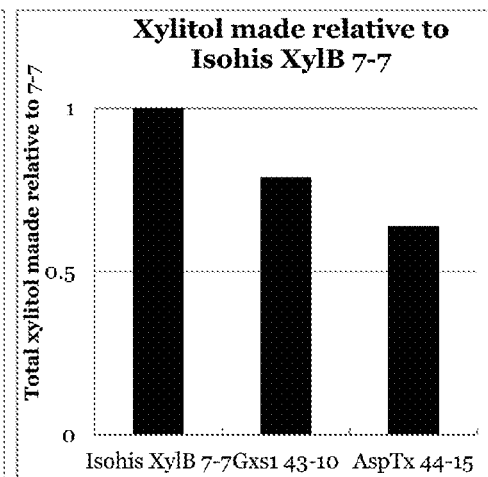
" FIG. 27D is a bar graph showing xylitol production made relative to strain "7-7."

To further analyze the effect of sugar transporters on the metabolism of xylose, codon optimized xylose transporters AspTX from *Aspergillus* (An11g01100) and Gxs1 from *Candida* were introduced in the 7-7 strain (isohis+xylB). FIG. 25 shows the alpha-tubulin aspTx-neo and alpha-tubulin gxs1-neo constructs. T18 transformants were created using standard biolistics protocols as described by BioRad's Biolistic PDS-1000/He Particle Delivery System. Briefly, 0.6 μm gold particles were coated with 2.5 μg of linearized plasmid DNA (EcoRI, 37° C., o/n), The coated gold particles were used to bombard WD plates previously spread with 1 ml of T18 cells at an OD600 of 1.0. The bombardment parameters included using a Helium pressure of 1350 or 1100 psi with a target distance of 3 or 6 cm. After an overnight recovery, the cells were washed off the plate and plated on media containing selection antibiotics (G418 at 2 mg/mL). Plates were incubated for 1 week at 25° C. to identify resistant colonies. The resulting transformants were screened by PCR and Southern blot (FIG. 26).

Southern blots were performed using standard protocols. Briefly, approximately 20 μg of genomic DNA were digested with 40 units of BamHI restriction enzyme in a total volume of 50 μL o/n/at 37° C. 7.2 μg of each digested sample was run on a 1.0% agarose gel at 50V for approximately 1.5. hours, with a digoxigenin (DIG) DNA molecular-weight marker II (Roche). DNA was depurinated in the gel by submerging the gel in 250 mM HCl for 15 minutes. The gel was further denatured by incubation in a solution containing 0.5 M NaOH and 1.5 M NaCL (pH 7.5) for two 15 minute washes. The reaction was then neutralized by incubation in 0.5 M Tris-HCl (pH 7.5) for two 15 minute washes. Finally, the gel was equilibrated in 20× saline-sodium citrate (SSC) buffer for 15 minutes. DNA was transferred to a positively charged nylon membrane (Roche) using a standard transfer apparatus. DNA was fixed to the membrane using a UV Stratalinker at an exposure of 120,000 µJ. Southern blot probe was generated using a PCR DIG Probe Synthesis Kit (Roche) to generate a DIG-labelled probe according to the manufacturer's instructions. The DNA affixed to the nylon membrane was prehybridised with 20 mL of DIG EasyHyb solution (DIG EasyHyb Granules, Roche). The DIG-labelled probe was denatured by adding 40 µL of the ble-probe reaction mixture to 300 µL of ddH$_2$O and incubated at 99° C. for 5 minutes. This solution was then added to 20 mL of DIG hybridization solution to create the probe solution. The probe solution was then added to the DNA-affixed nylon membrane and incubated at 53° C. overnight. The following day, the membrane was washed, twice, in 2×SSC, 0.1% SDS at RT. The membrane was further washed, twice, in 0.1× SSC, 0.1% SDS at 68° C. for 15 minutes. For detection, the membrane was washed and blocked using DIG Wash and Block Buffer set (Roche) according to the manufacturer's instructions. An anti-DIG-AP conjugated antibody from a DIG Nucleic Acid Detection Kit (Roche) was used for detection. 2 µL of the antibody solution was added to 20 mL detection solution and incubated with the membrane at RT for 30 minutes. The blot was then immersed in a washing buffer provided with the kit. CDP-Star (Roche) was used for visualization. 10 µL of the CDP-star solution was incubated on the membrane in 1 mL of detection solution, which was covered in a layer of 'sheet-protector' plastic to hold the solution to the membrane. Signal was immediately detected using a ChemiDoc imaging system.

For flasks assays, cells were grown in media for 2 to 3 days. Pellets were washed twice in media 2 (9 g/L NaCl, 4 g/L MgSO4, 100 mg/L CaCl2, 5 mg/L FeCl3, 20 g/L (NH4)2SO4, 0.86 g/L KH2PO4, 150 µg/L vitamin B12, 30 µg/L biotin, 6 mg/L thiamine hydrochloride, 1.5 mg/L cobalt (II) chloride, 3 mg/L manganese chloride) containing no sugar. Then, Media 2 containing 20 g/L Glucose and 20 g/L Xylose was inoculated to an OD600 of 0.05 with the washed cells. As shown in FIGS. 27A, 27B, 27C and 27D, the expression of the xylose isomerase, xylulose kinase, and either xylose transporters resulted in up to 71% more xylose used and 40% less xylitol produced than the parental strain 7-7.

Figure 28:
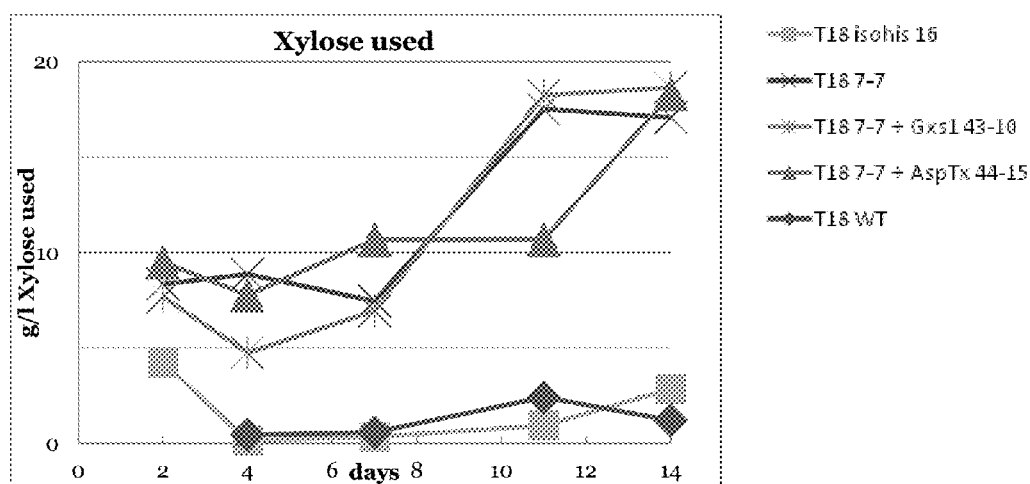
FIG. 28 is a graph showing growth of wild type (WT) (diamonds), isohis strain "16" (squares), strain "7-7" (x), and transporter strains Gxs1 (asterisks) and AspTx (triangles) in media containing xylose as sole carbon source.

For flasks assays, cells were grown in media for 2 to 3 days. Pellets were washed twice in saline. Then, media containing 60 g/L xylose instead of glucose was inoculated to an OD600 of 0.05 with the washed cells. Samples were taken at various time points and the amount of sugar remaining in the supernatant was analyzed by HPLC. FIG. 28 shows T18 growth in media containing xylose as the main carbon source requires over-expression of both an isomerase and a kinase. The expression of the transporters in this background did not significantly increase xylose usage in this media.

Figure 29A:
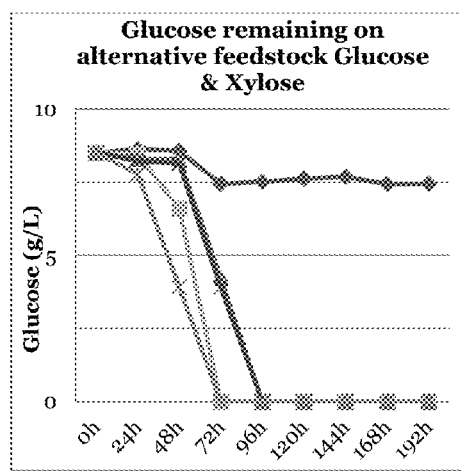
FIG. 29A is a graph showing remaining glucose in alternative feedstock containing glucose and xylose during growth of WT (squares), strain "7-7" (triangles), and transporter strains Gxs1 (asterisks) and AspTx (crosses).
Figure 29B:
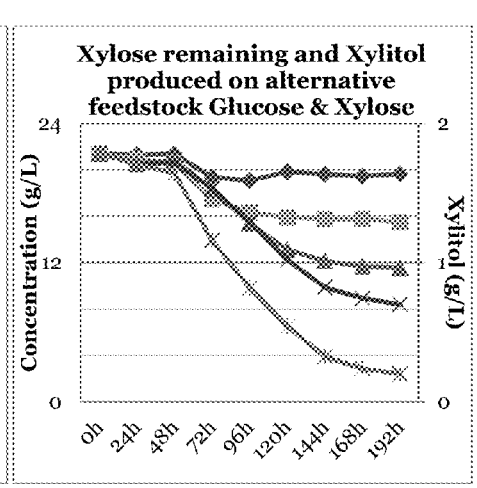
FIG. 29B is a graph showing xylose remaining and xylitol produced over time when WT (squares) strain "7-7" (triangles) and transporter strains Gxs1 (asterisks) and AspTx (crosses) are grown on alternative feedstock containing glucose and xylose.

Enhanced xylose usage by T18 7-7 and transporter strains was observed in media containing carbon from alternative feed stocks. For flasks assays, cells were grown in media for 2 to 3 days. Pellets were washed twice in 0.9% saline solution. Media 2 containing 20 g/L glucose:50 g/L xylose as a combination of lab grade glucose and glucose and xylose from an alternative feedstock from forestry, was inoculated to an OD600 nm of 0.05 with the washed cells. Samples were taken at various time points and the amount of sugar remaining in the supernatant was analyzed by HPLC. As shown in FIGS. 29A and 29B, in media containing sugars from an alternative feedstock, the T18 7-7 strains encoding for transporters used more xylose than wild-type, or T18 7-7.

What is claimed is:

1. A recombinant Thraustochytrid microorganism comprising two or more copies of a nucleic acid sequence encoding xylose isomerase, wherein the nucleic acid encoding xylose isomerase is an exogenous nucleic acid.

2. The recombinant Thraustochytrid microorganism of claim 1, further comprising at least one nucleic acid sequence encoding a xylulose kinase.

3. The recombinant Thraustochytrid microorganism of claim 2, further comprising at least one nucleic acid sequence encoding a xylose transporter.

4. The recombinant Thraustochytrid microorganism of claim 1, wherein the microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the exogenous nucleic acid sequence encoding xylose isomerase.

5. The recombinant Thraustochytrid microorganism of claim 1, wherein the nucleic acid sequence encoding the xylose isomerase is at least 90% identical to SEQ ID NO:2.

6. The recombinant Thraustochytrid microorganism of claim 2, wherein the microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the nucleic acid sequence encoding the xylulose kinase.

7. The recombinant Thraustochytrid microorganism of claim 2, wherein the nucleic acid sequence encoding the xylulose kinase is at least 90% identical to SEQ ID NO:17.

8. The recombinant Thraustochytrid microorganism of claim 3, wherein the microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the nucleic acid sequence encoding the xylose transporter.

9. The recombinant Thraustochytrid microorganism of claim 8, wherein the xylose transporter is GXS1 from *Candida intermedia*.

10. The recombinant Thraustochytrid microorganism of claim 8, wherein the nucleic acid sequence encoding the xylose transporter is at least 90% identical to SEQ ID NO:23.

11. The recombinant Thraustochytrid microorganism of claim 3, wherein the recombinant microorganism has increased xylose transport activity as compared to a non-recombinant control microorganism, increased xylose isomerase activity as compared to a non-recombinant control microorganism, increased xylulose kinase activity as compared to a non-recombinant control microorganism, or any combination thereof.

12. The recombinant Thraustochytrid microorganism of claim 3, wherein the recombinant microorganism grows with xylose as the sole carbon source.

13. The recombinant Thraustochytrid microorganism of claim 3, wherein the nucleic acid sequence encoding the xylose isomerase, the xylulose kinase and/or the xylose transporter is operably linked to a promoter.

14. The recombinant Thraustochytrid microorganism of claim 13, wherein the promoter is a tubulin promoter that is at least 80% identical to SEQ ID NO:25 or SEQ ID NO:26.

15. The recombinant Thraustochytrid microorganism of claim 3, wherein the nucleic acid sequence encoding the xylose isomerase, the xylulose kinase and/or the xylose transporter comprises a terminator.

16. The recombinant Thraustochytrid microorganism of claim 15, wherein the terminator is a tubulin terminator that is at least 80% identical to SEQ ID NO:27, SEQ ID NO:28, or SEQ ID NO:30.

17. The recombinant Thraustochytrid microorganism of claim 1, wherein the microorganism is ONC-T18.

18. A method of making a recombinant xylose-metabolizing Thraustochytrid microorganism comprising:
   providing one or more nucleic acid constructs comprising a nucleic acid sequence encoding a xylose isomerase, a nucleic acid sequence encoding a xylulose kinase and a nucleic acid sequence encoding a xylose transporter;
   transforming the Thraustochytrid microorganism with the one or more nucleic acid constructs; and
   isolating recombinant Thraustochytrid microorganisms comprising at least two or more copies of the nucleic acid sequences encoding the xylose isomerase.

19. The method of claim 18, further comprising isolating recombinant Thraustochytrid microorganisms comprising at least one copy of the nucleic acid sequence encoding the xylulose kinase.

20. The method of claim 19, isolating recombinant Thraustochytrid microorganisms comprising at least one copy of the xylose transporter.

21. The method of claim 18, wherein the providing comprises providing a first nucleic acid construct comprising a nucleic acid sequence encoding a xylose isomerase, a second nucleic acid construct comprising a nucleic acid sequence encoding a xylulose kinase and a third nucleic acid construct comprising a nucleic acid sequence encoding a xylose transporter.

22. The method of claim 21, wherein the first, second, and/or third nucleic acid construct comprises a promoter, a selectable marker, a nucleic acid sequence encoding a 2A peptide, the nucleic acid sequence encoding the xylose isomerase, and a terminator.

23. The method of claim 22, wherein the promoter is a tubulin promoter that is at least 80% identical to SEQ ID NO:25 or SEQ ID NO:26.

24. The method of claim 22, wherein the terminator is a tubulin terminator that is at least 80% identical to SEQ ID NO:27, SEQ ID NO:28, or SEQ ID NO:30.

25. The method of claim 18, wherein the isolated recombinant Thraustochytrid microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the exogenous nucleic acid sequence encoding xylose isomerase.

26. The method of claim 18, wherein the nucleic acid sequence encoding the xylose isomerase is at least 90% identical to SEQ ID NO:2.

27. The method of claim 18, wherein the isolated recombinant Thraustochytrid microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the nucleic acid sequence encoding the xylulose kinase.

28. The method of claim 18, wherein the nucleic acid sequence encoding the xylulose kinase is at least 90% identical to SEQ ID NO:17.

29. The method of claim 18, wherein the isolated recombinant Thraustochytrid microorganism comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 copies of the nucleic acid sequence encoding the xylose transporter.

30. The method of claim 29, wherein the xylose transporter is GXS1 from *Candida intermedia*.

31. The method of claim 29, wherein the nucleic acid sequence encoding the xylose transporter is at least 90% identical to SEQ ID NO:23.

32. The method of claim 18, wherein the isolated recombinant Thraustochytrid microorganism has increased xylose transport activity as compared to a control non-recombinant microorganism, increased xylose isomerase activity as compared to a control non-recombinant microorganism, increased xylulose kinase activity as compared to a control non-recombinant microorganism, or a combination thereof.

33. The method of claim 18, wherein the isolated recombinant Thraustochytrid microorganism grows with xylose as the sole carbon source.

34. The method of claim 18, wherein the Thraustochytrid microorganism is ONC-T18.

* * * * *